United States Patent
Powell et al.

(10) Patent No.: US 8,329,421 B2
(45) Date of Patent: *Dec. 11, 2012

(54) METHODS OF PREDICTING RESPONSE OF A NEOPLASM TO AN EGFR INHIBITOR AND DETECTING INTERACTIONS BETWEEN EGFR AND AN EGFR REGULATORY PROTEIN

(75) Inventors: William C. Powell, Renton, WA (US); Linda Willoughby Kivi, Marana, AZ (US); Patrick C. Roche, Tucson, AZ (US); Gary Gooch, Tucson, AZ (US); Fabien Gaire, Oro Valley, AZ (US)

(73) Assignee: Ventana Medical Systems, Inc., Tucson, AZ (US)

(*) Notice: Subject to any disclaimer, the term of this patent is extended or adjusted under 35 U.S.C. 154(b) by 31 days.

This patent is subject to a terminal disclaimer.

(21) Appl. No.: 12/668,991

(22) PCT Filed: Jul. 11, 2008

(86) PCT No.: PCT/US2008/069864
§ 371 (c)(1),
(2), (4) Date: Jun. 14, 2010

(87) PCT Pub. No.: WO2009/012175
PCT Pub. Date: Jan. 22, 2009

(65) Prior Publication Data
US 2010/0285025 A1 Nov. 11, 2010

Related U.S. Application Data

(60) Provisional application No. 60/949,792, filed on Jul. 13, 2007, provisional application No. 60/988,196, filed on Nov. 15, 2007.

(51) Int. Cl.
*G01N 33/53* (2006.01)
*G01N 33/563* (2006.01)
*G01N 33/574* (2006.01)
*G01N 33/577* (2006.01)
*G01N 33/58* (2006.01)

(52) U.S. Cl. ............... 435/7.23; 435/40.5; 435/40.52; 530/387.7; 530/388.1; 530/388.22; 530/388.8; 530/391.3

(58) Field of Classification Search ............. None
See application file for complete search history.

(56) References Cited

U.S. PATENT DOCUMENTS 4,943,533 A 7/1990 Mendelsohn et al.
(Continued)

FOREIGN PATENT DOCUMENTS

WO WO 2005/059138 A1 6/2005

OTHER PUBLICATIONS

Derecskei et al., Protocol modifications influence the result of EGF receptor immunodetection by EGFR parmDxTM in paraaffin-embedded cancer tissues, Path. Oncol. Res. 12(4):243-246, Dec. 2006.*

(Continued)

*Primary Examiner* — Claire Kaufman
(74) *Attorney, Agent, or Firm* — Klarquist Sparkman, LLP

(57) ABSTRACT

Disclosed herein are antigen-binding molecules, such as antibodies, that specifically recognize a portion of the EGFR C-terminal (intracellular) regulatory domain that interacts with one or more regulatory molecules (such as Suppressor of Cytokine Signaling ("SOCS") proteins). In certain normal or neoplastic cells and/or tissues, this region is inaccessible to the disclosed antigen-binding molecules. Thus, such antigen-binding molecules are useful at least to interrogate the regulated state of EGFR, predict the response of a cancer patient to EGFR inhibitor therapies, and/or predict the aggressiveness of neoplasms.

30 Claims, 10 Drawing Sheets

U.S. PATENT DOCUMENTS

| | | | |
|---|---|---|---|
| 2003/0104407 | A1 | 6/2003 | Ciossek et al. |
| 2006/0269519 | A1 | 11/2006 | Chen et al. |
| 2007/0009972 | A1 | 1/2007 | Chao et al. |
| 2008/0119399 | A1 | 5/2008 | Itoh et al. |
| 2009/0017050 | A1 | 1/2009 | Powell et al. |
| 2011/0217296 | A1* | 9/2011 | Carpen et al. |

OTHER PUBLICATIONS

Ventana Medical Systems Catalog, Confirm EGFR (Epidermal Growth Factor Receptor), Catalog # 790-4347 [online], 2010 [retrieved on Jan. 29, 2012].*

Beguinot et al., "Functional Studies on the EGF Receptor with an Antibody that Recognizes the Intracellular Portion of the Receptor," *J. Biol. Chem. 261*:1801-1807, 1986.

Bishayee et al., "Phosphorylation of Tyrosine 992, 1068, and 1086 is Required for Conformational Change of the Human Epidermal Growth Factor Receptor C-Terminal Tail," *Mol. Biol. Cell 10*:525-536, 1999.

Borghouts et al., "Peptide Aptamer Libraries," *Combinatorial Chemistry & High Throughput Screening 11*:135-145, 2008.

Buerger and Groner, "Bifunctional Recombinant Proteins in Cancer Therapy: Cell Penetrating Peptide Aptamers as Inhibitors of Growth Factor Signaling," *J. Cancer Res. Clin. Oncol. 129*:669-675, 2003.

Bullock et al., "Structure of the SOCS4-ElonginB/C Complex Reveals a Distinct SOCS Box Interface and the Molecular Basis for SOCS-Dependent EGFR Degradation," *Structure 15*:1493-1504, 2007.

Cell Signaling Technology, Inc., Datasheet #4404, "Phospho-EGF Receptor (Tyr1148) Antibody," 2005.

Chin et al., "Activation of the STAT Signaling Pathway Can Cause Expression of Caspase 1 and Apoptosis," *Mol. Cell. Biol. 17*:5328-5337, 1997.

Fitzgerald Industries International, Inc.; Polyclonal Antibody Data sheet for Rabbit Anti-EGFR, Catalog #RDI-EGFRCabrx; printed on Jun. 25, 2009.

Gullick et al., "Antibodies to the Autophosphorylation Sites of the Epidermal Growth Factor Receptor Protein-Tyrosine Kinase as Probes of Structure and Function," *EMBO J. 4*:2869-2877, 1985.

Haigler and Carpenter, "Production and Characterization of Antibody Blocking Epidermal Growth Factor: Receptor Interactions," *Biochim. Biophys. Acta 598*:314-325, 1980.

Hyland et al., "Generation and Functional Characterization of Intracellular Antibodies Interacting with the Kinase Domain of Human EGF Receptor," *Oncogene 22*:1557-1567, 2003.

Iwamoto et al., "Identification of a Membrane-Associated Inhibitor(s) of Epidermal Growth Factor-Induced Signal Transducer and Activator of Transcription Activation," *J. Biol. Chem. 273*:18198-18204, 1998.

Kario et al., "Suppressors of Cytokine Signaling 4 and 5 Regulate Epidermal Growth Factor Receptor Signaling," *J. Biol. Chem. 280*:7038-7048, 2005.

Kunz et al., "Peptide Aptamers with Binding Specificity for the Intracellular Domain of the ErbB2 Receptor Interfere with AKT Signaling and Sensitize Breast Cancer Cells to Taxol," *Mol. Cancer Res. 4*:983-998, 2006.

Laskin and Sandler, "Epidermal Growth Factor Receptor: A Promising Target in Solid Tumors," *Cancer Treatment Rev. 30*:1-17, 2004.

Le Tourneau et al., "Progress and Challenges in the Identification of Biomarkers for EGFR and VEGFR Targeting Anticancer Agents," *Drug Resistance Updates 11*:99-109, 2008.

Nicholson et al., "Suppressor of Cytokine Signaling (SOCS)-5 is a Potential Negative Regulator of Epidermal Growth Factor Signaling," *Proc. Natl. Acad. Sci. USA 102*:2328-2333, 2005.

Porter and Vaillancourt, "Tyrosine Kinase Receptor-Activated Signal Transduction Pathways Which Lead to Oncogenesis," *Oncogene 16*:1343-1352, 1998.

Schreiber et al., "Monoclonal Antibodies Against Receptor for Epidermal Growth Factor Induce Early and Delayed Effects of Epidermal Growth Factor," *Proc. Natl. Acad. Sci. USA 78*:7535-7539, 1981.

Song and Shuai, "The Suppressor of Cytokine Signaling (SOCS) 1 and SOCS3 but Not SOCS2 Proteins Inhibit Interferon-Mediated Antiviral and Antiproliferative Activities," *J. Biol. Chem. 273*:35056-35062, 1998.

Waterfield et al., "A Monoclonal Antibody to the Human Epidermal Growth Factor Receptor," *J. Cell Biochem. 20*:149-161, 1982.

Xia et al., "Identification of Both Positive and Negative Domains within the Epidermal Growth Factor Receptor COOH-Terminal Region for Signal Transducer and Activator of Transcription (STAT) Activation," *J. Biol. Chem. 277*:30716-30723, 2002.

Ponzetto et al., "A Multifunctional Docking Site Mediates Signaling and Transformation by the Hepatocyte Growth Factor/Scatter Factor Receptor Family," *Cell*, vol. 77, pp. 261-271, 1994.

* cited by examiner

FIG. 5B Normal Liver

| Peptide number | Sequence | Level of inhibition |
|---|---|---|
| Peptide 1 | QISLDNPDYQQD | Partial |
| Peptide 2 | QQDFFPKEAKPNG | Complete |
| Peptide 3 | LDNPDYQQDFFPKEAKPNG | Complete |

No peptide | Peptide-1 | Peptide-2 | Full Peptide

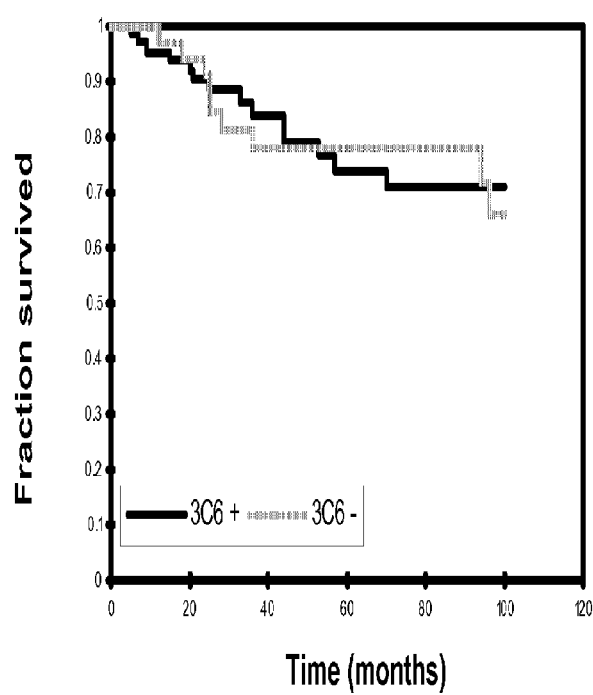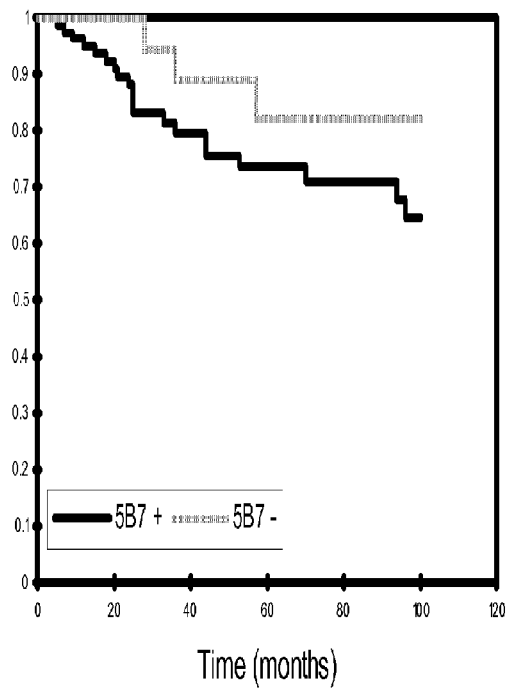

SEQUENCE LISTING

```
<160> NUMBER OF SEQ ID NOS: 6

<210> SEQ ID NO 1
<211> LENGTH: 1210
<212> TYPE: PRT
<213> ORGANISM: Homo sapiens

<400> SEQUENCE: 1

Met Arg Pro Ser Gly Thr Ala Gly Ala Ala Leu Leu Ala Leu Leu Ala
1               5                   10                  15

Ala Leu Cys Pro Ala Ser Arg Ala Leu Glu Glu Lys Lys Val Cys Gln
                20                  25                  30

Gly Thr Ser Asn Lys Leu Thr Gln Leu Gly Thr Phe Glu Asp His Phe
            35                  40                  45

Leu Ser Leu Gln Arg Met Phe Asn Asn Cys Glu Val Val Leu Gly Asn
        50                  55                  60

Leu Glu Ile Thr Tyr Val Gln Arg Asn Tyr Asp Leu Ser Phe Leu Lys
65                  70                  75                  80

Thr Ile Gln Glu Val Ala Gly Tyr Val Leu Ile Ala Leu Asn Thr Val
                85                  90                  95

Glu Arg Ile Pro Leu Glu Asn Leu Gln Ile Ile Arg Gly Asn Met Tyr
                100                 105                 110

Tyr Glu Asn Ser Tyr Ala Leu Ala Val Leu Ser Asn Tyr Asp Ala Asn
            115                 120                 125

Lys Thr Gly Leu Lys Glu Leu Pro Met Arg Asn Leu Gln Glu Ile Leu
        130                 135                 140
```

-continued

His Gly Ala Val Arg Phe Ser Asn Asn Pro Ala Leu Cys Asn Val Glu
145                 150                 155                 160

Ser Ile Gln Trp Arg Asp Ile Val Ser Ser Asp Phe Leu Ser Asn Met
                165                 170                 175

Ser Met Asp Phe Gln Asn His Leu Gly Ser Cys Gln Lys Cys Asp Pro
            180                 185                 190

Ser Cys Pro Asn Gly Ser Cys Trp Gly Ala Gly Glu Glu Asn Cys Gln
        195                 200                 205

Lys Leu Thr Lys Ile Ile Cys Ala Gln Gln Cys Ser Gly Arg Cys Arg
210                 215                 220

Gly Lys Ser Pro Ser Asp Cys Cys His Asn Gln Cys Ala Ala Gly Cys
225                 230                 235                 240

Thr Gly Pro Arg Glu Ser Asp Cys Leu Val Cys Arg Lys Phe Arg Asp
                245                 250                 255

Glu Ala Thr Cys Lys Asp Thr Cys Pro Pro Leu Met Leu Tyr Asn Pro
            260                 265                 270

Thr Thr Tyr Gln Met Asp Val Asn Pro Glu Gly Lys Tyr Ser Phe Gly
        275                 280                 285

Ala Thr Cys Val Lys Lys Cys Pro Arg Asn Tyr Val Val Thr Asp His
290                 295                 300

Gly Ser Cys Val Arg Ala Cys Gly Ala Asp Ser Tyr Glu Met Glu Glu
305                 310                 315                 320

Asp Gly Val Arg Lys Cys Lys Lys Cys Glu Gly Pro Cys Arg Lys Val
                325                 330                 335

Cys Asn Gly Ile Gly Ile Gly Glu Phe Lys Asp Ser Leu Ser Ile Asn
            340                 345                 350

Ala Thr Asn Ile Lys His Phe Lys Asn Cys Thr Ser Ile Ser Gly Asp
        355                 360                 365

Leu His Ile Leu Pro Val Ala Phe Arg Gly Asp Ser Phe Thr His Thr
370                 375                 380

Pro Pro Leu Asp Pro Gln Glu Leu Asp Ile Leu Lys Thr Val Lys Glu
385                 390                 395                 400

Ile Thr Gly Phe Leu Leu Ile Gln Ala Trp Pro Glu Asn Arg Thr Asp
                405                 410                 415

Leu His Ala Phe Glu Asn Leu Glu Ile Ile Arg Gly Arg Thr Lys Gln
            420                 425                 430

His Gly Gln Phe Ser Leu Ala Val Val Ser Leu Asn Ile Thr Ser Leu
        435                 440                 445

Gly Leu Arg Ser Leu Lys Glu Ile Ser Asp Gly Asp Val Ile Ile Ser
450                 455                 460

Gly Asn Lys Asn Leu Cys Tyr Ala Asn Thr Ile Asn Trp Lys Lys Leu
465                 470                 475                 480

Phe Gly Thr Ser Gly Gln Lys Thr Lys Ile Ile Ser Asn Arg Gly Glu
                485                 490                 495

Asn Ser Cys Lys Ala Thr Gly Gln Val Cys His Ala Leu Cys Ser Pro
            500                 505                 510

Glu Gly Cys Trp Gly Pro Glu Pro Arg Asp Cys Val Ser Cys Arg Asn
        515                 520                 525

Val Ser Arg Gly Arg Glu Cys Val Asp Lys Cys Asn Leu Leu Glu Gly
530                 535                 540

Glu Pro Arg Glu Phe Val Glu Asn Ser Glu Cys Ile Gln Cys His Pro
545                 550                 555                 560

Glu Cys Leu Pro Gln Ala Met Asn Ile Thr Cys Thr Gly Arg Gly Pro

```
                565                 570                 575
Asp Asn Cys Ile Gln Cys Ala His Tyr Ile Asp Gly Pro His Cys Val
            580                 585                 590

Lys Thr Cys Pro Ala Gly Val Met Gly Glu Asn Asn Thr Leu Val Trp
        595                 600                 605

Lys Tyr Ala Asp Ala Gly His Val Cys His Leu Cys His Pro Asn Cys
    610                 615                 620

Thr Tyr Gly Cys Thr Gly Pro Gly Leu Glu Gly Cys Pro Thr Asn Gly
625                 630                 635                 640

Pro Lys Ile Pro Ser Ile Ala Thr Gly Met Val Gly Ala Leu Leu Leu
            645                 650                 655

Leu Leu Val Val Ala Leu Gly Ile Gly Leu Phe Met Arg Arg Arg His
        660                 665                 670

Ile Val Arg Lys Arg Thr Leu Arg Arg Leu Leu Gln Glu Arg Glu Leu
    675                 680                 685

Val Glu Pro Leu Thr Pro Ser Gly Glu Ala Pro Asn Gln Ala Leu Leu
690                 695                 700

Arg Ile Leu Lys Glu Thr Glu Phe Lys Lys Ile Lys Val Leu Gly Ser
705                 710                 715                 720

Gly Ala Phe Gly Thr Val Tyr Lys Gly Leu Trp Ile Pro Glu Gly Glu
            725                 730                 735

Lys Val Lys Ile Pro Val Ala Ile Lys Glu Leu Arg Glu Ala Thr Ser
        740                 745                 750

Pro Lys Ala Asn Lys Glu Ile Leu Asp Glu Ala Tyr Val Met Ala Ser
    755                 760                 765

Val Asp Asn Pro His Val Cys Arg Leu Leu Gly Ile Cys Leu Thr Ser
770                 775                 780

Thr Val Gln Leu Ile Thr Gln Leu Met Pro Phe Gly Cys Leu Leu Asp
785                 790                 795                 800

Tyr Val Arg Glu His Lys Asp Asn Ile Gly Ser Gln Tyr Leu Leu Asn
            805                 810                 815

Trp Cys Val Gln Ile Ala Lys Gly Met Asn Tyr Leu Glu Asp Arg Arg
        820                 825                 830

Leu Val His Arg Asp Leu Ala Ala Arg Asn Val Leu Val Lys Thr Pro
    835                 840                 845

Gln His Val Lys Ile Thr Asp Phe Gly Leu Ala Lys Leu Leu Gly Ala
850                 855                 860

Glu Glu Lys Glu Tyr His Ala Glu Gly Gly Lys Val Pro Ile Lys Trp
865                 870                 875                 880

Met Ala Leu Glu Ser Ile Leu His Arg Ile Tyr Thr His Gln Ser Asp
            885                 890                 895

Val Trp Ser Tyr Gly Val Thr Val Trp Glu Leu Met Thr Phe Gly Ser
        900                 905                 910

Lys Pro Tyr Asp Gly Ile Pro Ala Ser Glu Ile Ser Ser Ile Leu Glu
    915                 920                 925

Lys Gly Glu Arg Leu Pro Gln Pro Pro Ile Cys Thr Ile Asp Val Tyr
930                 935                 940

Met Ile Met Val Lys Cys Trp Met Ile Asp Ala Asp Ser Arg Pro Lys
945                 950                 955                 960

Phe Arg Glu Leu Ile Ile Glu Phe Ser Lys Met Ala Arg Asp Pro Gln
            965                 970                 975

Arg Tyr Leu Val Ile Gln Gly Asp Glu Arg Met His Leu Pro Ser Pro
        980                 985                 990
```

Thr Asp Ser Asn Phe Tyr Arg Ala Leu Met Asp Glu Glu Asp Met Asp
        995                 1000                1005

Asp Val Val Asp Ala Asp Glu Tyr Leu Ile Pro Gln Gln Gly Phe
    1010                1015                1020

Phe Ser Ser Pro Ser Thr Ser Arg Thr Pro Leu Leu Ser Ser Leu
    1025                1030                1035

Ser Ala Thr Ser Asn Asn Ser Thr Val Ala Cys Ile Asp Arg Asn
    1040                1045                1050

Gly Leu Gln Ser Cys Pro Ile Lys Glu Asp Ser Phe Leu Gln Arg
    1055                1060                1065

Tyr Ser Ser Asp Pro Thr Gly Ala Leu Thr Glu Asp Ser Ile Asp
    1070                1075                1080

Asp Thr Phe Leu Pro Val Pro Glu Tyr Ile Asn Gln Ser Val Pro
    1085                1090                1095

Lys Arg Pro Ala Gly Ser Val Gln Asn Pro Val Tyr His Asn Gln
    1100                1105                1110

Pro Leu Asn Pro Ala Pro Ser Arg Asp Pro His Tyr Gln Asp Pro
    1115                1120                1125

His Ser Thr Ala Val Gly Asn Pro Glu Tyr Leu Asn Thr Val Gln
    1130                1135                1140

Pro Thr Cys Val Asn Ser Thr Phe Asp Ser Pro Ala His Trp Ala
    1145                1150                1155

Gln Lys Gly Ser His Gln Ile Ser Leu Asp Asn Pro Asp Tyr Gln
    1160                1165                1170

Gln Asp Phe Phe Pro Lys Glu Ala Lys Pro Asn Gly Ile Phe Lys
    1175                1180                1185

Gly Ser Thr Ala Glu Asn Ala Glu Tyr Leu Arg Val Ala Pro Gln
    1190                1195                1200

Ser Ser Glu Phe Ile Gly Ala
    1205                1210

<210> SEQ ID NO 2
<211> LENGTH: 19
<212> TYPE: PRT
<213> ORGANISM: Homo sapiens

<400> SEQUENCE: 2

Leu Asp Asn Pro Asp Tyr Gln Gln Asp Phe Phe Pro Lys Glu Ala Lys
1               5                   10                  15

Pro Asn Gly

<210> SEQ ID NO 3
<211> LENGTH: 225
<212> TYPE: PRT
<213> ORGANISM: Homo sapiens

<400> SEQUENCE: 3

Met Val Thr His Ser Lys Phe Pro Ala Ala Gly Met Ser Arg Pro Leu
1               5                   10                  15

Asp Thr Ser Leu Arg Leu Lys Thr Phe Ser Ser Lys Ser Glu Tyr Gln
                20                  25                  30

Leu Val Val Asn Ala Val Arg Lys Leu Gln Glu Ser Gly Phe Tyr Trp
            35                  40                  45

Ser Ala Val Thr Gly Gly Glu Ala Asn Leu Leu Leu Ser Ala Glu Pro
        50                  55                  60

Ala Gly Thr Phe Leu Ile Arg Asp Ser Ser Asp Gln Arg His Phe Phe
65                  70                  75                  80

```
Thr Leu Ser Val Lys Thr Gln Ser Gly Thr Lys Asn Leu Arg Ile Gln
                85                  90                  95
Cys Glu Gly Gly Ser Phe Ser Leu Gln Ser Asp Pro Arg Ser Thr Gln
            100                 105                 110
Pro Val Pro Arg Phe Asp Cys Val Leu Lys Leu Val His His Tyr Met
        115                 120                 125
Pro Pro Pro Gly Ala Pro Ser Phe Pro Ser Pro Thr Glu Pro Ser
    130                 135                 140
Ser Glu Val Pro Glu Gln Pro Ser Ala Gln Pro Leu Pro Gly Ser Pro
145                 150                 155                 160
Pro Arg Arg Ala Tyr Tyr Ile Tyr Ser Gly Gly Glu Lys Ile Pro Leu
                165                 170                 175
Val Leu Ser Arg Pro Leu Ser Ser Asn Val Ala Thr Leu Gln His Leu
            180                 185                 190
Cys Arg Lys Thr Val Asn Gly His Leu Asp Ser Tyr Glu Lys Val Thr
        195                 200                 205
Gln Leu Pro Gly Pro Ile Arg Glu Phe Leu Asp Gln Tyr Asp Ala Pro
    210                 215                 220
Leu
225

<210> SEQ ID NO 4
<211> LENGTH: 4
<212> TYPE: PRT
<213> ORGANISM: Artificial Sequence
<220> FEATURE:
<223> OTHER INFORMATION: Peptide SH2 docking motif.
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: MISC_FEATURE
<222> LOCATION: (4)..(4)
<223> OTHER INFORMATION: Xaa can be any Leu or Val

<400> SEQUENCE: 4

Tyr Xaa Xaa Xaa
1

<210> SEQ ID NO 5
<211> LENGTH: 4
<212> TYPE: PRT
<213> ORGANISM: Artificial Sequence
<220> FEATURE:
<223> OTHER INFORMATION: Peptide SH2 docking motif.
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (4)..(4)
<223> OTHER INFORMATION: Xaa can be any Pro or Asp

<400> SEQUENCE: 5

Tyr Xaa Xaa Xaa
1

<210> SEQ ID NO 6
<211> LENGTH: 19
<212> TYPE: PRT
<213> ORGANISM: Artificial Sequence
<220> FEATURE:
<223> OTHER INFORMATION: Regulatory domain peptide consensus sequence
```

```
<220> FEATURE:
<221> NAME/KEY: misc_feature
<222> LOCATION: (1)..(6)
<223> OTHER INFORMATION: Xaa can be any naturally occurring amino acid
<220> FEATURE:
<221> NAME/KEY: misc_feature
<222> LOCATION: (14)..(19)
<223> OTHER INFORMATION: Xaa can be any naturally occurring amino acid

<400> SEQUENCE: 6

Xaa Xaa Xaa Xaa Xaa Xaa Gln Gln Asp Phe Phe Pro Lys Xaa Xaa Xaa
1               5                   10                  15

Xaa Xaa Xaa
```

US 8,329,421 B2

METHODS OF PREDICTING RESPONSE OF A NEOPLASM TO AN EGFR INHIBITOR AND DETECTING INTERACTIONS BETWEEN EGFR AND AN EGFR REGULATORY PROTEIN

CROSS REFERENCE TO RELATED APPLICATIONS

This is the U.S. National Stage of International Application No. PCT/US2008/069864, filed Jul. 11, 2008, which was published in English under PCT Article 21(2), which in turn claims priority to U.S. Provisional Application Nos. 60/949,792 filed Jul. 13, 2007 and 60/988,196 filed Nov. 15, 2007, herein incorporated by reference.

FIELD OF THE DISCLOSURE

This disclosure concerns antigen-binding molecules, such as antibodies, specific for a portion of the intracellular domain of epidermal growth factor receptor ("EGFR") and uses of such antigen-binding molecules, for instance, as cancer prognostics and/or as indicators for particular (e.g., EGFR inhibitor) cancer therapies.

BACKGROUND

Cancer is a generic name for a wide range of cellular malignancies characterized by unregulated growth, lack of differentiation, and the ability to invade local tissues and metastasize. These neoplastic malignancies affect, with various degrees of prevalence, every tissue and organ in the body. Historically, cancers have been diagnosed using conventional histological and clinical features of the affected tissue or organ. However, it is now apparent that tumors, even from the same tissue or organ, are heterogeneous on the cellular and/or molecular level. As one consequence, the prognosis and/or responsiveness to therapy of each patient may differ. This unpredictability confounds treatment selection and may expose patients to the risks and discomforts of unneeded therapies.

EGFR-positive cancers offer a case in point. EGFR and its downstream signaling effectors, including members of the Ras/Raf/MAP kinase pathway, play an important role in both normal and malignant epithelial cell biology (Normanno et al., Gene, 366:2-16, 2006). Amplification and/or mutation of the EGFR gene and/or EGFR protein overexpression have been associated with various malignancies, including breast cancer, lung cancer, colorectal cancer, ovarian cancer, renal cell cancer, bladder cancer, head and neck cancer, glioblastoma, and/or astrocytoma. Increased EGFR activity (whether as a result of abnormally high protein expression, dysregulation of receptor activity, or other mechanism) is believed to contribute to carcinogenesis. Consequently, EGFR is an established target for therapeutic development.

Several EGFR inhibitors are available for clinical treatment. These include EGFR-specific antibodies (e.g., cetuximab (ERBITUX™) and panitumumab (VECTIBIX™)) and small molecular tyrosine kinase inhibitors (e.g., gefitinib (IRESSA™) and erlotinib (TARCEVA™)). While these treatments have benefited subsets of cancer patients, responses to the drugs are variable. For example, three clinical studies of patients with advanced colorectal cancer using cetuximab in a monotherapy setting and/or in combination with irinotecan (a chemotherapeutic agent) demonstrated response rates of 10.5% or 10.8% for cetuximab alone and 22.5% or 22.9% for the combined therapy (reviewed by Iqbal and Lenz, Cancer Chemother. Pharmacol., 54(Suppl. 1):S32-39, 2004). Similarly, about 10% or about 20% of non-small cell lung cancer ("NSCLC") patients treated with 250 or 500 gefitinib per day, respectively, responded to the drug and exhibited improved symptoms (Birnbaum and Ready, Curr. Treat. Options Oncol., 6(1):75-81, 2005).

Patient responses to EGFR inhibitors have been correlated with various EGFR metrics. For example, EGFR expression (as measured by immunohistochemistry) was associated with an objective response to erlotinib treatment in NSCLC patients (Tsao et al., N. Engl. J. Med., 353:133-144, 2005). However, survival after treatment in these patients was not influenced by EGFR expression, the number of EGFR copies, or EGFR mutation (Tsao et al., N. Engl. J. Med., 353:133-144, 2005). In both preclinical and clinical settings, somatic mutations in the EGFR tyrosine kinase domain were found to correlate with sensitivity of NSCLC patients to gefitinib and erlotinib but not to cetuximab (Janne et al., J. Clin. Oncol., 23:3227-3234, 2005). Clinical studies of gefitinib demonstrated an association between increased EGFR copy number, mutational status, and clinical response in advanced NSCLC (Cappuzzo et al., J. Natl. Cancer Inst., 97:643-655, 2005).

EGFR antibodies in clinical use (e.g., cetuximab (ERBITUX™) and panitumumab (VECTIBIX™)) bind to the extracellular domain of the EGFR. This receptor domain includes the ligand binding site and these antibodies are believed to blocking ligand binding; thereby, disrupting EGFR signaling. As a result of the therapeutic utility of such EGFR antibodies, many subsequent studies have focused on the production of antibodies (or other binding molecules) specific for the EGFR extracellular domain (see, e.g., U.S. Pat. Nos. 5,459,061, 5,558,864, 5,891,996, 6,217,866, 6,235,883, 6,699,473, and 7,060,808; European Pat. Nos. EP0359282 and EP0667165).

Less attention has been paid to antibodies specific for the EGFR cytoplasmic domain, particularly for therapeutic purposes. However, for example, Hyland et al. proposed the intracellular expression of single-chain antibodies (e.g., scFvs) as a promising approach for selective interference with EGFR signaling. Others have described antibodies specific for the EGFR intracellular domain at least for detection purposes (e.g., Lin et al., Cell. Mol. Immunol., 1(2):137-141, 2004; Hyland et al., Oncogene, 22(10):1557-1567, 2003, Panneerselvam et al., J. Biol. Chem., 270(14):7975-7979, 1995; Gullick et al., J. Pathol., 164(4):285-289, 1991; Dazzi et al., Anal. Cell. Pathol., 3(2):69-75, 1991), and some antibodies specific for the EGFR intracellular domain are commercially available (e.g., Epitomics (Burlingame, Calif., USA), Cat. Nos. 1902-1 and 2235-1; Cell Signaling Technologies (Danvers, Mass., USA), Cat. Nos. 4405 and 2239; Spring Bioscience (Fremont, Calif., USA), Cat. No. E2451).

At least one study compared the reactivity of antibodies specific for the EGFR external and internal domains in the same set of lung cancer tissues (Dazzi et al., Anal. Cell. Pathol., 3(2):69-75, 1991). No significant differences in the reactivity of these antibodies were observed.

The continued clinical development of EGFR inhibitor therapies would benefit from a parallel strategy for identifying patient populations most likely to respond to such treatments. New prognostic and predictive markers, which would facilitate an individualization of therapy for each patient, are needed to accurately predict patient responses to treatments and help clinicians distinguish among treatment choices for such patients.

SUMMARY OF THE DISCLOSURE

Disclosed herein are methods of interrogating the status of EGFR regulation (and, therefore, EGFR activity state) in biological samples (such as formalin-fixed, paraffin-embedded ("FFPE") tissue sections). EGFR activation status predicts, among other things, the aggressiveness of EGFR-positive neoplasms and/or the potential efficacy of EGFR-targeted therapies that depend at least in part upon EGFR activation status. The disclosed methods involve the use of antigen-binding molecules (also referred to as RD-binding molecules) that specifically bind to the intracellular regulatory domain of EGFR. The status of EGFR regulation in normal or neoplastic cells and/or tissues can be differentiated by the accessibility of the EGFR regulatory domain to RD-binding molecules (including disclosed RD-binding molecules).

Also disclosed are peptides derived from the EGFR regulatory domain (regulatory domain peptides or RDPs) and, in particular, from the region having the sequence LDNPDYQQDFFPKEAKPNG (the "L2G" sequence or peptide; SEQ ID NO: 2). RDPs are useful, at least, in the making of exemplary RD-binding molecules and as otherwise provided in this disclosure. In some examples RD-binding molecules, such as antibodies, specifically recognize an epitope included in an RDP sequence, for example within the L2G sequence.

The foregoing and other features will become more apparent from the following detailed description of several embodiments, which proceeds with reference to the accompanying figures.

BRIEF DESCRIPTION OF THE FIGURES

FIGS. 5A and 5B show the results of staining the indicated tissues with EGFR extracellular-domain-specific clone 3C6 and EGFR regulatory-domain-specific clone 5B7 in tabular (FIG. 5A) and image (FIG. 5B) formats.

FIG. 7A shows three peptides (Peptide 1, amino acids 1164-1175 of SEQ ID NO: 1; Peptide 2, amino acids 7-19 of SEQ ID NO: 2; Peptide 3, SEQ ID NO: 2). The boxed region in FIG. 7A (amino acids 1173-1175 of SEQ ID NO: 1 and amino acids 7-14 of SEQ ID NO: 2) represents an exemplary clone 5B7 epitope, the C-terminus of which may be a few amino acids longer or shorter.

FIGS. 9A and 9B show two Kaplan Meier plots demonstrating overall survival of NSCLC patients as a function of clone 3C6 (FIG. 9A) or 5B7 (FIG. 9B) status. In FIG. 9A, 3C6-positive staining is shown by a black line and 3C6-negative staining is shown by a gray line. In FIG. 9B, 5B7-positive staining is shown by a black line and 5B7-negative staining is shown by a gray line.

FIGS. 10 and 10B show two Kaplan Meier plots demonstrating disease-free survival of NSCLC patients as a function of clone 3C6 (FIG. 10A) or 5B7 (FIG. 10B) status. In FIG. 10A, 3C6-positive staining is shown by a black line and 3C6-negative staining is shown by a gray line. In FIG. 10B, 5B7-positive staining is shown by a black line and 5B7-negative staining is shown by a gray line.

FIG. 10 shows two Kaplan Meier plots demonstrating disease-free survival of NSCLC patients as a function of clone 3C6 (panel A) or 5B7 (panel B) status. In panel A, 3C6-positive staining is shown by a black line and 3C6-negative staining is shown by a gray line. In panel B, 5B7-positive staining is shown by a black line and 5B7-negative staining is shown by a gray line.

SEQUENCE LISTING

Figure 1:
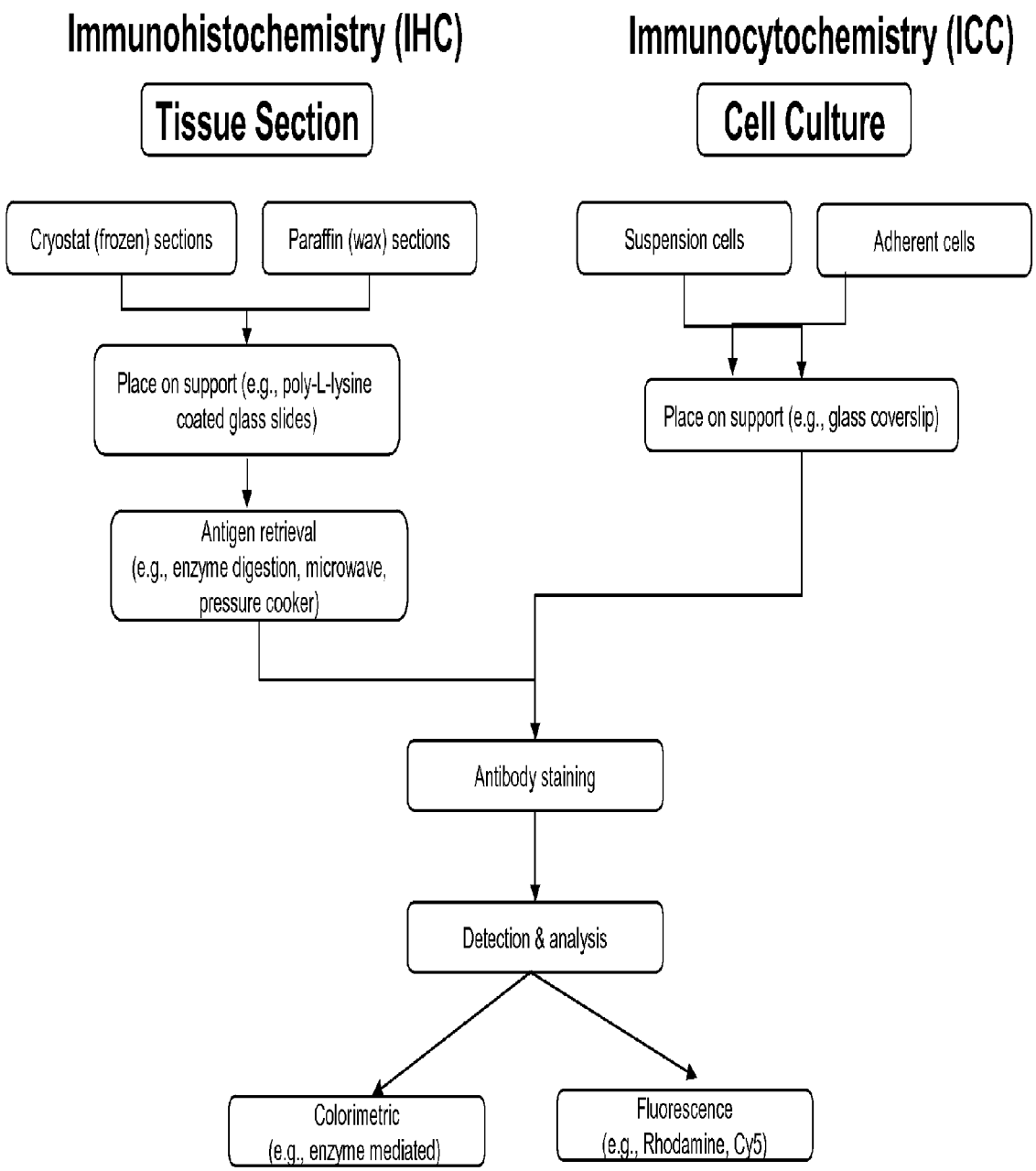
FIG. 1 is a flow chart schematically showing the steps of exemplary immunostaining methods.

The nucleic and amino acid sequences listed in the accompanying sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. All sequence database accession numbers referenced herein are understood to refer to the version of the sequence identified by that accession number as it was available on the priority date of this application (Jul. 13, 2007). In the accompanying sequence listing:

SEQ ID NO: 1 is a reference amino acid sequence (REFSEQ) of human EGFR (isoform a) as set forth in GENBANK™ Accession No. NM_005228. A nucleic acid sequence encoding this polypeptide also is set forth in GENBANK™ Accession No. NM_005228.

SEQ ID NO: 2 is the amino acid sequence of a peptide corresponding to residues 1167-1185 of SEQ ID NO: 1.

SEQ ID NO: 3 is the curated reference amino acid sequence (REFSEQ) of human Suppressor of Cytokine Signaling 3 (SOCS3) as set forth in GENBANK™ Accession No. NM_003955. A nucleic acid sequence encoding this polypeptide also is set forth in GENBANK™ Accession No. NM_003955.

SEQ ID NO: 4 is a YXXL/V protein motif.

SEQ ID NO: 5 is a YXXP/D protein motif.

SEQ ID NO: 6 shows an exemplary RDP consensus sequence.

DETAILED DESCRIPTION

I. Introduction

Disclosed herein are EGFR regulatory domain peptides ("RDPs"), which include, e.g., isolated peptides consisting of amino acid residues 1167-1185 of SEQ ID NO: 1 or an immunogenic fragment of said peptide. Also disclosed are (EGFR) regulatory domain (RD)-binding molecules that specifically binds to such peptides. Some embodiments include a RD-binding molecule that specifically binds to residues 1138-1196 of SEQ ID NO: 1 or a SOCS-protein-binding fragment thereof (e.g., a SOCS3-binding fragment).

Also disclosed are compositions including an EGFR RD-binding molecule the binding of which to EGFR is competitively inhibited by a disclosed RDP (such as an isolated peptide consisting of amino acid residues 1167-1185 of SEQ ID NO: 1 or an immunogenic fragment of said peptide). Other disclosed compositions include an EGFR RD-binding molecule the binding of which to EGFR is competitively inhibited by a Suppressor of Cytokine Signaling (SOCS) protein (such as, a SOCS1 protein (e.g., see GenBank Accession Nos. NP_003736.1, EAW85163.1 and AAD27709.1) or a SOCS3 protein (e.g., see GenBank Accession Nos. CAG46495.1, CAG38736.1 and AAH60858.1), or, in particular embodiments, a SOCS3 protein).

In any embodiment involving a RD-binding molecule (whether composition or method), an RD-binding molecule can be (but is not necessarily) an antibody (e.g., a monoclonal antibody, such as a rabbit or mouse monoclonal antibody) or a antigen-binding fragment thereof.

Further disclosed are methods of producing an EGFR-specific antibody, comprising immunizing a non-human mammal with an immunogen comprising a carrier protein and a disclosed RDP (such as, amino acid residues 1167-1185 of SEQ ID NO: 1 or an immunogenic fragment of said peptide). Some such methods include a further step of isolating serum from the non-human mammal and isolating polyclonal antibody specific for the immunogen. Other such methods include a further step of fusing spleen cells from the non-human animals with a fusion cell partner to make antibody-producing hybridomas.

Disclosed methods also include predicting the response of a neoplasm to an EGFR inhibitor by detecting in a biological sample, which includes one or more neoplastic cells, the specific binding of a disclosed EGFR RD-binding antibody to the one or more of the neoplastic cells; wherein specific binding of the antibody to one or more of the neoplastic cells indicates that the neoplastic cells will respond to an EGFR inhibitor. In some method embodiments, the neoplastic cell response is slowed growth (such as, net zero growth or net negative growth). In other method embodiments, the slowed growth is at least 10% (such as at least 15%, at least 20%, at least 30%, at least 50%, or at least 75%) less than the neoplastic cell growth prior to treatment with the EGFR inhibitor. In some method embodiments, the neoplastic cell response is apoptosis, and, in some such embodiments, at least 10% (such as at least 15%, at least 20%, at least 30%, at least 50%, or at least 75%) of the neoplastic cells undergo apoptosis.

Also disclosed are methods for predicting whether a candidate for treatment with an EGFR inhibitor is likely to respond to such treatment by detecting in a biological sample from a candidate for treatment with an EGFR inhibitor, which biological sample comprises one or more neoplastic cells, the specific binding of a disclosed EGFR RD-binding antibody to the one or more of the neoplastic cells; wherein specific binding of the antibody to one or more of the neoplastic cells indicates that the candidate is likely to respond to treatment with an EGFR inhibitor. In some method embodiments, the specific binding of the antibody to at least 10% (such as at least 15%, at least 20%, at least 30%, at least 50%, or at least 75%) of the neoplastic cells in the biological sample indicates that the candidate is likely to respond to treatment with an EGFR inhibitor.

Other disclosed methods involve predicting the response of a neoplasm to an EGFR inhibitor by detecting in a biological sample comprising one or more EGFR-positive neoplastic cells substantially no specific binding of a disclosed EGFR RD-binding antibody to the one or more EGFR-positive neoplastic cells; wherein substantially no specific binding of the antibody to the EGFR-positive neoplastic cells indicates that the neoplastic cells will not substantially respond to an EGFR inhibitor. Some such methods further involve detecting in a control biological material (such as normal skin, normal testis, or normal tonsil) the specific binding to EGFR of the antibody. Other such methods further involve detecting in the biological sample specific binding of a second antibody specific for the EGFR external domain.

Still other disclosed methods involve predicting the response of a neoplasm to EGFR inhibitor administration, by detecting EGFR expression in a first sample of a biological material comprising one or more neoplastic cells; and detecting in a second sample of the biological material substantially no specific binding to EGFR of a disclosed EGFR RD-binding antibody; wherein detecting EGFR expression in the first sample and substantially no specific binding to EGFR of a disclosed EGFR RD-binding antibody indicates that the neoplasm is likely to respond to EGFR inhibitor administration. In some such methods, the first sample and the second sample are serial sections of the biological material. Other such methods further involve detecting in a control biological material (such as, normal skin, normal testis, or normal tonsil) the specific binding to EGFR of the disclosed EGFR RD-binding antibody.

Also disclosed are methods for predicting prognosis of a neoplastic disease (such as lung cancer, colorectal cancer, head and neck cancer, gastric cancer, or glioblastoma), including detecting in a biological sample from a patient having a neoplastic disease the specific binding of a disclosed EGFR RD-binding antibody to one or more EGFR-positive neoplastic cells in the biological sample; wherein the specific binding of the antibody in the one or more EGFR-positive neoplastic cells predicts a poor prognosis of the neoplastic disease in the patient. In some such method embodiments, the antibody specifically binds to at least 10% (such as at least 15%, at least 20%, at least 30%, at least 50%, or at least 75%) of the EGFR-positive neoplastic cells in the biological sample. In some method embodiments, a poor prognosis is less than 5-year survival (such as less than 1-year survival or less than 2-year survival) of the patient after initial diagnosis of the neoplastic disease.

Other prognostic method embodiments involve detecting in a biological sample from a patient having a neoplastic disease (such as lung cancer, colorectal cancer, head and neck cancer, gastric cancer, or glioblastoma) the specific binding of a disclosed EGFR RD-binding antibody to one or more EGFR-positive neoplastic cells in the biological sample; wherein substantially no specific binding of the antibody in the one or more EGFR-positive neoplastic cells predicts a good prognosis of the neoplastic disease in the patient. In some method embodiments, a good prognosis is greater than 2-year survival (such as greater than 3-year survival, greater than 5-year survival, or greater than 7-year survival) of the patient after initial diagnosis of the neoplastic disease.

Immunostaining methods also are disclosed. Such methods involve contacting a biological sample, comprising one or more cells, with a disclosed EGFR RD-binding antibody, and detecting the specific binding of the antibody to an antigen (e.g., EGFR) in the one or more cells.

Other disclosed methods involve detecting a direct interaction between EGFR and an EGFR regulatory protein (such as a SOCS protein, e.g., SOCS1 or SOCS3), by contacting a biological sample, comprising one or more EGFR-positive cells, with a disclosed EGFR RD-binding antibody, and detecting the specific binding of the antibody to the one or more EGFR-positive cells, wherein the specific binding of the antibody to the one or more EGFR-positive cells detects that EGFR is not significantly interacting with an EGFR regulatory protein, wherein an interaction between EGFR and the EGFR regulatory protein masks the epitope of the antibody.

Other methods of detecting a direct interaction between EGFR and an EGFR regulatory protein (such as a SOCS protein, e.g., SOCS1 or SOCS3) are disclosed. Such methods involve contacting a biological sample, comprising one or more EGFR-positive cells, with a disclosed EGFR RD-binding antibody, and detecting the specific binding of the antibody to the one or more EGFR-positive cells, wherein substantially no specific binding of the antibody to the one or more EGFR-positive cells detects that EGFR is interacting with an EGFR regulatory protein, wherein an interaction between EGFR and the EGFR regulatory protein masks the epitope of the antibody.

In any disclosed method embodiment involving a biological sample, such biological sample can be (but is not necessarily) mounted on a microscope slide, is a tissue section (such as a formalin-fixed and paraffin-embedded tissue section), and/or is a neoplastic tissue (such as, a lung cancer, colorectal cancer, head and neck cancer, gastric cancer, or glioblastoma).

II. Abbreviations and Terms

| | |
|---|---|
| EGFR | epidermal growth factor receptor (e.g., OMIM Accession No. 131550) |
| IHC | immunohistochemistry |
| NSCLC | non-small cell lung cancer |
| RDP | EGFR regulatory domain peptide |
| RD | EGFR regulatory domain |
| SH2 domain | Src homology 2 domain |
| SOCS protein | suppressor of cytokine signaling protein (e.g., OMIM Accession Nos. 604176 or 603597) |
| STAT | signal transducer and activator of transcription |

Unless otherwise noted, technical terms are used according to conventional usage. Definitions of common terms in cell and molecular biology may be found in Benjamin Lewin, Genes V, published by Oxford University Press, 1994 (ISBN 0-19-854287-9); Kendrew et al. (eds.), The Encyclopedia of Molecular Biology, published by Blackwell Science Ltd., 1994 (ISBN 0-632-02182-9); and Robert A. Meyers (ed.), Molecular Biology and Biotechnology: a Comprehensive Desk Reference, published by VCH Publishers, Inc., 1995 (ISBN 1-56081-569-8).

In order to facilitate review of various embodiments of a disclosed invention, the following explanations of specific terms are provided:

Antigen-binding molecule: A molecule that specifically binds to an epitope in a target molecule (e.g., an antigen, such as a protein or nucleic acid molecule). Exemplary antigen-binding molecules are provided elsewhere in this disclosure.

Species of antigen-binding molecules described herein include, without limitation, interface-specific binding molecules, RD-binding molecules, and control antigen-binding molecules. These species of antigen-binding molecules are characterized by the nature of the target molecule and/or the location in the target molecule of the epitope to which the species specifically binds as more particularly defined elsewhere in this disclosure.

Epitope: A site on a target molecule (e.g., an antigen, such as a protein or nucleic acid molecule) to which an antigen-binding molecule (e.g., an antibody, antibody fragment, scaffold protein containing antibody binding regions, or aptamer) binds. Epitopes can be formed both from contiguous or juxtaposed noncontiguous residues (e.g., amino acids or nucleotides) of the target molecule. Epitopes formed from contiguous residues (e.g., amino acids or nucleotides) typically are retained on exposure to denaturing solvents whereas epitopes formed by tertiary folding typically are lost on treatment with denaturing solvents. An epitope typically includes at least 3, and more usually, at least 5 or 8-10 residues (e.g., amino acids or nucleotides). Typically, an epitope also is less than 20 residues (e.g., amino acids or nucleotides) in length, such as less than 15 residues or less than 12 residues.

Immunogen: A molecule (also called an antigen) capable of provoking an immune response (e.g., the production of antibodies) when introduced into an animal with a functioning immune system. Exemplary immunogens including, for instance, proteins (or protein fragments), polysaccharides, and small molecules (haptens) or peptides coupled to a carrier molecule (e.g., a protein such as bovine serum albumin ("BSA"), keyhole limpet hemocyanin ("KLH") or polylysine). An "immunogenic fragment" is a portion of a polypeptide or other immunogen that is capable of provoking an immune response either by itself or when conjugated to a carrier molecule. Immunogens and immunogenic fragments include one or more epitopes within their sequences.

Isolated: An "isolated" biological component (e.g., a nucleic acid molecule, chemical compound, protein or organelle) has been substantially separated or purified away from other biological components (e.g., nucleic acid molecules, chemical compounds, proteins or organelles) with which the component is commingled (e.g., in the cell of an organism or in a plant cell extract). Nucleic acids, proteins and chemical compounds that have been "isolated" include nucleic acids, proteins and chemical compounds purified by standard purification methods. The term "isolated" also embraces nucleic acids and proteins prepared by recombinant expression in a host cell as well as chemically synthesized nucleic acids and chemical compounds.

Peptide: Two or more amino acids joined by a peptide bond. Typically, a peptide consists of fewer than fifty amino acids; for example, consisting of approximately 7 to approximately 40 amino acids, consisting of approximately 7 to approximately 30 amino acids, consisting of approximately 7 to approximately 20 amino acids.

Specific binding (or obvious derivations of such phrase, such as specifically binds, specific for, etc.) refers to the particular interaction between one binding partner (such as an EGFR RD-binding molecule) and another binding partner (such as a target of an EGFR RD-binding molecule). Such interaction is mediated by one or, typically, more noncovalent bonds between the binding partners (or, often, between a specific region or portion of each binding partner). In contrast to non-specific binding sites, specific binding sites are saturable. Accordingly, one exemplary way to characterize specific binding is by a specific binding curve. A specific binding curve shows, for example, the amount of one binding partner (the first binding partner) bound to a fixed amount of the other binding partner as a function of the first binding partner concentration. As the first binding partner concentration increases under these conditions, the amount of the first binding partner bound will saturate. In another contrast to non-specific binding sites, specific binding partners involved in a direct association with each other (e.g., a protein-protein interaction) can be competitively removed (or displaced) from such association (e.g., protein complex) by excess amounts of either specific binding partner. Such competition assays (or displacement assays) are very well known in the art.

Unless otherwise explained, all technical and scientific terms used herein have the same meaning as commonly understood by one of ordinary skill in the art to which a disclosed invention belongs. The singular terms "a," "an," and "the" include plural referents unless context clearly indicates otherwise. Similarly, the word "or" is intended to include "and" unless the context clearly indicates otherwise. "Comprising" means "including." Hence "comprising A or B" means "including A" or "including B" or "including A and B.

Suitable methods and materials for the practice and/or testing of embodiments of a disclosed invention are described below. Such methods and materials are illustrative only and are not intended to be limiting. Other methods and materials similar or equivalent to those described herein can be used. For example, conventional methods well known in the art to which a disclosed invention pertains are described in various general and more specific references, including, for example, Sambrook et al., Molecular Cloning: A Laboratory Manual, 2d ed., Cold Spring Harbor Laboratory Press, 1989; Sambrook et al., Molecular Cloning: A Laboratory Manual, 3d ed., Cold Spring Harbor Press, 2001; Ausubel et al., Current Protocols in Molecular Biology, Greene Publishing Associates, 1992 (and Supplements to 2000); Ausubel et al., Short Protocols in Molecular Biology: A Compendium of Methods from Current Protocols in Molecular Biology, 4th ed., Wiley & Sons, 1999; Harlow and Lane, Antibodies: A Laboratory Manual, Cold Spring Harbor Laboratory Press, 1990; and Harlow and Lane, Using Antibodies: A Laboratory Manual, Cold Spring Harbor Laboratory Press, 1999.

All sequences associated with the GenBank Accession Nos. mentioned herein are incorporated by reference in their entirety as were present on Jul. 13, 2007, to the extent permissible by applicable rules and/or law.

III. Methods of Determining Molecular Interactions in Fixed Biological Samples This disclosure provides, among other things, methods for identifying protein-protein (or protein-nucleic acid) interactions in biological samples (e.g., isolated cells or tissues) that have been mounted on a solid surface (e.g., a microscope slide) and treated (e.g., formalin-fixed and paraffin-embedded ("FFPE")) to substantially maintain the positions of components (e.g., proteins, RNAs and/or DNA) within the sample relative to one another.

Molecular interactions (e.g., protein-protein interactions) previously have been studied in solution and using in vivo techniques, such as co-immunoprecipitation assays (where a protein of interest is captured with an antibody and any interaction partners bound to the protein are subsequently identified by Western blot); pull-down assays (which are similar to co-immunoprecipitation assays, but use some ligand other than an antibody to capture the protein complex); label transfer (where a known protein is tagged with a detectable label and the label is then passed to an interacting protein); in vivo crosslinking of protein complexes (where cells are grown under conditions that cause photoreactive diazirine amino acid analogs to be incorporated into cellular proteins, which diazirines can be activated and bind to interacting proteins); the yeast two-hybrid screen (which investigates the interaction between artificial fusion proteins inside the nucleus of yeast); and dual polarisation interferometry ("DPI") (which provides real-time, high-resolution measurements of molecular size, density and mass). Each of the foregoing methods requires means to isolate (whether physically, chemically or otherwise) the components having a specific interaction with one another from other non-interacting components.

Non-specific crosslinking reactions (such as, chemical crosslinking) also may be useful to examine protein-protein interactions in settings where non-specific interactions between reaction components can be controlled. However, biological samples (e.g., isolated cells or tissues) mounted on a solid surface (e.g., microscope slides or support membranes) do not offer such a setting. Under those conditions, non-specific crosslinkers bond together (permanently or semi-permanently) any components in the sample that in proximity of each other whether or not such components interact under biological conditions.

Rather than view non-specific crosslinking as a hindrance to examining protein-protein interactions, the present discovery actually exploits the non-specific crosslinking of biological components within a fixed biological sample (e.g., FFPE cells or FFPE tissues). Such crosslinking substantially ensures that the structural relationship between interacting components in the sample (e.g., protein-protein or protein-nucleic acid) is permanently or semi-permanently maintained; thereby, masking some or all residues that form the interface between the components. For example, any epitope present in the interface would not be available to a cognate antigen-binding protein (e.g., antibody) following fixation of the sample. Accordingly, the accessibility (or not) of the residues within the interface to binding proteins (e.g., antibodies) specific for such residues can be used to determine whether or not the particular components were interacting in the biological sample at the time it was fixed.

Some disclosed methods involve identifying at least two biological components (e.g., two proteins or a protein and a nucleic acid sequence) that together form a direct interaction, determining the residues (e.g., amino acids or nucleotides) involved in the interface between the at least two components, identifying or making at least one antigen-binding molecule (such as a monoclonal antibody or fragment thereof) specific for some or all of the residues involved in the interface between the at least two components, detecting in a fixed biological sample (such as FFPE tissue sections or fixed cell samples) the binding (or absence of binding) of the at least one interface-specific antigen-binding molecule. In some methods, the interacting components and the particular residues (or regions) involved in the interface between the at least two components are known; hence, identifying such components and the nature of their interface would be optional steps of the disclosed method.

Because fixation of the interface(s) between the at least two interacting components (e.g., proteins or protein and nucleic acid) leads to the exclusion of interface-specific antigen-binding molecules from binding residues in the interface(s), some methods will involve a negative result (i.e., no binding). In some such methods, it can be advantageous to further detect the presence of one or more (e.g., one or two) components of the interaction complex; thus, showing that the failure of the at least one interface-specific antigen-binding molecule(s) to bind its target(s) is not due to absence of one or more of the components involved in the making of the interface(s) but rather is due to the masking of the target(s).

Biological samples useful in a disclosed method are isolated and include any cell preparation or tissue preparation that can be fixed and mount on a solid surface. Exemplary samples include, without limitation, blood smears, cytocentrifuge preparations, cytology smears, core biopsies, fine-needle aspirates, and/or tissue sections (e.g., cryostat tissue sections and/or paraffin-embedded tissue sections). Exemplary biological samples may be isolated from normal cells or tissues, or from neoplastic cells or tissues. Neoplasia is a biological condition in which one or more cells have undergone characteristic anaplasia with loss of differentiation, increased rate of growth, invasion of surrounding tissue, and which cells may be capable of metastasis. Exemplary neoplastic cells or tissues may be isolated from solid tumors, including breast carcinomas (e.g. lobular and duct carcinomas), sarcomas, carcinomas of the lung (e.g., non-small cell carcinoma, large cell carcinoma, squamous carcinoma, and adenocarcinoma), mesothelioma of the lung, colorectal adenocarcinoma, stomach carcinoma, prostatic adenocarcinoma, ovarian carcinoma (such as serous cystadenocarcinoma and mucinous cystadenocarcinoma), ovarian germ cell tumors, testicular carcinomas and germ cell tumors, pancreatic adenocarcinoma, biliary adenocarcinoma, hepatocellular carcinoma, bladder carcinoma (including, for instance, transitional cell carcinoma, adenocarcinoma, and squamous carcinoma), renal cell adenocarcinomas, endometrial carcinomas (including, e.g., adenocarcinomas and mixed Mullerian tumors (carcinosarcomas)), carcinomas of the endocervix, ectocervix, and vagina (such as adenocarcinoma and squamous carcinoma of each of same), tumors of the skin (e.g., squamous cell carcinoma, basal cell carcinoma, melanoma, and skin appendage tumors), esophageal carcinoma, carcinomas of the nasopharynx and oropharynx (including squamous carcinoma and adenocarcinomas of same), salivary gland carcinomas, brain and central nervous system tumors (including, for example, tumors of glial, neuronal, and meningeal origin), tumors of peripheral nerve, soft tissue sarcomas and sarcomas of bone and cartilage.

A solid support useful in a disclosed method need only bear the biological sample and, optionally, but advantageously, permit the convenient detection of components (e.g., proteins and/or nucleic acid sequences) in the sample. Exemplary supports include microscope slides (e.g., glass microscope slides or plastic microscope slides), coverslips (e.g., glass coverslips or plastic coverslips), tissue culture dishes, multi-well plates, membranes (e.g., nitrocellulose or polyvinylidene fluoride (PVDF)) or BIACORE™ chips.

Fixatives for mounted cell and tissue preparations are well known in the art and include, without limitation, 95% alcoholic Bouin's fixative; 95% alcohol fixative; B5 fixative, Bouin's fixative, formalin fixative, Karnovsky's fixative (glutaraldehyde), Hartman's fixative, Hollande's fixative, Orth's solution (dichromate fixative), and Zenker's fixative (see, e.g., Carson, *Histotechology: A Self-Instructional Text*, Chicago:ASCP Press, 1997).

Biological components (e.g., proteins and/or nucleic acid sequences) that form direct interactions (such as protein-protein interactions) are known to those of ordinary skill in the art. Various exemplary protein-protein interactions can be identified in one or more of the following publicly available databases: AllFuse (European Bioinformatics Institute), Alanine Scanning Energetics DataBase (ASEdb; Harvard University), Binding Interface Database (BID; A & M University Texas); The General Repository for Interaction Datasets (BioGRID; Samuel Lunenfeld Research Institute); Biomolecular Object Network Databank (BOND; Thomson Corp.); Database of Interacting Proteins (DIP; UCLA); Genomic Knowledge Database (RIKEN, Institute of Physical and Chemical Research); HIV-1/Human Protein Interaction Database (NCBI); Human Protein Intercation Database (HPID; Inha University); Human Protein Reference Database (Johns Hopkins University and The Institute of Bioinformatics, India); Inter-Chain Beta-Sheets database (ICBS; University of California); Kinetic Data of Bio-molecular Interactions (KDBI; National University of Singapore); Biomolecular Relations in Information Transmission and Expression (KEGG BRITE; Kyoto University); Molecular INTeractions database (MINT; CBM, Rome); Mammalian Protein-Protein Interaction database (MPPI; MIPS); PDZ-Base (Weill Medical College of Cornell University); POINT (National Health Research Institutes & National Taiwan University); Protein Interactions and Molecular Information databasE (PRIME; Human Genome Center, University of Tokyo); Protein Interaction Database (Protein Lounge); SNAPPIView (University of Dundee).

Some of the foregoing databases further identify the residues or regions of the applicable proteins involved in the protein-protein interface. Alternatively, residues or regions involve in a protein-protein interaction can be determined using any technique known to the ordinarily skilled artisan; for example, peptide competition studies (where a peptide having a sequence corresponding to residues believed to be involved in a protein-protein interface is used to competitively inhibit the protein-protein interaction; successful inhibition by the peptide of the interaction indicates that the subject sequence likely is involved in the protein-protein interaction), or mutational analysis of one or both components of the protein-protein interaction.

Once a region or residues of an interface between directly interacting proteins (or a protein and nucleic acid sequence) is known or determined, a binding molecule that specifically recognizes the interface region or an epitope consisting of interface residues (i.e., an interface-specific binding molecule) can be obtained from a commercially available source or prepared using techniques common in the art. For example, methods of preparing antibodies, antibody fragments, aptamers and other antigen-binding molecules are described in detail elsewhere in this disclosure.

Particular method embodiments involve detecting in a fixed biological sample a protein complex including (or consisting of) EGFR and an EGFR-interacting protein (e.g., a regulatory protein, such as a SOCS protein like SOCS1 or SOCS3). EGFR is known to form protein-protein interactions in vivo and in vitro with numerous other proteins. Some such interactions are listed in Table 1.

TABLE 1

Exemplary EGFR Interaction Partners

| PARTNER 1 | PARTNER 2 | SYSTEM | SOURCE | PUBMED ID |
|---|---|---|---|---|
| AREG | EGFR | In vivo | Wong L et al. | 10085134 |
| CD44 | EGFR | In vivo | Tsatas D et al. | 12093135 |
| EGFR | GRB2 | In vivo | Lowenstein EJ et al. | 1322798 |
| EGFR | GRB2 | In vivo | Okutani T et al. | 7527043 |
| EGFR | GRB2 | In vitro | Lowenstein EJ et al. | 1322798 |
| EGFR | GRB2 | In vitro | Okutani T et al. | 7527043 |
| EGFR | CTNNB1 | In vivo | Takahashi K et al. | 9233779 |
| EGFR | CDC25A | In vivo | Wang Z et al. | 11912208 |
| EGFR | CDC25A | In vitro | Wang Z et al. | 11912208 |
| DCN | EGFR | In vivo | Santra M et al. | 12105206 |
| DCN | EGFR | In vivo | Iozzo RV et al. | 9988678 |
| DCN | EGFR | In vitro | Santra M et al. | 12105206 |
| DCN | EGFR | In vitro | Iozzo RV et al. | 9988678 |
| DCN | EGFR | Two-hybrid | Santra M et al. | 12105206 |
| DCN | EGFR | Two-hybrid | Iozzo RV et al. | 9988678 |
| EGFR | HBEGF | In vivo | Shin SY et al. | 12725245 |
| EGF | EGFR | In vitro | Stortelers C et al. | 12093292 |
| EGFR | CAV1 | In vivo | Couet J et al. | 9374534 |
| EGFR | CAV1 | In vitro | Couet J et al. | 9374534 |
| EGFR | PRKACA | In vivo | Tortora G et al. | 9050991 |
| EGFR | ERBB3 | In vivo | Marques MM et al. | 10527633 |
| EGFR | SHC1 | In vivo | Sakaguchi K et al. | 9544989 |
| ITGA5 | EGFR | In vitro | Kuwada SK et al. | 10888683 |
| ITGA5 | EGFR | In vivo | Kuwada SK et al. | 10888683 |
| EGFR | ZNF259 | In vivo | Moores SL et al. | 10938113 |
| EGFR | RASA1 | In vivo | Serth J et al. | 1633149 |
| PTK2 | EGFR | In vivo | Sieg DJ et al. | 10806474 |
| PTK2 | EGFR | In vitro | Sieg DJ et al. | 10806474 |
| PLSCR1 | EGFR | In vivo | Sun J et al. | 12009895 |
| PLSCR1 | EGFR | In vivo | Nanjundan M et al. | 12871937 |
| PLSCR1 | EGFR | In vitro | Sun J et al. | 12009895 |
| PLSCR1 | EGFR | In vitro | Nanjundan M et al. | 12871937 |
| GRB14 | EGFR | In vivo | Daly RJ et al. | 8647858 |
| GRB14 | EGFR | In vitro | Daly RJ et al. | 8647858 |
| EGFR | DOK2 | In vivo | Jones N et al. | 10508618 |
| KRT7 | EGFR | In vivo | Blagoev B et al. | 12577067 |
| KRT7 | EGFR | In vitro | Blagoev B et al. | 12577067 |
| TGFA | EGFR | In vitro | Garrett TP et al. | 12297049 |
| EGFR | XRCC6 | In vivo | Bandyopadhyay D et al. | 9430697 |
| EGFR | PLD2 | In vitro | Slaaby R et al. | 9837959 |
| EGFR | PLD2 | In vivo | Slaaby R et al. | 9837959 |
| CD82 | EGFR | In vivo | Odintsova E et al. | 10985391 |
| CD82 | EGFR | In vitro | Odintsova E et al. | 10985391 |
| SNX6 | EGFR | In vivo | Parks WT et al. | 11279102 |
| SNX6 | EGFR | In vitro | Parks WT et al. | 11279102 |
| EGFR | PTK2B | In vivo | Keely SJ et al. | 10777553 |
| GRB10 | EGFR | In vivo | Frantz JD et al. | 9006901 |
| GRB10 | EGFR | In vivo | He W et al. | 9506989 |
| GRB10 | EGFR | In vitro | Frantz JD et al. | 9006901 |
| GRB10 | EGFR | In vitro | He W et al. | 9506989 |
| PRKCA | EGFR | In vivo | Gauthier ML et al. | 12878187 |
| PRKCA | EGFR | In vitro | Gauthier ML et al. | 12878187 |
| EGFR | STAT1 | In vivo | Xia L et al. | 12070153 |
| EGFR | STAT1 | In vitro | Xia L et al. | 12070153 |
| KRT18 | EGFR | In vivo | Blagoev B et al. | 12577067 |
| KRT18 | EGFR | In vitro | Blagoev B et al. | 12577067 |
| EGFR | SOCS3 | In vivo | Xia L et al. | 12070153 |
| EGFR | SOCS3 | In vitro | Xia L et al. | 12070153 |
| EGFR | MIG-6 | In vivo | Hackel PO et al. | 11843178 |
| EGFR | MIG-6 | Two-hybrid | Hackel PO et al. | 11843178 |
| EGFR | SOCS1 | In vivo | Xia L et al. | 12070153 |
| PLEC1 | EGFR | In vivo | Blagoev B et al. | 12577067 |
| PLEC1 | EGFR | In vitro | Blagoev B et al. | 12577067 |
| EGFR | SNX4 | In vivo | Haft CR et al. | 9819414 |
| EGFR | PRKAR1A | In vivo | Tortora G et al. | 9050991 |
| AMH | EGFR | In vivo | Maggard MA et al. | 8596488 |
| EGFR | MAP4K1 | In vivo | Anafi M et al. | 9346925 |
| PLCG1 | EGFR | In vivo | Bedrin MS et al. | 9207933 |
| SNX1 | EGFR | In vivo | Haft CR et al. | 9819414 |
| SNX1 | EGFR | In vivo | Kurten RC et al. | 8638121 |
| SNX1 | EGFR | Two-hybrid | Haft CR et al. | 9819414 |
| SNX1 | EGFR | Two-hybrid | Kurten RC et al. | 8638121 |
| EGFR | STAT5B | In vivo | Runge DM et al. | 10558875 |
| DEGS1 | EGFR | In vivo | Cadena DL et al. | 9188692 |
| DEGS1 | EGFR | In vitro | Cadena DL et al. | 9188692 |
| DEGS1 | EGFR | Two-hybrid | Cadena DL et al. | 9188692 |
| EGFR | PIK3C2B | In vitro | Wheeler M et al. | 11533253 |
| KRT17 | EGFR | In vivo | Blagoev B et al. | 12577067 |
| KRT17 | EGFR | In vitro | Blagoev B et al. | 12577067 |
| RGS16 | EGFR | In vivo | Derrien A et al. | 11602604 |
| HD | EGFR | In vivo | Liu YF et al. | 9079622 |
| PITPNA | EGFR | In vivo | Kauffmann-Zeh A et al. | 7761838 |
| PITPNA | EGFR | In vitro | Kauffmann-Zeh A et al. | 7761838 |
| EGFR | CEBPB | In vivo | Harmon AW et al. | 12095417 |
| EGFR | CEBPB | In vitro | Harmon AW et al. | 12095417 |
| MUC1 | EGFR | In vivo | Li Y et al. | 11483589 |
| MUC1 | EGFR | In vivo | Schroeder JA et al. | 11278868 |
| NCK2 | EGFR | In vivo | Chen M et al. | 9737977 |
| NCK2 | EGFR | In vivo | Li W et al. | 1333047 |
| EGFR | PTK6 | In vivo | Kamalati T et al. | 8940083 |
| EGFR | CAV3 | In vivo | Couet J et al. | 9374534 |
| EGFR | CAV3 | In vitro | Couet J et al. | 9374534 |
| EGFR | CRK | In vivo | Hashimoto Y et al. | 9642287 |
| EGFR | CRK | In vitro | Hashimoto Y et al. | 9642287 |
| EGFR | GRB7 | In vivo | Tanaka S et al. | 9710451 |
| EGFR | GRB7 | In vitro | Tanaka S et al. | 9710451 |
| EGFR | SNRPD2 | In vivo | Blagoev B et al. | 12577067 |
| EGFR | SNRPD2 | In vitro | Blagoev B et al. | 12577067 |
| EGFR | SRC | In vitro | Sato K et al. | 10971656 |
| CBLB | EGFR | In vivo | Ettenberg SA et al. | 10086340 |
| CBLB | EGFR | In vitro | Ettenberg SA et al. | 10086340 |
| EGFR | CBLC | In vivo | Keane MM et al. | 10362357 |
| EGFR | CBLC | In vitro | Keane MM et al. | 10362357 |
| EGFR | SHC1 | In vitro | Blagoev B et al. | 12577067 |
| EGFR | PTPN6 | In vivo | Keilhack H et al. | 9733788 |
| EGFR | PTPN6 | In vitro | Keilhack H et al. | 9733788 |
| EPS8 | EGFR | In vivo | Castagnino P et al. | 7532293 |
| EPS8 | EGFR | In vivo | Di Fiore PP et al. | 12127568 |
| SNX2 | EGFR | In vivo | Haft CR et al. | 9819414 |
| SNX2 | EGFR | In vitro | Haft CR et al. | 9819414 |
| TNC | EGFR | In vivo | Swindle CS et al. | 11470832 |
| TNC | EGFR | In vitro | Swindle CS et al. | 11470832 |
| EGFR | CAMLG | In vivo | Tran DD et al. | 12919676 |
| EPPK1 | EGFR | In vivo | Blagoev B et al. | 12577067 |
| EPPK1 | EGFR | In vitro | Blagoev B et al. | 12577067 |
| EGFR | NCK1 | In vitro | Tang J et al. | 9362449 |
| KRT8 | EGFR | In vivo | Blagoev B et al. | 12577067 |
| KRT8 | EGFR | In vitro | Blagoev B et al. | 12577067 |
| EGFR | TJP1 | In vivo | Kaihara T et al. | 12708492 |
| VAV1 | EGFR | In vivo | Moores SL et al. | 10938113 |
| EGFR | STAT5A | In vivo | Olayioye MA et al. | 10358079 |
| EGFR | GAB1 | In vivo | Kameda H et al. | 11432805 |
| EGFR | TNK2 | In vivo | Manser E et al. | 8497321 |
| EGFR | TNK2 | In vitro | Satoh T et al. | 8647288 |
| EGFR | VAV2 | In vivo | Pandey A et al. | 10618391 |
| EGFR | VAV2 | In vivo | Moores SL et al. | 10938113 |
| EGFR | VAV2 | In vitro | Pandey A et al. | 10618391 |
| EGFR | VAV2 | In vitro | Moores SL et al. | 10938113 |
| SOS1 | EGFR | In vivo | Qian X et al. | 9447973 |
| EGFR | MAP3K14 | In vivo | Habib AA et al. | 11116146 |
| EGFR | ESR1 | In vivo | Marquez DC et al. | 11887937 |
| EGFR | ERBB2 | In vivo | Brockhoff G et al. | 11500850 |
| EGFR | ERBB2 | In vitro | Brockhoff G et al. | 11500850 |
| SH2D3A | EGFR | In vivo | Lu Y et al. | 10187783 |
| CDH1 | EGFR | In vivo | Pece S et al. | 10969083 |
| EGFR | PTPN1 | In vivo | Zhang ZY et al. | 8621392 |
| EGFR | PTPN1 | In vivo | Jia Z et al. | 7540771 |
| EGFR | PTPN1 | In vivo | Sarmiento M et al. | 10889023 |
| EGFR | PTPN1 | In vivo | Li S et al. | 12573287 |
| EGFR | PTPN1 | In vitro | Zhang ZY et al. | 8621392 |

TABLE 1-continued

Exemplary EGFR Interaction Partners

| PARTNER 1 | PARTNER 2 | SYSTEM | SOURCE | PUBMED ID |
|---|---|---|---|---|
| EGFR | PTPN1 | In vitro | Jia Z et al. | 7540771 |
| EGFR | PTPN1 | In vitro | Sarmiento M et al. | 10889023 |
| EGFR | PTPN1 | In vitro | Li S et al. | 12573287 |
| VAV3 | EGFR | In vivo | Zeng L et al. | 11094073 |
| INPPL1 | EGFR | In vitro | Pesesse X et al. | 11349134 |
| INPPL1 | EGFR | In vivo | Pesesse X et al. | 11349134 |
| EPS15 | EGFR | In vivo | van Delft S et al. | 9049247 |
| EGFR | ARF4 | In vitro | Kim SW et al. | 12446727 |
| EGFR | ARF4 | In vivo | Kim SW et al. | 12446727 |
| EGFR | ARF4 | Two-hybrid | Kim SW et al. | 12446727 |
| EGFR | GNAI2 | In vivo | Zhang BH et al. | 11286993 |
| EGFR | PDGFRB | In vivo | Habib AA et al. | 9506992 |
| SHC3 | EGFR | In vivo | Nakamura T et al. | 9507002 |
| EGFR | BTC | In vivo | Mixan B et al. | 9528863 |
| EGFR | SOS2 | In vivo | Qian X et al. | 10675333 |
| NRG1 | EGFR | In vitro | Pinkas-Kramarski R et al. | 8702572 |
| EGFR | CASP1 | In vivo | Bae SS et al. | 11226410 |
| EGFR | CASP1 | In vivo | Bae SS et al. | 11226410 |
| EGFR | EREG | In vivo | Komurasaki T et al. | 9419975 |
| EGFR | PTPN11 | In vitro | Tomic S et al. | 7673163 |
| EGFR | PTPN11 | In vivo | Tomic S et al. | 7673163 |
| PTPRJ | EGFR | In vivo | Jallal B et al. | 9115287 |
| EGFR | RIPK1 | In vivo | Habib AA et al. | 11116146 |
| FER | EGFR | In vivo | Kim L et al. | 7623846 |

Protein-protein interactions typically influence the activity of one or both interacting partners. For example, a protein-protein interaction may result in the negative regulation (e.g., inhibition) of one or both partners, or may result in the positive regulation (e.g. activation) of one or both partners. Other functional outcomes also are possible. Exemplary negative regulators of EGFR that form protein-protein interactions with EGFR include, for instance, SOCS1, SOCS3, SOCS5, and C-CBL. Exemplary positive regulators of EGFR that form protein-protein interactions with EGFR include, for instance, STAT1, STAT5B, GRB7, HER2, and MUC1.

Methods useful for detection of a protein-protein interaction using an interface-specific binding molecule (such as an antibody, antibody fragment, recombinant antibody, scaffold polypeptide with antibody binding sites, and/or an aptamer) are well known in the art. In some examples, a fixed biological sample is contacted with an interface-specific binding molecule under conditions that permit (or would permit if it was accessible) binding of the interface-specific binding molecule to its epitope in the interface between the interacting proteins. Optionally, a control reaction is performed (e.g., simultaneous with, prior to, or following) to ensure that the conditions are suitable for the detection reaction to occur. For example, the biological sample (or a serial section or a parallel-prepared cell sample) also may be contacted with a control antigen-binding molecule (such as, an antibody, antibody fragment, recombinant antibody, scaffold polypeptide with antibody binding sites, and/or an aptamer). The control antigen-binding molecule specifically binds to a non-interacting component of the sample (i) that is not involved in the protein-protein complex of interest and (ii) the epitope of which is known to be present and detectable in the sample under the particular detection conditions.

In exemplary methods, an interface-specific binding molecule and an optional control antigen-binding molecule are antibodies (e.g., monoclonal antibodies) or antibody fragments. Detection of such antibodies or antibody fragments is performed by immunostaining, such as illustrated in FIG. 1, which is a standard technique in the art. Detection may by direct or indirect. With direct detection, primary antibodies (i.e., the antibodies that specifically bind to biological component(s) of interest in the sample) are directly labeled, for instance, with a detectable moiety or with an enzyme that catalyzes a reaction leading to a detectable product. With indirect detection, one or more secondary reagents (such as secondary, tertiary, etc. antibodies) are used to detect the primary antibody (and, as applicable, secondary or subsequent antibodies) and the last of such reagents is detectable, for instance by labeling with detectable moiety or with an enzyme that catalyzes a reaction leading to a detectable product. Representative immunostaining procedures are provided in the Examples.

Figure 2:
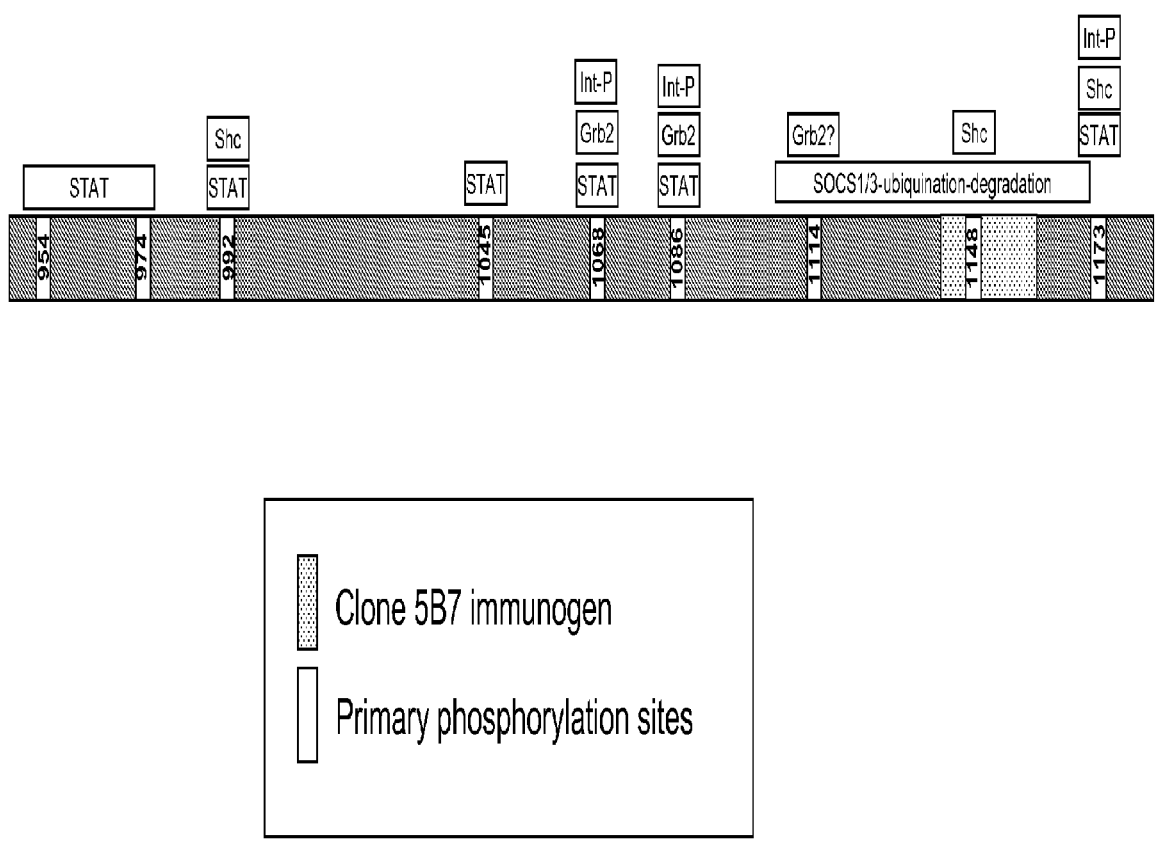
FIG. 2 is a schematic representation of the EGFR regulatory domain showing the locations of autophosphorylation sites (white boxes with number indicating position of autophosphorylated amino acid residue) and known binding sites for exemplary EGFR regulatory proteins, including Signal Transducer and Activator of Transcription (STAT) proteins (e.g., STAT1 and/or STAT3; OMIM Accession Nos. 600555 or 102582), Growth Factor Receptor-Bound Protein 2 (Grb2; OMIM Accession No. 108355), Signaling and Transforming Protein Containing Src Homology 2 and 3 Domains (Shc) (e.g., OMIM Accession Nos. 600560, 605217, or 605263), Int-P, and Suppressor of Cytokine Signaling proteins (e.g., SOCS1 and/or SOCS3; OMIM Accession Nos. 603597 and 604176, respectively).

Some disclosed methods involve dual detection of an external domain epitope present on EGFR and an internal domain (or regulatory domain) epitope of EGFR. The EGFR regulatory domain has multiple binding sites for regulatory proteins (see, e.g., FIG. 2). Accordingly, epitopes in the EGFR regulatory domain may not be accessible in fixed biological samples where, at the time of fixation, EGFR was involved in a protein-protein interaction with one or more of its regulatory proteins (such as a SOCS protein, e.g., SOCS1 or SOCS3). In comparison, the EGFR external domain functions primary as a ligand-binding domain, and, typically, it is not masked from antibodies specific for external domain epitopes. Accordingly, in some methods, an antigen-binding molecule specific for the EGFR external domain (anti-EGFR external domain antibody or fragment thereof) can serve as a control for an antigen-binding molecule specific for a (potentially masked) epitope in an EGFR-regulatory protein interface. One caveat of interest is that EGFR may "shed" its external domain or may be mutant and lack its external domain (Pedersen et al., *Ann. Oncol.*, 6:745, 2001). Under those circumstances, an antigen-binding molecule specific for the EGFR external domain (e.g., anti-EGFR external domain antibody or fragment thereof) would have no target to bind and, therefore, would not be detected. This circumstance (and useful information that can be gleaned from such circumstance) is discussed in detail elsewhere in this disclosure.

Some of the foregoing method embodiments and other method embodiments in this disclosure involve substantially no specific binding of a RD-binding molecule (such as a monoclonal antibody) to its epitope (e.g., which is located in the protein-protein interface between EGFR and it regulatory molecule(s)). Substantially no binding can be determined by any method available to those of ordinary skill in the art. For example, substantially no binding of a RD-binding molecule may be relative to the binding of the same RD-binding molecule under substantially the same conditions in another sample in which the epitope of the RD-binding molecule is known to be accessible. In another example, substantially no binding of a RD-binding molecule may mean that the detection means (e.g., detectable label or colorimetric reagent) used to visualize the specific binding of the RD-binding molecule can not be seen under ordinary circumstances for such detection, e.g., under a light or fluorescence microscope with 4×, 10×, or 40× magnification. In still another example, substantially no binding of a RD-binding molecule means that the RD-binding molecule has less than about 25% (such as less than about 20%, less than about 15%, less than about 10%, less than about 5%, or less than about 1%) its binding under control circumstances (e.g., in a tissue or cell sample where its epitope is known to be accessible).

IV. Predictive Methods

The discovery herein of methods to detect EGFR molecular interactions in fixed biological samples opens the way to predicting EGFR status and important corollaries in such samples or in subjects from which such samples are collected; for example, in neoplastic tissues and/or cells where EGFR overexpression is believed to play an important role in tumorigenesis (e.g., Arnold et al., *Oncologist*, 6:602, 2006) and/or in cancer patients. The disclosed predictive methods are applicable to any type of cancer or to a subject with any type of cancer, for instance EGFR-expressing (or -overexpressing) cancers. Exemplary neoplasms useful in all disclosed methods (including predictive methods) are described elsewhere in this disclosure (e.g., Section III and the Examples). Particular predictive method embodiments involve lung cancer (e.g., non-small cell lung cancer), ovarian cancer, colorectal cancer, liver cancer, head and neck, prostate, and/or glioblastoma and/or subjects having any of such cancers.

A. Predicting Aggressiveness of EGFR-Positive Neoplasms

Detection of a direct (e.g., protein-protein) interaction between EGFR and a negative regulator of EGFR function (e.g., a SOCS protein, such as SOCS1 or SOCS3, or SOCS5) predicts inhibition of EGFR function in that biological sample. Inhibition of EGFR function has important consequences in many cells and tissues. For example, in neoplastic cells and tissues where EGFR overexpression is believed to play a role in tumorigenesis (e.g., Arnold et al., *Oncologist*, 6:602, 2006), detection of a direct interaction between EGFR and a negative regulator of EGFR function (e.g., a SOCS protein, such as SOCS1 or SOCS3) further predicts that a neoplasm may be less aggressive (e.g., less rapidly growing, and/or less likely to metastasize). A better prognosis (independent of therapy) for a subject with such a neoplasm also may be predicted.

On the other hand, detection of a direct interaction between EGFR and a positive regulator of EGFR function (e.g., STAT1, STAT5B, GRB7, HER2, and/or MUC1) predicts activation of EGFR function in that biological sample (e.g., neoplastic tissue or cells). For the opposite of reasons discussed above, a worse prognosis (independent of therapy) for a subject with such a neoplasm also may be predicted.

A less-aggressive tumor can be characterized by any parameters known in the art, including, for instance, decreased growth rate (e.g., increased rate of apoptosis and/or decreased rate of cell division), decreased rate of metastasis, and/or increased sensitivity to chemotherapy.

Prognosis for a subject can be characterized by any parameter known in the art, including, for instance, actual survival after initial diagnosis (such as 6-month survival, 1-year survival, 2-year survival, or 5-year survival), and/or actual survival relative to the average survival for similarly situated patients. A better prognosis entails, e.g., survival of a patient for more than 1 year after initial diagnosis (such as more than 2 years or more than 5 years), or survival of a patient for more than 6 months longer (e.g., more than 1 year longer, more than 2 years longer, more than 5 years longer) than the average survival for similarly situated. A worse prognosis entails, e.g., survival of a patient for less than 5 years after initial diagnosis (such as less than 2 years or less than 1 years), or survival of patient less than the average survival for similarly situated patients (such as, about 3 months less than average survive, about 6 months less than average survive, or about 1 year less than average survival).

Figure 3:
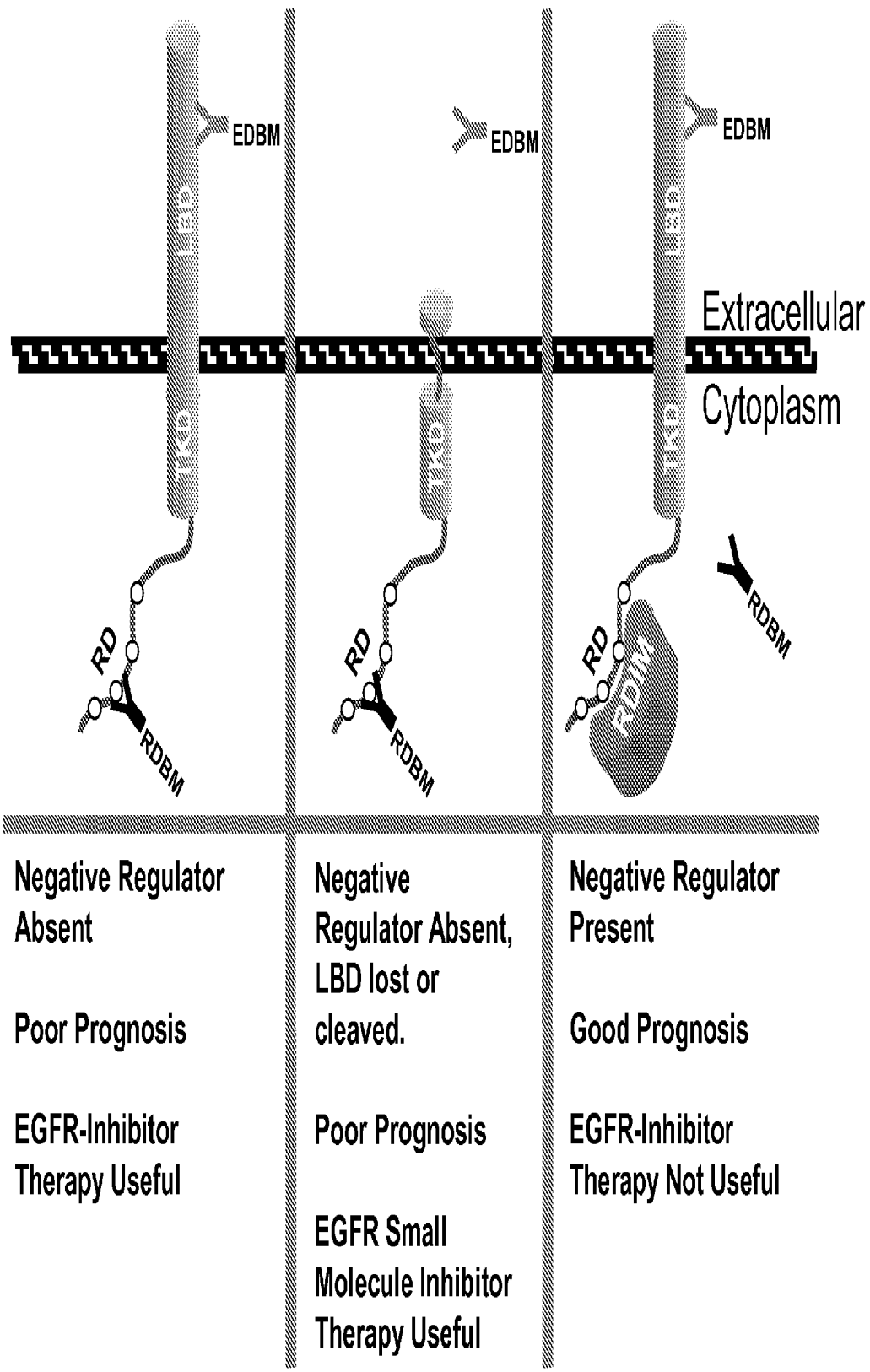
FIG. 3 is a series of schematic representations involving the EGFR molecule which, in its wild-type state, has an extracellular ligand-binding domain (LBD) and intracellular tyrosine kinase (TKD) and regulatory (RD) domains. In each schematic, as applicable, EDBM represents an extracellular-domain-specific binding molecule (such as an antibody); RDBM represents a regulatory-domain-specific binding molecule (such as an antibody); and RDIM represents a regulatory domain inhibitory molecule (such as a SOCS protein like SOCS1 or SOCS3). Each of the three schematics (from left to right) represents a different molecular setting. The left-most panel shows a full-length EGFR not associated with a RDIM. The center panel shows a constitutively active N-terminal truncated EGFR mutant. The right-most panel shows a full-length EGFR associated with a RDIM. In each case, predictions based on the binding (or not) of the EDBM and RDBM are listed below the molecular schematic.

Exemplary prognoses based on detecting an interaction (or lack of interaction) between EGFR and, e.g., a negative regulator that binds the EGFR regulatory domain (such as a SOCS protein like SOCS1 and/or SOCS3) are shown schematically in FIG. 3.

B. Predicting Responsiveness of a Cancer Patient to EGFR-Inhibitor Therapy

Methods of detecting an interaction (or lack of interaction) between EGFR and, e.g., its negative regulator(s) (such as a SOCS protein like SOCS1 and/or SOCS3) enables a variety of predictions with respect to the outcome of EGFR inhibitor therapy in a cancer patient. EGFR inhibitor therapies include at least two drug classes: EGFR antibody therapies (such as, cetuximab (Erbitux™), panitumumab (Vectibix™), IMC-11F8 (Imclone), matuzumab (Merck_KGA)) and tyrosine kinase inhibitors ("TKIs") (such as gefitinib (Iressa™), erlotinib (Tarceva™), lapatinib ditosylate (GlaxoSmithKline), HKI-272 (Wyeth), AEE788 (Novartis), vandetanib (Zactima™; Astrazeneca), XL647 (Exelixis), BMS-599626 (Bristol-Myers Squibb), BIBW 2992 (Boehringer Ingelheim)). EGFR antibody therapies typically are directed to the EGFR external domain and block binding of an EGFR ligand (such as EGF) to the receptor; thereby, inhibiting EGFR activation. TKIs work by inhibiting the intracellular kinase domain of EGFR, which also inhibits EGFR activation.

Some method embodiments involve one or both of the foregoing classes of EGFR inhibitors. Particular method embodiments involve predicting the response of cancer patients to cetuximab (Erbitux™), panitumumab (Vectibix™), gefitinib (Iressa™), or erlotinib (Tarceva™), or any combination thereof (such as, cetuximab (Erbitux™) or panitumumab (Vectibix™), gefitinib (Iressa™) or erlotinib (Tarceva™), or cetuximab (Erbitux™), panitumumab (Vectibix™), gefitinib (Iressa™) or erlotinib (Tarceva™)).

Exemplary predictions based on detecting an interaction (or lack of interaction) between EGFR and, e.g., a negative regulator that binds the EGFR regulatory domain (such as a SOCS protein like SOCS1 and/or SOCS3) are provided in Table 2 and shown schematically in FIG. 3.

TABLE 2

Exemplary Predicted Therapeutic Response

| | ID-Binding Molecule | ED-Binding Molecule | EGFR Implication | Therapeutic | Predicted Therapeutic Response |
|---|---|---|---|---|---|
| 1 | Positive | Positive | EGFR is present RDIM (e.g. SOCS3) is absent | ED-based therapy (e.g., EGFR Ab) ID-based therapy (e.g., TKI) | Sensitive Sensitive |
| 2 | Negative | Positive | EGFR is present RDIM (e.g. SOCS3) is present | ED-based therapy (e.g., EGFR Ab) ID-based therapy (e.g., TKI) | Resistant Resistant |
| 3 | Positive | Negative | Mutant/Cleaved EGFR is present | ED-based therapy (e.g., EGFR Ab) | Resistant |

TABLE 2-continued

Exemplary Predicted Therapeutic Response

| | ID-Binding Molecule | ED-Binding Molecule | EGFR Implication | Therapeutic | Predicted Therapeutic Response |
|---|---|---|---|---|---|
| | | | RDIM (e.g. SOCS3) is absent | ID based therapy (e.g., TKI) | Sensitive |
| 4 | Negative | Negative | EGFR is absent | ED-based therapy (e.g., EGFR Ab) | No Response |
| | | | | ID-based therapy (e.g., TKI) | No Response |

ID = EGFR internal (or regulatory) domain;
ED = EGFR extracellular domain;
RDIM = regulatory domain inhibitory molecule;
Ab = antibody (e.g., monoclonal or otherwise engineered antibody)

In one method embodiment, an interaction between the internal regulatory domain of EGFR and its negative regulator (e.g., a SOCS protein, such as SOCS1 and/or SOCS3) is detected (e.g., by masking of the epitope of an interface-specific binding molecule (such as a monoclonal antibody, including clone 5B7 (see, e.g., Examples)). Optionally, but advantageously, the presence of full-length (or substantially full-length) EGFR also is detected using an antigen-binding molecule (e.g., monoclonal antibody, including clone 3C6) specific for the EGFR external domain. In this example, the interface-specific binding molecule (e.g., clone 5B7) is excluded from its binding site and, therefore, is not detected, while the external-domain antigen-binding molecule (e.g., clone 3C6) binds to its epitope and is detected. These circumstances support a prediction that a therapy designed to inhibit EGFR function likely would not be effective or would be less effective than in the absence of the negative regulator. That is (solely for illustration purposes (and not to be limited by mechanism or implication of a mechanism)): Providing an EGFR inhibitor to a subject in which EGFR function already was inhibited may be analogous to applying the brakes in a car that is already at a stop.

In another method embodiment, an interaction between the internal regulatory domain of EGFR and its negative regulator (e.g., a SOCS protein, such as SOCS1 and/or SOCS3) is lacking (e.g., as demonstrated by the binding to EGFR of an interface-specific binding molecule (such as a monoclonal antibody, including clone 5B7 (see, e.g., Examples)) to its epitope, which would otherwise be masked by the EGFR-negative regulator interaction). Optionally, but advantageously, the presence of the EGFR external domain (i.e., full-length or substantially full-length EGFR) also is detected using an antigen-binding molecule (e.g., monoclonal antibody, including clone 3C6) specific for that domain. In this example, the interface-specific binding molecule (e.g., clone 5B7) specifically binds its epitope in the EGFR regulatory domain and, therefore, is detected, and the external-domain antigen-binding molecule (e.g., clone 3C6) also binds to its epitope and is detected. These circumstances support a prediction that a therapy designed to inhibit EGFR function likely would be effective or would be more effective than in the presence of the negative regulator.

In still another method embodiment, an interaction between the internal regulatory domain of EGFR and its negative regulator (e.g., a SOCS protein, such as SOCS1 and/or SOCS3) is lacking (e.g., as demonstrated by the binding to EGFR of an interface-specific binding molecule (such as a monoclonal antibody, including clone 5B7 (see, e.g., Examples)) to its epitope, which would otherwise be masked by the EGFR-negative regulator interaction). Optionally, but advantageously, the presence or absence of the EGFR external domain (i.e., full-length or substantially full-length EGFR) also is detected using an antigen-binding molecule (e.g., monoclonal antibody, including clone 3C6) specific for that domain. In this example, the interface-specific binding molecule (e.g., clone 5B7) specifically binds its epitope in the EGFR regulatory domain and, therefore, is detected; however, it also is determined that the EGFR external domain is lacking (e.g., a mutant or N-terminal truncated EGFR) by failure to bind of an antigen-binding molecule specific for that domain (e.g., monoclonal antibody, including clone 3C6). These circumstances support a prediction that an antibody therapy designed to inhibit EGFR function by blocking ligand binding to the EGFR external domain likely would be not effective because such domain is lacking On the other hand, these circumstances further support a prediction that a TKI therapy, which inhibits the tyrosine kinase activity localized in the EGFR intracellular domain, likely would be effective or would be more effective than in the presence of the negative regulator.

The response of a subject to EGFR inhibitor therapy can be measured by any relevant parameter known in the art. In some method embodiments, a subject response is cessation or slowing of tumor growth (as measured, for example, by tumor size), decrease in tumor cell proliferation, increase in tumor cell apoptosis, and/or decreased level of relevant tumor marker(s). In other method embodiments, a subject response is at least a 50% slowing of tumor growth or tumor cell proliferation as compared to pre-treatment growth (such at least a 40% slowing, at least a 30% slowing, at least a 20% slowing, or at least a 10% slowing). In other method embodiments, a subject response is at least a 50% increase in tumor cell apoptosis as compared to pre-treatment levels (such at least a 40% increase, at least a 30% increase, at least a 20% increase, or at least a 10% increase).

V. EGFR Regulatory Domain Peptides

This disclosure concerns, among other things, the discovery of a 19-amino acid region of EGFR that can be used, e.g., to interrogate the structural and/or functional state of the receptor. This region has the sequence: LDNPDYQQDFFP-KEAKPNG (SEQ ID NO: 2; "L2G Peptide"). It is found in the C-terminal, intracellular (or cytoplasmic) domain of EGFR (for exemplary EGFR sequences, see, e.g., GEN-BANK™ Accession Nos. XP_001156546.1; XP_001156495.1; XP_519102.2; XP_001156439.1; BAD92679.1; AAS07524.1; AAX41033.1; NP_113695.1;

AAT52212.1; NP_005219.2; and CAA25240.1, wherein the sequence present on Jul. 13, 2007 is herein incorporated by reference).

The intracellular domain of EGFR, which corresponds to residues 669-1210 of SEQ ID NO: 1, includes a kinase domain (residues 712-979 of SEQ ID NO: 1) and a regulatory domain (residues 980-1210). The EGFR regulatory domain includes at least five tyrosine residues (Tyr1016, Tyr1092, Tyr1110, Tyr1172, and Tyr1197 of SEQ ID NO: 1), which are believed to be autophosphorylation sites (Chattopadhyay et al., *J. Biol. Chem.*, 274:26091-7, 1999). Among all of the C-terminal tyrosine residues, there are three YXXL/V (SEQ ID NO: 4) and four YXXP/D (SEQ ID NO: 5) motifs, which, for many transmembrane receptors, serve as the docking sites for Src homology 2 (SH2) domain-containing proteins (Xia et al., *J. Biol. Chem.*, 277(34):30716-23, 2002). As a class, SH2 domain-containing proteins are accepted phosphorylation-dependent regulators of intracellular signal cascades.

The EGFR regulatory domain contains an inhibitory subdomain (Xia et al., *J. Biol. Chem.*, 277(34):30716-23, 2002), which corresponds to residues 1138-1196 of SEQ ID NO: 1. The L2G Peptide sequence is contained within this inhibitory subdomain. The inhibitory subdomain is believed at least to mediate a protein-protein interaction between EGFR and SOCS proteins (e.g., SOCS1 and SOCS3) (Xia et al., *J. Biol. Chem.*, 277(34):30716-23, 2002). The interaction between EGFR and SOCS proteins is further believed to stimulate the proteasomal degradation of the EGFR complex and/or induce degradation of EGFR-associated STAT proteins and/or block EGFR from further recruitment and activation of STAT proteins (Xia et al., *J. Biol. Chem.*, 277(34):30716-23, 2002). In each instance, the SOCS protein (e.g., SOCS1 and/or SOCS3) interaction directly or indirectly inhibits EGFR activity.

As demonstrated in this disclosure, epitopes present in the L2G Peptide sequence of EGFR are inaccessible to cognate RD-binding molecules (e.g., antibodies) in some normal or neoplastic tissues. The accessibility of such epitope is restored in tissues that lack proteins that normally bind the EGFR regulatory domain and the EGFR inhibitory subdomain. Hence, the disclosed L2G Peptide and other RDPs derived therefrom are useful, at least, to make RD-binding molecules (such as antibodies, antibody fragments, scaffold polypeptides including antibody binding domains and aptamers) that expose the structural and corresponding functional states of EGFR.

In one embodiment, a disclosed RDP is the L2G Peptide, which has the sequence LDNPDYQQDFFPKEAKPNG (SEQ ID NO: 2). Also contemplated in some embodiments are immunogenic fragments of the L2G Peptide, which fragments can be useful for producing a disclosed RD-binding molecule. For example, as demonstrated in Example 4, at least the subsequence QQDFFPK (residues 7-13 of SEQ ID NO: 2) is sufficient to produce a disclosed RD-binding molecule (e.g., monoclonal antibody). Thus, in some embodiments, an immunogenic fragment of SEQ ID NO: 2 is at least 7 contiguous residues of SEQ ID NO: 2 and includes the sequence QQDFFPK (residues 7-13 of SEQ ID NO: 2). In more specific embodiments an immunogenic fragment of SEQ ID NO: 2 is between 7 and 18 contiguous residues of SEQ ID NO: 2 and includes the sequence QQDFFPK (residues 7-13 of SEQ ID NO: 2). In other specific embodiments an immunogenic fragment of SEQ ID NO: 2 is between 10 and 18 contiguous residues of SEQ ID NO: 2 and includes the sequence QQDFFPK (residues 7-13 of SEQ ID NO: 2). In each instance an immunogenic fragment of SEQ ID NO: 2 has a function described herein (see, e.g., Abbreviations and Terms) or otherwise known in the art.

Further, at least because the subsequence QQDFFPK (residues 7-13 of SEQ ID NO: 2) is sufficient to produce a disclosed antigen-binding molecule, other RDP embodiments have the consensus sequence X1-6QQDFFPKX7-12 (SEQ ID NO: 6), where X1 through X12 are any amino acid. In more specific embodiments, an L2G peptide has the sequence X1-6QQDFFPKX7-12 (SEQ ID NO: 6), where X1 through X12 are any conservative substitution (e.g., very highly conserved substitution, highly conserved substitution or conserved substitution) of the corresponding amino acid residue in SEQ ID NO: 2. Exemplary conservative amino acid substitutions are set forth in the following table:

| Original Residue | Very Highly - Conserved Substitutions | Highly Conserved Substitutions (from the Blosum90 Matrix) | Conserved Substitutions (from the Blosum65 Matrix) |
|---|---|---|---|
| Ala | Ser | Gly, Ser, Thr | Cys, Gly, Ser, Thr, Val |
| Arg | Lys | Gln, His, Lys | Asn, Gln, Glu, His, Lys |
| Asn | Gln; His | Asp, Gln, His, Lys, Ser, Thr | Arg, Asp, Gln, Glu, His, Lys, Ser, Thr |
| Asp | Glu | Asn, Glu | Asn, Gln, Glu, Ser |
| Cys | Ser | None | Ala |
| Gln | Asn | Arg, Asn, Glu, His, Lys, Met | Arg, Asn, Asp, Glu, His, Lys, Met, Ser |
| Glu | Asp | Asp, Gln, Lys | Arg, Asn, Asp, Gln, His, Lys, Ser |
| Gly | Pro | Ala | Ala, Ser |
| His | Asn; Gln | Arg, Asn, Gln, Tyr | Arg, Asn, Gln, Glu, Tyr |
| Ile | Leu; Val | Leu, Met, Val | Leu, Met, Phe, Val |
| Leu | Ile; Val | Ile, Met, Phe, Val | Ile, Met, Phe, Val |
| Lys | Arg; Gln; Glu | Arg, Asn, Gln, Glu | Arg, Asn, Gln, Glu, Ser, |
| Met | Leu; Ile | Gln, Ile, Leu, Val | Gln, Ile, Leu, Phe, Val |
| Phe | Met; Leu; Tyr | Leu, Trp, Tyr | Ile, Leu, Met, Trp, Tyr |
| Ser | Thr | Ala, Asn, Thr | Ala, Asn, Asp, Gln, Glu, Gly, Lys, Thr |
| Thr | Ser | Ala, Asn, Ser | Ala, Asn, Ser, Val |
| Trp | Tyr | Phe, Tyr | Phe, Tyr |
| Tyr | Trp; Phe | His, Phe, Trp | His, Phe, Trp |
| Val | Ile; Leu | Ile, Leu, Met | Ala, Ile, Leu, Met, Thr |

Some exemplary RDPs having the consensus sequence X1-6QQDFFPKX7-12, (SEQ ID NO: 6) wherein any 1, 2, 3, 4, 5, 6, 7, 8, 9, 10, or 11 or all 12 of residues X1 through X12 will have conservative amino acid changes (such as, very highly conserved substitutions, highly conserved substitutions or conserved substitutions) as compared to SEQ ID NO: 2 and, as applicable, the remaining residues will have no change as compared to SEQ ID NO: 2.

In other embodiments, a RDP is a sequence variant of an L2G Peptide that has at least 99%, at least 98%, at least 95%, at least 92%, at least 90%, at least 85%, at least 80%, at least 75%, at least 70%, at least 65%, or at least 60% amino acid sequence identity to the amino acid sequence set forth in SEQ ID NO: 2. "Sequence identity" is a phrase commonly used to describe the similarity between two amino acid sequences (or between two nucleic acid sequences). Sequence identity typically is expressed in terms of percentage identity; the higher the percentage, the more similar the two sequences.

Methods for aligning sequences for comparison and determining sequence identity are well known in the art. Various programs and alignment algorithms are described in: Smith and Waterman, *Adv. Appl. Math.*, 2:482, 1981; Needleman and Wunsch, *J. Mol. Biol.*, 48:443, 1970; Pearson and Lipman, *Proc. Natl. Acad. Sci. USA*, 85:2444, 1988; Higgins and Sharp, *Gene*, 73:237-44, 1988; Higgins and Sharp, *CABIOS*, 5:151-3, 1989; Corpet et al., *Nucleic Acids Research*, 16:10881-90, 1988; Huang, et al., *Computer Applications in the Biosciences,* 8:155-65, 1992; Pearson et al., *Methods in Molecular Biology,* 24:307-331, 1994; Tatiana et al., *FEMS Microbiol. Lett.,* 174:247-50, 1999. Altschul et al. present a detailed consideration of sequence-alignment methods and homology calculations (*J. Mol. Biol.,* 215:403-10, 1990).

The National Center for Biotechnology Information (NCBI) Basic Local Alignment Search Tool (BLAST™, Altschul et al., *J. Mol. Biol.,* 215:403-10, 1990) is publicly available from several sources, including the National Center for Biotechnology Information (NCBI, Bethesda, Md.) and on the Internet, for use in connection with the sequence-analysis programs blastp, blastn, blastx, tblastn and tblastx. A description of how to determine sequence identity using this program is available on the internet under the help section for BLAST™.

For comparisons of amino acid sequences of greater than about 15 amino acids, the "Blast 2 sequences" function of the BLAST™ (Blastp) program is employed using the default BLOSUM62 matrix set to default parameters (cost to open a gap [default=5]; cost to extend a gap [default=2]; penalty for a mismatch [default=3]; reward for a match [default=1]; expectation value (E) [default=10.0]; word size [default=3]; and number of one-line descriptions (V) [default=100]. When aligning short peptides (fewer than around 15 amino acids), the alignment should be performed using the Blast 2 sequences function "Search for short nearly exact matches" employing the PAM30 matrix set to default parameters (expect threshold=20000, word size=2, gap costs: existence=9 and extension=1) using composition-based statistics.

Any disclosed sequence variant of a L2G Peptide (whether it is a variant having one or more conservative amino acid substitutions as compare to SEQ ID NO: 2 or a variant having a disclosed percentage sequence identity to SEQ ID NO: 2), at least, is immunogenic (alone or when couple to a carrier molecule) and, e.g., capable of eliciting production of a RD-binding molecule (such as a monoclonal antibody).

VI. EGFR Regulatory Domain-Binding Molecules

This disclosure also concerns EGFR-specific RD-binding molecules. RD-binding molecules are a species of antigen-binding molecules that specifically bind epitopes in the EGFR regulatory domain (which corresponds to residues 980-1210 of SEQ ID NO: 1), such as epitopes in the EGFR inhibitory subdomain (which corresponds to residues 1138-1196 of SEQ ID NO: 1).

Exemplary RD-binding molecules include RD-binding molecules specific for a L2G Peptide, or any epitope contained therein, or RD-binding molecules specific for a L2G Peptide sequence in EGFR (including RD-binding molecules that are competitively inhibited from binding EGFR by a L2G Peptide or fragment thereof), RD-binding molecules that recognize particular structural states of EGFR (for instance, RD-binding molecules specific for epitopes masked by EGFR protein-protein interactions), and/or RD binding molecules that recognize particular regulated states of EGFR (for instance, RD-binding molecules specific for epitopes contained with an EGFR inhibitory subdomain and which recognize the binding of a negative regulatory molecule (e.g., SOCS1 or SOCS2) to EGFR.

RD-binding molecules include, for example, antibodies or functional fragments or recombinant derivatives thereof, aptamers, mirror-image aptamers, or engineered nonimmunoglobulin binding proteins based on any one or more of the following scaffolds: fibronectin (e.g., ADNECTINST™ or monobodies), CTLA-4 (e.g., EVIBODIES™), tendamistat (e.g., McConnell and Hoess, J. Mol. Biol., 250:460-470, 1995), neocarzinostatin (e.g., Heyd et al., Biochem., 42:5674-5683, 2003), CBM4-2 (e.g., Cicortas-Gunnarsson et al., Protein Eng. Des. Sel., 17:213-221, 2004), lipocalins (e.g., ANTICALINS™; Schlehuber and Skerra, Drug Discov. Today, 10:23-33, 2005), T-cell receptors (e.g., Chlewicki et al., J. Mol. Biol., 346:223-239, 2005), protein A domain (e.g., AFFIBODIES™; Engfeldt et al., ChemBioChem, 6:1043-1050, 2005), Im9 (e.g., Bernath et al., J. Mol. Biol., 345:1015-1026, 2005), ankyrin repeat proteins (e.g., DARPins; Amstutz et al., J. Biol. Chem., 280:24715-24722, 2005), tetratricopeptide repeat proteins (e.g., Cortajarena et al., Protein Eng. Des. Sel., 17:399-409, 2004), zinc finger domains (e.g., Bianchi et al., J. Mol. Biol., 247:154-160, 1995), pVIII (e.g., Petrenko et al., Protein Eng., 15:943-950, 2002), GCN4 (Sia and Kim, Proc. Natl. Acad. Sci. USA, 100:9756-9761, 2003), avian pancreatic polypeptide (APP) (e.g., Chin et al., Bioorg. Med. Chem. Lett., 11:1501-1505, 2001), WW domains, (e.g., Dalby et al., Protein Sci., 9:2366-2376, 2000), SH3 domains (e.g., Hiipakka et al., J. Mol. Biol., 293:1097-1106, 1999), SH2 domains (Malabarba et al., Oncogene, 20:5186-5194, 2001), PDZ domains (e.g., TELOBODIES™; Schneider et al., Nat. Biotechnol., 17:170-175, 1999), TEM-1 β-lactamase (e.g., Legendre et al., Protein Sci., 11:1506-1518, 2002), green fluorescent protein (GFP) (e.g., Zeytun et al., Nat. Biotechnol., 22:601, 2004), thioredoxin (e.g., peptide aptamers; Lu et al., Biotechnol., 13:366-372, 1995), Staphylococcal nuclease (e.g., Norman, et al., Science, 285:591-595, 1999), PHD fingers (e.g., Kwan et al., Structure, 11:803-813, 2003), chymotrypsin inhibitor 2 (CI2) (e.g., Karlsson et al., Br. J. Cancer, 91:1488-1494, 2004), bovine pancreatic trypsin inhibitor (BPTI) (e.g., Roberts, Proc. Natl. Acad. Sci. USA, 89:2429-2433, 1992) and many others (see review by Binz et al., Nat. Biotechnol., 23(10):1257-1268, 2005 and supplemental materials).

In one embodiment, a disclosed RD-binding molecule is an aptamer. Aptamers include single-stranded nucleic acid molecules (such as, DNA or RNA) that assume a specific, sequence-dependent shape and binds to a target protein with high affinity and specificity. Aptamers generally comprise fewer than 100 nucleotides, fewer than 75 nucleotides, or fewer than 50 nucleotides. In another embodiment, a disclosed RD-binding molecule is a mirror-image aptamer (also called a SPIEGELMER™). Mirror-image aptamers are high-affinity L-enantiomeric nucleic acids (for example, L-ribose or L-2'-deoxyribose units) that display high resistance to enzymatic degradation compared with D-oligonucleotides (such as, aptamers). The target binding properties of aptamers and mirror-image aptamers are designed by an in vitro-selection process starting from a random pool of oligonucleotides, as described for example, in Wlotzka et al., *Proc. Natl. Acad. Sci.* 99(13):8898-902, 2002.

In another example, an aptamer is a peptide aptamer that binds to a target protein (e.g., an EGFR RD) with high affinity and specificity. Peptide aptamers include a peptide loop (e.g., which is specific for the target) attached at both ends to a protein scaffold. This double structural constraint greatly increases the binding affinity of the peptide aptamer to levels comparable to an antibody's (nanomolar range). The variable loop length is typically 8 to 20 amino acids (e.g., 8 to 12 amino acids), and the scaffold may be any protein which is stable, soluble, small, and non-toxic (e.g., thioredoxin-A, stefin A triple mutant, green fluorescent protein, eglin C, and cellular transcription factor Sp1). Peptide aptamer selection can be made using different systems, such as the yeast two-hybrid system (e.g., Gal4 yeast-two-hybrid system) or the LexA interaction trap system.

Disclosed RD-binding molecules also include antibodies. The term "antibody" refers to an immunoglobulin molecule (or combinations thereof) that specifically binds to, or is immunologically reactive with, a particular antigen, and includes polyclonal, monoclonal, genetically engineered and otherwise modified forms of antibodies, including but not limited to chimeric antibodies, humanized antibodies, heteroconjugate antibodies (e.g., bispecific antibodies, diabodies, triabodies, and tetrabodies), single chain Fv antibodies (scFv), polypeptides that contain at least a portion of an immunoglobulin that is sufficient to confer specific antigen binding to the polypeptide, and antigen binding fragments of antibodies, including, e.g., Fab', F(ab')$_2$, Fab, Fv, rIgG, or complementarity determining region (CDR) fragments.

A Fab fragment is a monovalent fragment consisting of the VL, VH, CL and CH1 domains; a F(ab')$_2$ fragment is a bivalent fragment comprising two Fab fragments linked by a disulfide bridge at the hinge region; an Fd fragment consists of the VH and CHI domains; an Fv fragment consists of the VL and VH domains of a single arm of an antibody; and a dAb fragment consists of a VH domain (see, e.g., Ward et al., *Nature* 341:544-546, 1989). A single-chain antibody (scFv) is an antibody in which a VL and VH region are paired to form a monovalent molecule via a synthetic linker that enables them to be made as a single protein chain (see, e.g., Bird et al., *Science,* 242: 423-426, 1988; Huston et al., *Proc. Natl. Acad. Sci. USA,* 85:5879-5883, 1988). Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites (see, e.g., Holliger et al., *Proc. Natl. Acad. Sci. USA,* 90:6444-8, 1993; Poljak et al., *Structure,* 2:1121-3, 1994). A chimeric antibody is an antibody that contains one or more regions from one antibody and one or more regions from one or more other antibodies. An antibody may have one or more binding sites. If there is more than one binding site, the binding sites may be identical to one another or may be different. For instance, a naturally occurring immunoglobulin has two identical binding sites, a single-chain antibody or Fab fragment has one binding site, while a "bispecific" or "bifunctional" antibody has two different binding sites.

As discussed above, exemplary RD-binding molecules recognize particular regulated or structural states of EGFR. For example, a disclosed RD-binding molecule can detect the masking (or unmasking) of an epitope in the EGFR regulatory domain (residues 980-1210 of SEQ ID NO: 1). Such epitope masking (or unmasking) can result, for instance, from a protein-protein interaction between EGFR and another cellular protein, such as a SOCS protein (e.g., SOCS1 or SOCS3); wherein the binding of the cellular protein to EGFR masks the epitope and the disassociation (or lack of association) of the two proteins unmasks the epitope.

In some examples, RD-binding molecules, such as antibodies (e.g., monoclonal antibody) or fragments thereof, are characterized by specific binding to any one or more EGFR RDPs disclosed herein (see, e.g., Section V). In other examples, RD-binding molecules, such as antibodies (e.g., monoclonal antibody) or fragments thereof, specifically bind to amino acid residues of EGFR that correspond to the sequence(s) of disclosed RDPs (see, e.g., Section V). In still other examples, RD-binding molecules, such as antibodies (e.g., monoclonal antibody) or fragments thereof, specifically bind to the EGFR regulatory domain or to the EGFR inhibitory subdomain and such specific binding is competitively inhibited by any one or more EGFR RDPs disclosed herein (see, e.g., Section V). Other examples involve RD-binding molecules (such as antibodies (e.g., monoclonal antibody) or fragments thereof) that specifically bind to the EGFR regulatory domain or to the EGFR inhibitory subdomain; wherein such specific binding is competitively inhibited by a SOCS protein, such as SOCS1 or SOCS3 (or a fragment of a SOCS protein that binds to the regulatory domain of EGFR (for example, a region of the regulatory domain including a phosphorylated Tyr residue)).

In one embodiment, a RD-binding molecule is a rabbit monoclonal antibody. In another particular embodiment, a RD-binding molecule is rabbit monoclonal antibody clone 5B7, which is commercially available from Ventana Medical Systems (Tucson, Ariz.; product number 790 4347).

In some examples, a RD-binding molecule (such as an antibody (e.g., monoclonal antibody) or fragments thereof) has an equilibrium constant ($K_d$) of 1 nM or less. For example, RD-binding molecules are provided that bind the regulatory domain (or inhibitory subdomain) of EGFR with a binding affinity of at least about $0.1 \times 10^{-8}$ M, at least about $0.3 \times 10^{-8}$ M, at least about $0.5 \times 10^{-8}$ M, at least about $0.75 \times 10^{-8}$ M, at least about $1.0 \times 10^{-8}$ M, at least about $1.3 \times 10^{-8}$ M at least about $1.5 \times 10^{-8}$ M, or at least about $2.0 \times 10^{-8}$ M.

A disclosed RD-binding molecule, such as an antibody (e.g., monoclonal antibody) or fragments thereof, optionally can be directly labeled with a detectable moiety. Useful detection agents include fluorescent compounds (including fluorescein, fluorescein isothiocyanate, rhodamine, 5-dimethylamine-1-napthalenesulfonyl chloride, phycoerythrin, lanthanide phosphors, or the cyanine family of dyes (such as Cy-3 or Cy-5) and the like); bioluminescent compounds (such as luciferase, green fluorescent protein (GFP), or yellow fluorescent protein); enzymes that can produce a detectable reaction product (such as horseradish peroxidase, β-galactosidase, luciferase, alkaline phosphatase, or glucose oxidase and the like), or radiolabels (such as $^3$H, $^{14}$C, $^{15}$N, $^{35}$S, $^{90}$Y, $^{99}$Tc, $^{111}$In, $^{125}$I, or $^{131}$I).

A. Making of Exemplary RD-binding Antibodies

Methods of making EGFR RD-binding molecules are well known in the art. The method used will depend upon the nature of the desired RD-binding molecules; for instance peptide-based RD-binding molecules that are not necessarily immunoglobulin in origin can be made using methods that are similar to phage display methods. One such method is described in Szardenings, *J. Recept. Signal Transduct. Res.,* 23:307-309, 2003.

Methods of generating antibodies (such as monoclonal or polyclonal antibodies) are well established in the art (for example see Harlow and Lane, *Antibodies: A Laboratory Manual*, Cold Spring Harbor Laboratory, New York, 1988). For example RDPs or RDPs conjugated to carrier molecules (or nucleic acids encoding such RDPs or conjugated RDPs) can be injected into non-human mammals (such as mice or rabbits), followed by boost injections, to produce an antibody response. Serum isolated from immunized animals may be isolated for the polyclonal antibodies contained therein, or spleens from immunized animals may be used for the production of hybridomas and monoclonal antibodies.

In one example, monoclonal antibody to epitopes in RDPs can be prepared from murine hybridomas according to the classical method of Kohler and Milstein (*Nature,* 256:495, 1975) or derivative methods thereof. Briefly, a mouse (such as Balb/c) is repetitively inoculated with a few micrograms of the selected RDP (such as SEQ ID NO: 2) or carrier conjugate thereof over a period of a few weeks. The mouse is then sacrificed, and the antibody-producing cells of the spleen isolated. The spleen cells are fused by means of polyethylene glycol with mouse myeloma cells, and the excess unfused cells destroyed by growth of the system on selective media comprising aminopterin (HAT media). The successfully fused cells are diluted and aliquots of the dilution placed in wells of a microtiter plate where growth of the culture is continued. Antibody-producing clones are identified by detection of antibody in the supernatant fluid of the wells by immunoassay procedures, such as ELISA, as originally described by Engvall (*Enzymol.*, 70:419, 1980), and derivative methods thereof. Selected positive clones can be expanded and their monoclonal antibody product harvested for use.

In another example, monoclonal antibody to epitopes in RDPs can be prepared from rabbit hybridomas as described in U.S. Pat. Nos. 7,148,332, 5,675,063, or 4,859,595.

In yet another example, monoclonal antibodies to epitopes of the EGFR inhibitory domain can be prepared by repetitively inoculating a non-human mammal (such as a mouse or rabbit) with one or more plasmids encoding a disclosed RDP (such as a plasmid encoding SEQ ID NO: 2). For example, pcDNA3 (Invitrogen, Carlsbad, Calif.) or a vector derived there from, can be manipulated using standard molecular biology methods to include a coding sequence for a disclosed RDP (e.g., SEQ ID NO: 2). In one exemplary method, Balb/c mice (6-8 weeks old) are immunized three times with the appropriate plasmid (20 μg in phosphate-buffered saline), and one boost can be given with cells before fusion. Mice can be injected three times intradermally into the base of the tail on days 0, 10, and 20 using an insulin syringe with a 28-gauge needle attached. Serum can be drawn on days 30 and 45 for evaluation of the anti-serum titer. To boost the immunized mice, cells expressing the desired plasmid are injected (for example on day at least 50). These injections can be intravenous and intraperitoneal. Spleens are harvested about 80-90 hours after the last cell boost for cell fusion.

Cell fusions of the splenocytes can be performed according to the protocol of Oi and Herzenberg (*Selected Methods in Cellular Immunology*, Freeman Press, San Fransisco, 1980). Splenocytes and SP2/0 cells are mixed, for example at a 4:1 ratio. The mixed cells are centrifuged and the cell pellet resuspended in polyethylene glycol (such as 40%-50% (w/v) polyethylene glycol) and appropriate medium. The resulting suspension is centrifuged and the cell pellet resuspended in HAT medium, and seeded in 96-well plates at 100 μl/well ($2.5 \times 10^5$ cells/well) and cultured in a $CO_2$ incubator. On the day after fusion, 100 μl of fresh HAT medium containing 500 μg/ml geneticin (Invitrogen) is added. On days 4 and 7, half of the spent medium is replaced by fresh HAT medium containing 250 μg/ml geneticin. On day 8, the growth of the hybridoma in each well is checked under a microscope. mAb production in culture supernatants can be assayed on day 10 by ELISA assay or days 9 and 10 by FACS sorter. Positive clones can be expanded and the specific hybridomas cloned by a limiting dilution method.

In addition, protocols for producing humanized forms of monoclonal antibodies and fragments of monoclonal antibodies are known in the art (see, e.g., U.S. Pat. Nos. 6,054, 297, 6,407,213, 6,639,055, 6,800,738, and 6,719,971 and U.S. Pat. Appl. Pub. Nos. 2005/0033031, and 2004/0236078). Similarly, methods for producing single chain antibodies have been described and can be useful for the making of RD-binding molecules disclosed herein (see, Buchner et al., *Anal. Biochem.* 205:263-270, 1992; Pluckthun, *Biotechnology* 9:545, 1991; Huse et al., *Science* 246:1275, 1989 and Ward et al., *Nature* 341:544, 1989).

B. Making of Exemplary RD-Binding Aptamers

Methods of generating aptamers (e.g., DNA or RNA aptamers) are well established in the art. For example, with knowledge of an RD sequence (see Section V) aptamers can be selected that bind to an RD amino acid sequence.

In one example, DNA or RNA aptamers are selected using the in vitro method SELEX (systematic evolution of ligands by exponential enrichment), for example using the method of Fitzwater and Polisky (*Methods Enzymol.*, 267:275-301, 1996). Such a method can be used to identify aptamers that bind with high specificity to a RD. The SELEX procedure is usually initiated with an RNA or DNA library containing about $10^{14}$-$10^{15}$ random oligonucleotide sequences. In a fully randomized oligonucleotide library, each molecule will exhibit a unique tertiary structure that will be dependent on the nucleotide sequence of that molecule. The binding affinity of the oligonucleotide for a particular RD will be determined by the fit between moieties on the surface of the oligonucleotide and epitopes on the target RD. By starting from a library of vast diversity, aptamers of nanomolar or subnanomolar affinity for the target RD with selectivity for that RD over other RDs with a high degree of structural homology can be identified. For example, RD peptides (or portion thereof, such as 3 to 20 amino acids of a target RD, for example an epitope) can be attached to a surface (such as a 96-well or other multi-well microtiter plate). The library of nucleic acid molecules can be added to the bound peptide under conditions that permit members of the library to bind to the peptide (e.g., by incubating at 37° C. for 30 minutes). Unbound members of the library are washed away, and then bound members of the library are eluted (e.g., by incubating at 95° C. for 10 minutes). Reverse transcription is performed (if the aptamers are RNA), followed by polymerase chain reaction and transcription to generate nucleic acids for the next round of SELEX. The dissociation constant (Kd) for resulting selected aptamer can be determined using routine methods. Aptamers with high affinity for the desired RD can be selected, such as a Kd of less than 100 nM, such as less than 50 nM, less than 10 nM, or less than 1 nM (for example 0.1 to 50 nM). Aptamers can be modified to increase their half-life, for example modified with 2'-fluorine-substituted pyrimidines, 2'-ribo purines, polyethylene glycol (PEG) linkage, and the like.

In one example, peptide aptamers are selected using a yeast two hybrid system, for example using the method of de Chassey et al. (*Molecular & Cellular Proteomics* 6:451-9, 2007). Reviews are provided, for example, in Borghouts et al. (*Comb. Chem. High Throughput Screen.* 11:135-45, 2008) and Buerger et al. (*J. Cancer Res. Clin. Oncol.* 129:669-75, 2003). Such a method can be used to identify peptide aptamers that bind with high specificity to a RD. A peptide aptamer library of high complexity is screened, such as 20 mer or 8-12 mer libraries. The library may or may not be based on information known about the sequence of the RD. In one example, the library includes oligonucleotides encoding variant peptides based on the amino acid sequence of the target RD. The library includes oligonucleotides encoding the variable peptides inserted into a vector encoding the scaffold protein (e.g., thioredoxin). When expressed, "prey" peptide sequences are embedded in the scaffold protein. A nucleic acid sequence or vector encoding the "bait" target RD fused to a transcription module (e.g., Gal4 or LexA) is expressed in the cells (e.g., yeast) along with the "prey" coding sequences.

If the yeast-two-hybrid system is used, the "prey" peptide aptamer can be fused to Gal4-transactivation domain (Gal4-

AD) and can also include a nuclear localization signal and an HA tag for detection. Exemplary vectors that can be used to express the peptide aptamer include pRS424, pAD-Trx, pGAD424; pGAD-T7, pACT2, and pAD-Gal4-2.1. A vector encoding the "bait" target protein fused to the Gal4 DNA binding domain is expressed in yeast along with the "prey" coding sequences. Exemplary vectors that can be used to express the "bait" peptide include pPC97, pLex9, pGBK-T7, and pDB-Gal4Cam. In some examples, the reporter yeast strain into which prey and bait vectors are introduced include His3, Ade2, Ura3 and LacZ genes under the control of a Gal upstream activating sequences to permit selection of clones where the bait and prey specifically bind. To select for desired peptide aptamers, transformed yeast cells are placed on media lacking histidine, adenine, or uracil. β-gal assays can be performed to quantify binding between identified aptamers and the target. To increase selection stringency, the amount of 3-AT inhibitor (e.g., 10-100 mM) can be increased. Cells that grow indicate the presence of peptide aptamer binding to the target RD.

If the LexA interaction trap system is used, a vector encoding the "prey" peptide aptamer fused to B42 or B112 acid transactivation domain can be used. Exemplary vectors that can be used to express the peptide aptamer include pWP1, pWP2, pJG4-5, pJM1, pHA3). A vector encoding the "bait" target protein fused to the DNA binding domain of the LexA repressor is expressed in yeast along with the "prey" coding sequences. An exemplary vector that can be used to express the "bait" peptide includes pEG202. Expression of the prey vector is induced if galactose is present in the growth medium. To select for desired peptide aptamers, transformed yeast cells are placed on media with galactose. Interactions between bait protein and peptide aptamer are detected on galactose plates that lack leucine. Cells that grow indicate the presence of peptide aptamer binding to the target RD.

Clones indicated to carry the desired protein aptamer that binds to the RD can be selected, and the vector encoding the aptamer isolated and cloned using standard recombinant technology.

VII. Kits

Any of the RD-binding molecules described in this disclosure can be supplied in the form of a kit useful, at least, for performing the methods described herein. In one embodiment of such a kit, an appropriate amount of at least one RD-binding molecule (e.g., monoclonal antibody (such as clone 5B7) or fragment thereof) is provided in one or more containers. In other embodiments, at least one RD-binding molecule (e.g., monoclonal antibody (such as clone 5B7) or fragment thereof) may be provided suspended in an aqueous solution or as a freeze-dried or lyophilized powder, for instance. The container(s) in which the at least one RD-binding molecule (e.g., monoclonal antibody (such as clone 5B7) or fragment thereof) is supplied can be any conventional container that is capable of holding the supplied form, for instance, microfuge tubes, ampoules, or bottles. The amount of RD-binding molecule (e.g., monoclonal antibody (such as clone 5B7) or fragment thereof) supplied can be any appropriate amount, such as from about 1 to about 5 µg/ml.

In other embodiments, control slides upon which are mounted one or more tissue or cell preparations (e.g., xenografts, cell pellets, or clotted cells) that may serve as positive and/or negative controls for a RD-binding molecule (e.g., monoclonal antibody (such as clone 5B7) or fragment thereof) may be provided in an appropriate and separate container. In some instances, A431, DU145, and/or Caski cells (or xenografts prepared therewith) may serve as a positive control. In other instances, MCF-7 cells (or xenografts prepared therewith) may serve as a negative control.

Other kit embodiments will include means for detection of the RD-binding molecule, such as secondary antibodies (e.g., goat anti-rabbit antibodies or rabbit anti-mouse antibodies). In some such instances, the secondary antibody will be directly labeled with a detectable moiety (as described elsewhere in this disclosure). In other instances, the primary or secondary (or higher-order) antibody will be conjugated to a hapten (such as biotin, DNP, and/or FITC), which is detectable by a detectably labeled cognate hapten-binding molecule (e.g., streptavidin (SA)-horse radish peroxidase, SA-alkaline phosphatase, and/or SA-QDot™). Some kit embodiments may include colorimetric reagents (e.g., DAB, and/or AEC) in suitable containers to be used in concert with primary or secondary (or higher-order) antibodies that are labeled with enzymes for the development of such colorimetric reagents.

In one embodiment, a kit includes instructional materials disclosing methods of use of the kit contents (e.g., RD-binding molecule) in a disclosed method. The instructional materials may be written, in an electronic form (e.g. computer diskette or compact disk) or may be visual (e.g. video files). The kits may also include additional components to facilitate the particular application for which the kit is designed. Thus, for example, the kits may additionally include buffers and other reagents routinely used for the practice of a particular method. Such kits and appropriate contents are well known to those of skill in the art.

The following examples are provided to illustrate certain particular features and/or embodiments. These examples should not be construed to limit the invention to the particular features or embodiments described.

EXAMPLES

Example 1

An Exemplary Monoclonal Antibody Specific for EGFR Regulatory Domain

This Example describes an exemplary RD-binding molecule; more particularly a monoclonal antibody that binds an epitope in the EGFR inhibitory subdomain. This antibody has the added advantage that it will identify not only full-length EGFR, but also truncated mutant forms of EGFR, which have been shown to be constitutively activated (Pedersen et al., *Ann. Oncol.,* 12(6):745-60, 2001).

A computer program (DNASTAR™, Madison, Wis.) was used for the selection of immunogenic peptide sequences within the EGFR intracellular domain. The program examined the input protein sequence for short (e.g., less than 20 contiguous amino acids) sequences that likely had a high probability for producing an antibody response in animals immunized with immunogens including such short sequences.

One identified short sequence was LDNPDYQQDFFP-KEAKPNG (L2G Peptide; SEQ ID NO: 2), which, by computer analysis, had high antigenicity, high hydrophilic regions, and high surface probability regions. This amino acid sequence was selected and a corresponding peptide was synthesized using a commercially available service (Anaspec, San Jose, Calif.).

The synthesized peptide was conjugated to Keyhole Limpet Hemocyanin (KLH) using standard methods. Rabbits were immunized with the KLH-peptide conjugate by a commercially available service (Strategic Diagnostics, Inc. Newark, Del.).

Rabbit sera containing antibodies specific for the L2G Peptide were identified by ELISA assay. The animal with the strongest serum titer was selected for a splenectomy. The viable spleen was shipped to Epitomics, Inc (Burlingame, Calif.) overnight where the immunized spleen cells were prepared for fusion with an immortalized cell line (240E-w) as described, e.g., in U.S. Pat. No. 5,675,063 or European Pat. No. EP0815213B1.

Hybridoma supernatants were tested by ELISA assay for the presence of antibodies specific for the L2G Peptide. One hybridoma was selected based on a relatively high antibody titer in the corresponding supernatant. The specificity of antibodies produced by the selected hybridoma cell line was confirmed by immunohistochemistry (IHC) testing on known EGFR-positive tissues (including squamous cell carcinoma of the lung, colon adenocarcinomas, and normal skin). The hybridoma cell line delivered by the manufacturer was subcloned to homogeneity to isolate a high-producing hybridoma clone designated 5B7.

Figure 4:
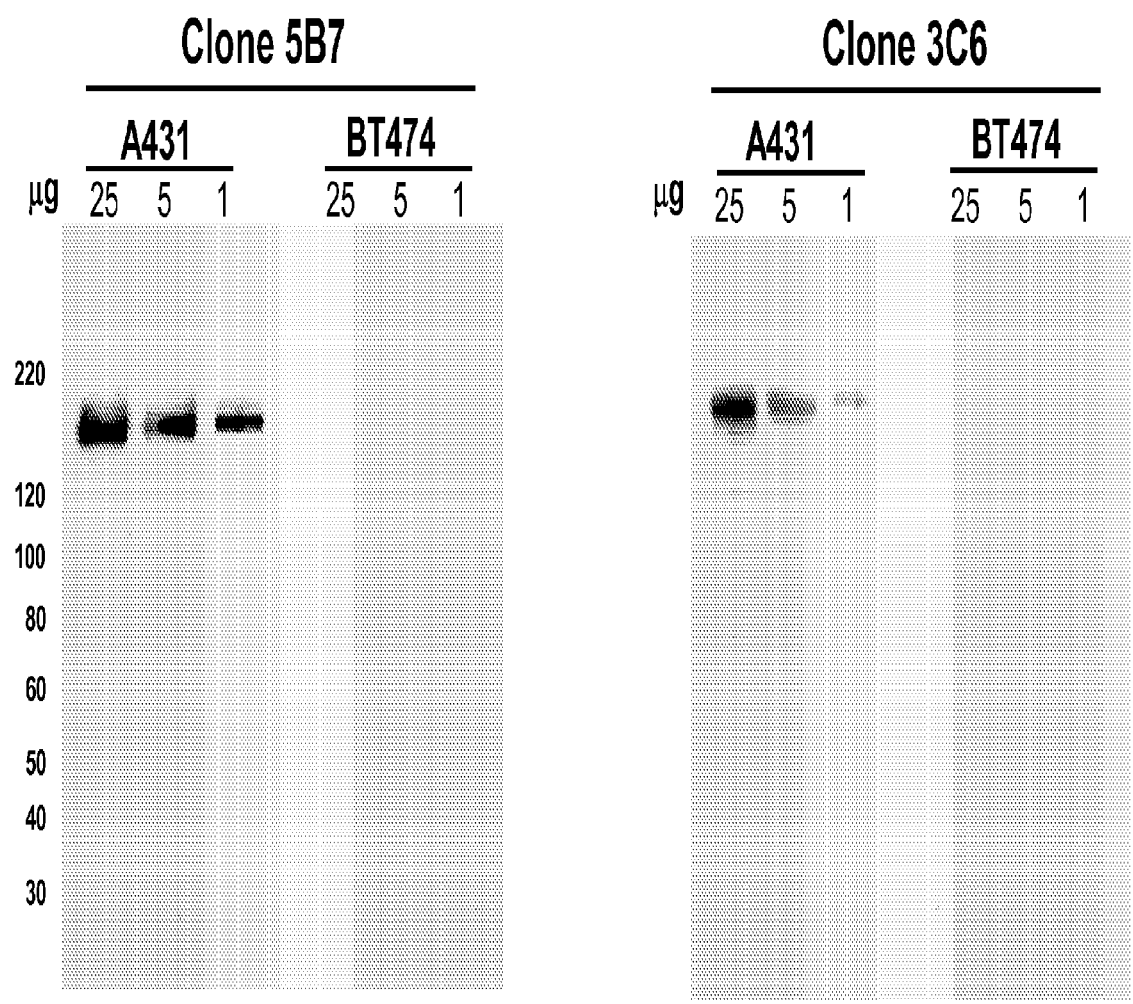
FIG. 4 shows the results of two Western blots in which three total protein concentrations (as indicated) of A431 (EGFR-positive) and BT474 (EGFR-negative) cell lysates were run. The left and right representations show clone 5B7 and clone 3C6, respectively, binding to a single protein band (appropriate in size for EGFR) in A431 cell lysates. Molecular weights (in kD) are shown at the far left.
Figure 5A:
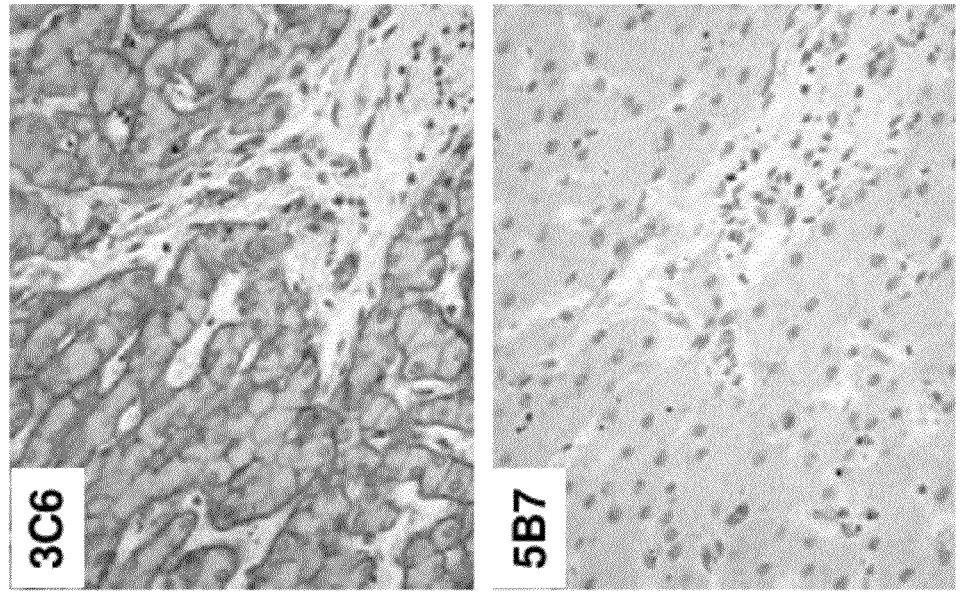

A Western blot analysis was performed to ensure the specificity of clone 5B7. Total protein lysates were prepared from A431 cells, which are known to express high levels of EGFR on their cell surface, and from BT474 cells, which are negative for EGFR, but which express related EGFR family members, EGFR2 and EGFR3. As shown in FIG. 4, clone 5B7 and a mouse monoclonal antibody specific for the EGFR external domain (clone 3C6) recognized the same 170 kDa band, which is consistent with the size of the EGFR protein. The lack of staining of the BT474 cell lysates for both antibodies indicated that neither antibody cross reacted with EGFR family members that have conserved homology. Thus, the 3C6 and 5B7 antibodies were specific for EGFR.

Example 2

Exemplary Methods for Immunohistochemical Staining of Tissue with EGFR-Specific Antibodies Immunohistochemistry is the well-known method and variations on such methods are readily determined with routine experimentation by those of ordinary skill in the art (see, e.g., Dabbs, *Diagnostic Immunohistochemistry*, Churchill Livingstone, 2002). Exemplary methods for detecting in FFPE tissue by manual IHC an EGFR RD-binding molecule (e.g., monoclonal antibody clone 5B7) or an antigen-binding molecule specific for the EGFR extracellular domain (e.g., monoclonal antibody clone 3C6) are provided in the following table:

| Step # | Manual IHC Assay |
|---|---|
| 0 | Fresh tissue is placed in a fixative (such as, 10% neutral buffered formalin) for approximately 12-48 hours at room temperature. Then, the tissue is dehydrated through graded alcohols (e.g., 50% to 70% to 90% to 95% to 100% EtOH) for 1-2 hours at each grade, and infiltrated with a clearing reagent (such as, xylene) for 3-5 hours at room temperature. The cleared tissue is placed in melted (approximately 63 degrees C) paraffin for 3-6 hours. Samples are removed and embedded in paraffin blocks for subsequent microtome sectioning. 3-10 µm sections are cut and placed on glass slides. |
| 1 | Deparaffinize tissue sections in xylene; then, rehydrate through graded alcohols to distilled water. |
| 2 | Place tissue sections in 0.5% v/v hydrogen peroxide/methanol for approximately 10 minutes. |
| 3 | Pretreat slides for antigen retrieval using an appropriate method (e.g., high-temperature antigen unmasking, trypsin, etc.) if required. |
| 4 | Wash slides with distilled water for approximately 5 minutes. |
| 5 | Wash slides in saline buffer (e.g., PBS, TBS) for 5 minutes. |
| 6 | Cover tissue sections with blocking reagent (e.g., 10% v/v normal rabbit serum in buffer) for approximately 10 minutes. |
| 7 | Remove excess blocking reagent and replace with primary antibody (e.g., rabbit monoclonal antibody or mouse monoclonal antibody) diluted in blocking reagent as required for approximately 60 minutes at 25° C. or overnight at 4° C. |
| 8 | Wash twice in buffer for approximately 5 minutes per wash. |
| 9 | Remove excess buffer and incubate tissue sections with biotinylated secondary antibody (e.g., biotinylated rabbit anti-mouse antibody or biotinylated goat anti-rabbit antibody as appropriate for the subject primary antibody) diluted in blocking reagent for 30 minutes at 25° C. |
| 10 | Wash twice in buffer for approximately 5 minutes per wash. |
| 11 | Remove excess buffer and incubate tissue sections with streptavidin-horse radish peroxidase (HRP) conjugate for 30 minutes at 25° C. |
| 12 | Wash twice in buffer for approximately 5 minutes per wash. |
| 13 | Develop detectable color with 3,3'-diaminobenzidine tetrahydrochloride (DAB) at room temperature for approximately 5-10 minutes. |
| 14 | Rinse slides in water. |
| 15 | If desired counterstain with hematoxylin (e.g., Carson, Histotechnology: A Self-Instructional Text, Chicago: ASCP Press, 1997). |
| 16 | Dehydrate, clear and mount coverslip on slides. |

IHC for the detection antibodies specific for the EGFR regulatory domain also can be performed on automated staining platforms, such as the BenchMark™ series instruments manufactured by Ventana Medical Systems (Tucson, Ariz.). An exemplary assay for the detection of a monoclonal antibody specific for the EGFR regulatory domain (e.g., clone 5B7) on a BenchMark™ series automated tissue stainer is described in the following table:

| Step # | Anti-EGFR Regulatory Domain Antibody Staining (Automated Assay) |
|---|---|
| 1 | ***** Select EZ Prep ***** |
| 2 | ***** Start Timed Steps ***** |
| 3 | ***** Mixers Off ***** |
| 4 | Warmup Slide to 75° C., and Incubate for 4 Minutes |
| 5 | Apply EZPrep Volume Adjust |
| 6 | Rinse Slide |
| 7 | Apply EZPrep Volume Adjust |
| 8 | Rinse Slide |
| 9 | Apply EZPrep Volume Adjust |
| 10 | Apply Coverslip |
| 11 | Warmup Slide to 76° C., and Incubate for 4 Minutes |
| 12 | Rinse Slide |
| 13 | Apply Depar Volume Adjust |
| 14 | Apply Coverslip |
| 15 | Disable Slide Heater |
| 16 | ***** Mixers On ***** |
| 17 | [Short - 8 Minute Conditioning] |
| 18 | Rinse Slide |
| 19 | Apply Long Cell Conditioner #1 |
| 20 | Apply CC Coverslip Long |
| 21 | ***** Select SSC Wash ***** |
| 22 | Warmup Slide to 95° C., and Incubate for 8 Minutes |
| 23 | [Mild - 30 Minute Conditioning] |
| 24 | Apply Cell Conditioner #1 |
| 25 | Apply CC Medium Coverslip No BB |
| 26 | Warmup Slide to 100° C., and Incubate for 4 Minutes |
| 27 | Apply CC Medium Coverslip No BB |
| 28 | Apply Cell Conditioner #1 |
| 29 | Apply CC Medium Coverslip No BB |
| 30 | Apply Cell Conditioner #1 |
| 31 | Apply CC Medium Coverslip No BB |
| 32 | Apply Cell Conditioner #1 |
| 33 | Apply CC Medium Coverslip No BB |
| 34 | Apply Cell Conditioner #1 |
| 35 | Apply CC Medium Coverslip No BB |
| 36 | Apply Cell Conditioner #1 |
| 37 | Apply CC Medium Coverslip No BB |
| 38 | [Standard - 60 Minute Conditioning] |
| 39 | Apply Cell Conditioner #1 |
| 40 | Apply CC Medium Coverslip No BB |
| 41 | Apply Cell Conditioner #1 |
| 42 | Apply CC Medium Coverslip No BB |
| 43 | Apply Cell Conditioner #1 |
| 44 | Apply CC Medium Coverslip No BB |
| 45 | Apply Cell Conditioner #1 |
| 46 | Apply CC Medium Coverslip No BB |
| 47 | Apply Cell Conditioner #1 |
| 48 | Apply CC Medium Coverslip No BB |
| 49 | Apply Short Cell Conditioner #1 |
| 50 | Apply CC Medium Coverslip No BB |
| 51 | Apply Cell Conditioner #1 |
| 52 | Apply CC Medium Coverslip No BB |
| 53 | Disable Slide Heater |
| 54 | Incubate for 8 Minutes |
| 55 | Rinse Slide With Reaction Buffer |
| 56 | Adjust Slide Volume With Reaction Buffer |
| 57 | Apply Coverslip |
| 58 | Rinse Slide With Reaction Buffer |
| 59 | Adjust Slide Volume With Reaction Buffer |
| 60 | Apply Coverslip |
| 61 | ***** Procedure Synchronization ***** |
| 62 | Warmup Slide to 37° C., and Incubate for 4 Minutes |
| 63 | Rinse Slide With Reaction Buffer |
| 64 | Adjust Slide Volume With Reaction Buffer |
| 65 | Apply One Drop of I-VIEW INHIBITOR, Apply Coverslip, and Incubate for 4 Minutes |
| 66 | Rinse Slide With Reaction Buffer |
| 67 | Adjust Slide Volume With Reaction Buffer |
| 68 | Apply Coverslip |
| 69 | Warmup Slide to 37° C., and Incubate for 4 Minutes |
| 70 | Rinse Slide With Reaction Buffer |
| 71 | Adjust Slide Volume With Reaction Buffer |
| 72 | Apply Coverslip |
| 73 | Apply One Drop of Antibody (e.g., clone 5B7), and Incubate for [0 Hr 16 Min] |
| 74 | Rinse Slide With Reaction Buffer |
| 75 | Adjust Slide Volume With Reaction Buffer |
| 76 | Apply Coverslip |
| 77 | Warmup Slide to 37° C., and Incubate for 4 Minutes |

| Step # | Anti-EGFR Regulatory Domain Antibody Staining (Automated Assay) |
|---|---|
| 78 | Rinse Slide With Reaction Buffer |
| 79 | Adjust Slide Volume With Reaction Buffer |
| 80 | Apply One Drop of I-VIEW BIOTIN Ig, Apply Coverslip, and Incubate for 8 Minutes |
| 81 | Rinse Slide With Reaction Buffer |
| 82 | Adjust Slide Volume With Reaction Buffer |
| 83 | Apply One Drop of I-VIEW SA-HRP, Apply Coverslip, and Incubate for 8 Minutes |
| 84 | Rinse Slide With Reaction Buffer |
| 85 | Adjust Slide Volume With Reaction Buffer |
| 86 | Apply Coverslip |
| 87 | Rinse Slide With Reaction Buffer |
| 88 | Adjust Slide Volume With Reaction Buffer |
| 89 | Apply One Drop of I-VIEW DAB and One Drop of I-VIEW $H_2O_2$, Apply Coverslip, Incubate for 8 Minutes |
| 90 | Rinse Slide With Reaction Buffer |
| 91 | Adjust Slide Volume With Reaction Buffer |
| 92 | Apply One Drop of I-VIEW COPPER, Apply Coverslip, and Incubate for 4 Minutes |
| 93 | Rinse Slide With Reaction Buffer |
| 94 | Adjust Slide Volume With Reaction Buffer |
| 95 | Apply One Drop of [HEMATOXYLIN II] (Counterstain), Apply Coverslip, and Incubate for [4 Minutes] |
| 96 | Rinse Slide With Reaction Buffer |
| 97 | Adjust Slide Volume With Reaction Buffer |
| 98 | Apply Coverslip |
| 99 | Rinse Slide With Reaction Buffer |
| 100 | Adjust Slide Volume With Reaction Buffer |
| 101 | Apply One Drop of [BLUING REAGENT] (Post Counterstain), Apply Coverslip, and Incubate for [4 Minutes] |
| 102 | Rinse Slide With Reaction Buffer |
| 103 | Apply Coverslip |
| 104 | Disable Slide Heater |
| 105 | ***** Select Optional Wash ***** |
| 106 | ***** Select SSC Wash ***** |
| 107 | ***** Start Timed Steps ***** |
| 108 | Rinse Slide With Reaction Buffer |

35

An exemplary assay for the detection of a monoclonal antibody specific for the EGFR external domain (e.g., clone 3C6) on a BenchMark™ series automated tissue stainer is described in the following table:

| Step # | Anti-EGFR External Domain Antibody Staining (Automated Assay) |
|---|---|
| 1 | ***** Select EZ Prep ***** |
| 2 | ***** Start Timed Steps ***** |
| 3 | ***** Mixers Off ***** |
| 4 | Warm Slide to 75° C., and Incubate for 4 Minutes |
| 5 | Apply EZPrep Volume Adjust |
| 6 | Rinse Slide |
| 7 | Apply EZPrep Volume Adjust |
| 8 | Rinse Slide |
| 9 | Apply EZPrep Volume Adjust |
| 10 | Apply Coverslip |
| 11 | Warm Slide to 76° C., and Incubate for 4 Minutes |
| 12 | Rinse Slide |
| 13 | Apply Depar Volume Adjust |
| 14 | Apply Coverslip |
| 15 | Disable Slide Heater |
| 16 | ***** Mixers On ***** |
| 17 | Disable Slide Heater |
| 18 | ***** Select SSC Wash ***** |
| 19 | Rinse Slide With Reaction Buffer |
| 20 | Adjust Slide Volume With Reaction Buffer |
| 21 | Apply Coverslip |
| 22 | Rinse Slide With Reaction Buffer |
| 23 | Adjust Slide Volume With Reaction Buffer |
| 24 | Apply Coverslip |
| 25 | ***** Procedure Synchronization ***** |
| 26 | Warm Slide to 37° C., and Incubate for 4 Minutes |
| 27 | Rinse Slide With Reaction Buffer |
| 28 | Adjust Slide Volume With Reaction Buffer |
| 29 | Apply One Drop of I-VIEW INHIBITOR, Apply Coverslip, and Incubate for 4 Minutes |

-continued

| Step # | Anti-EGFR External Domain Antibody Staining (Automated Assay) |
|---|---|
| 30 | Rinse Slide With Reaction Buffer |
| 31 | Adjust Slide Volume With Reaction Buffer |
| 32 | Apply One Drop of [PROTEASE 1] (Enzyme), Apply Coverslip, and Incubate for [8 Minutes] |
| 33 | Rinse Slide With Reaction Buffer |
| 34 | Adjust Slide Volume With Reaction Buffer |
| 35 | Apply Coverslip |
| 36 | Warm Slide to 37° C., and Incubate for 4 Minutes |
| 37 | Rinse Slide With Reaction Buffer |
| 38 | Adjust Slide Volume With Reaction Buffer |
| 39 | Apply Coverslip |
| 40 | Apply One Drop of Antibody (e.g., clone 3C6), and Incubate for [0 Hr 32 Min] |
| 41 | Rinse Slide With Reaction Buffer |
| 42 | Adjust Slide Volume With Reaction Buffer |
| 43 | Apply Coverslip |
| 44 | Warm Slide to 37° C., and Incubate for 4 Minutes |
| 45 | Rinse Slide With Reaction Buffer |
| 46 | Adjust Slide Volume With Reaction Buffer |
| 47 | Apply One Drop of I-VIEW BIOTIN Ig, Apply Coverslip, and Incubate for 8 Minutes |
| 48 | Rinse Slide With Reaction Buffer |
| 49 | Adjust Slide Volume With Reaction Buffer |
| 50 | Apply One Drop of I-VIEW SA-HRP, Apply Coverslip, and Incubate for 8 Minutes |
| 51 | Rinse Slide With Reaction Buffer |
| 52 | Adjust Slide Volume With Reaction Buffer |
| 53 | Apply Coverslip |
| 54 | Rinse Slide With Reaction Buffer |
| 55 | Adjust Slide Volume With Reaction Buffer |
| 56 | Apply One Drop of I-VIEW DAB and One Drop of I-VIEW $H_2O_2$, Apply Coverslip, Incubate for 8 Minutes |
| 57 | Rinse Slide With Reaction Buffer |
| 58 | Adjust Slide Volume With Reaction Buffer |
| 59 | Apply One Drop of I-VIEW COPPER, Apply Coverslip, and Incubate for 4 Minutes |
| 60 | Rinse Slide With Reaction Buffer |
| 61 | Adjust Slide Volume With Reaction Buffer |
| 62 | Apply One Drop of [HEMATOXYLIN II] (Counterstain), Apply Coverslip, and Incubate for [4 Minutes] |
| 63 | Rinse Slide With Reaction Buffer |
| 64 | Adjust Slide Volume With Reaction Buffer |
| 65 | Apply Coverslip |
| 66 | Rinse Slide With Reaction Buffer |
| 67 | Adjust Slide Volume With Reaction Buffer |
| 68 | Apply One Drop of [BLUING REAGENT] (Post Counterstain), Apply Coverslip, and Incubate for [4 Minutes] |
| 69 | Rinse Slide With Reaction Buffer |
| 70 | Apply Coverslip |
| 71 | Disable Slide Heater |
| 72 | ***** Select Optional Wash ***** |
| 73 | ***** Select SSC Wash ***** |
| 74 | ***** Start Timed Steps ***** |
| 75 | Rinse Slide With Reaction Buffer |

Example 3

Antibody Specific for EGFR Regulatory Domain Epitope Unexpectedly does not Substantially Bind to Some EGFR-Positive Tissues This Example demonstrates that RD-binding molecules, such as clone 5B7, exhibited differential binding to EGFR-positive tissues (as detected by an antibody specific for the EGFR external domain). As described in more detail below, but without being limited to a single theory, this differential binding is believed to be due to the differential expression of EGFR regulatory proteins (e.g., SOCS proteins like SOCS1 or SOCS3) in EGFR-positive tissues. Such regulatory proteins, when directly associated with the EGFR regulatory domain, mask the epitopes of RD-binding molecules.

A. Normal Human Tissues

The staining by IHC of antibodies specific for the EGFR regulatory domain (i.e., clone 5B7) and external domain (i.e., clone 3C6) in FFPE 30 normal human tissues were compared. Tissue arrays were obtained from USBiomax (Igamsville, Md.; Cat. No. FDA801). Automated staining protocols as described in Example 2 were used to stain the tissue arrays on a BenchMark™ automated tissues stainer.

As shown in FIGS. 5A and 5B, extracellular-domain-specific clone 3C6 positively stained skin, testis, tonsil, liver and placenta tissues, which is consistent with known EGFR expression patterns in normal tissue. FIG. 5A also shows that regulatory-domain-specific clone 5B7 reacted positively with normal skin, testis, and tonsil. However, surprisingly, this antibody did not react with normal liver (see, e.g., FIG. 5B) and had variable reactivity with placental EGFR depending on the stage of development of the placenta (*Virchows Archiv A Pathol Anat.,* 420:385 393, 1992).

B. Human NSCLC Tumors

Non-small cell lung cancer (NSCLC) cells are known to express EGFR in approximately 75% of tumors. Regulatorydomain-specific clone 5B7 and external-domain-specific clone 3C6 were used to stain a cohort of NSCLC cases from three commercially available tissue micro arrays (Array LC801 and Array LC819 (Biomax; Ijamsville, Md.) and Array IMH-305 (Imgenex (San Diego, Calif.)).

As shown in Table 3, Subpart A, clone 3C6 detected EGFR in 83% of the lung cases (as would be expected based on literature estimates of EGFR staining in NSCLC) while clone 5B7 stained positively 65% of lung tumors. This corresponds to an 18.5% discordance between clone 3C6 and clone 5B7 with the latter exhibiting no staining in 38 cases that were positive for clone 3C6 staining

TABLE 3

Summary of NSCLC Immunohistochemistry Study

| 5B7 | 3C6 Positive | 3C6 Negative | Total |
|---|---|---|---|
| Subpart A | | | |
| Positive | 132 | 1 | 133 |
| Negative | 38 | 34 | 72 |
| Total | 170 | 35 | 205 |
| Subpart B | | | |
| Sensitivity | | 78% | |
| Specificity | | 97% | |
| Overall | | 81% | |
| Kappa | | 67% | |

As summarized in Table 3, Subpart B, the two antibodies each stained positively in 78% of cases (i.e., Sensitivity (132/[132+38]); the two antibodies each stained negatively in 97% of cases (i.e., Specificity (34/[1+34]). The overall agreement was 81% ([132+43]/205). The Kappa statistic, which is another measure of agreement, can be interpreted as follows: <0=No agreement, 0.0-0.19=Poor agreement, 0.20-0.39=Fair agreement, 0.40-0.59=Moderate agreement, 0.60-0.79=Substantial agreement and 0.80-1.00=Almost perfect agreement (Landis and Koch, Biometrics, 33:159-174, 1977). The Kappa score for 3C6 versus 5B7 was 67% which falls into the substantial agreement category.

Figure 6:
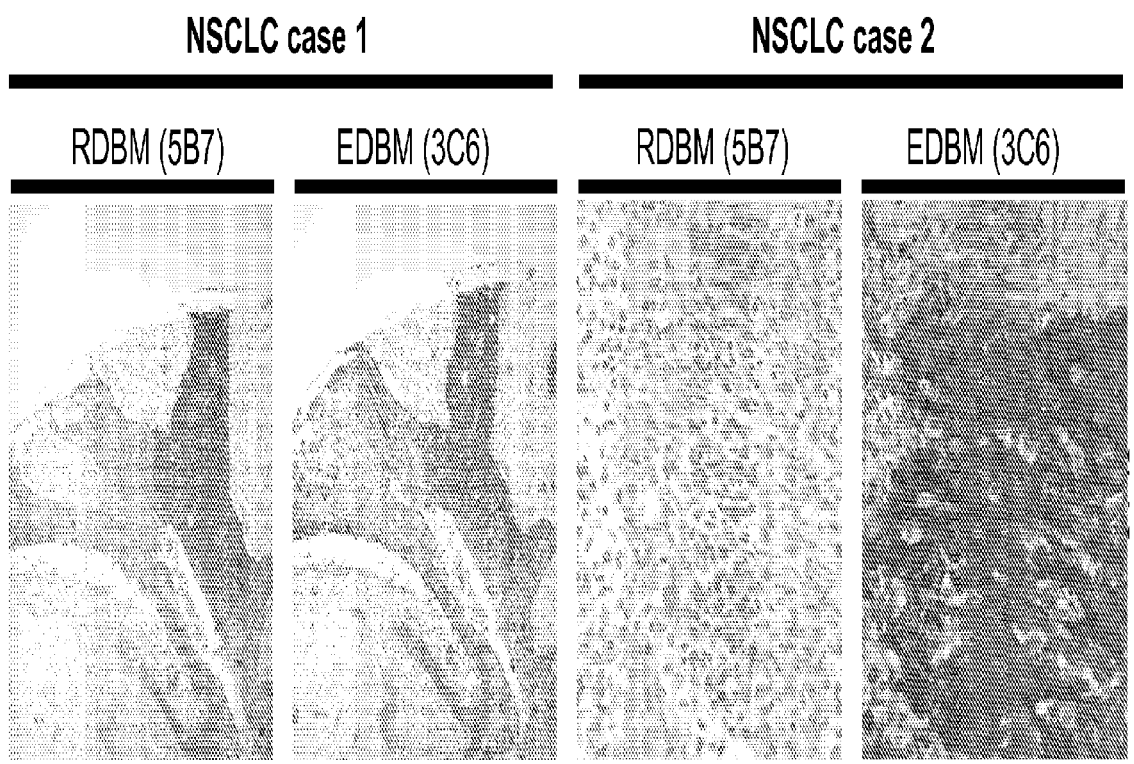
FIG. 6 shows images demonstrating the differences in the binding of EGFR regulatory-domain-specific (RDBM) clone 5B7 and EGFR external-domain-specific (EDBM) clone 3C6 in two representative non-small cell lung cancer (NSCLC) tissue sections.

Particular examples demonstrating differences in the binding of EGFR regulatory-domain-specific clone 5B7 and EGFR external-domain-specific clone 3C6 to squamous cell carcinomas of the lung are shown in FIG. 6. Case 1 (left panel) showed equivalent staining of cells by the two antibodies, which indicates (among other things) that there is not a difference in the general sensitivity of clone 5B7 as compared to clone 3C6 when the epitope for each is accessible. Case 2 (right panel) showed distinctly different staining between the two antibodies with clone 5B7 being negative and clone 3C6 being 3+ positive (0-3+ scale).

The differential binding of clone 5B7 (specific for the EGFR intracellular regulatory domain) as compared to clone 3C6 (specific for the EGFR extracellular domain) in normal and neoplastic tissues as shown in this Example strongly supports the belief that the clone 5B7 epitope was accessible only in some tissues.

Example 4

Epitope Mapping of Monoclonal Antibody Clone 5B7

Figures 7A, 7B:
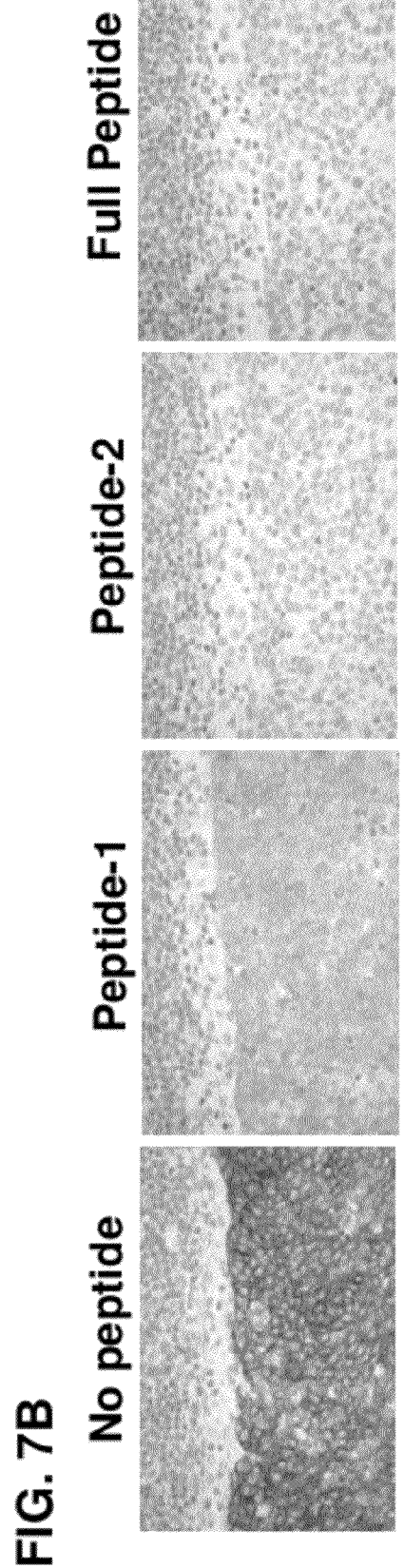
FIGS. 7A and 7B show the results of peptide inhibition studies mapping the epitope of the EGFR regulatory-domain-specific clone 5B7.

The epitope for the EGFR regulatory-domain-specific monoclonal antibody, clone 5B7, was mapped by peptide inhibition studies. Because the L2G Peptide was used as the immunogen and was used to screen for positive clones, it was known that the 5B7 epitope must be within that 19-amino acid sequence (see SEQ ID NO: 2). The L2G Peptide, a peptide containing the 13 C-terminal amino acid residues of the L2G Peptide, and a peptide containing the six N-terminal amino acid residues of the L2G Peptide plus three additional N-terminal residues (i.e., QIS) corresponding to the respective positions in the human EGFR sequence. The amino acid sequences of the subject peptides are shown in FIG. 7A. The peptides were synthesized by Genemed Synthesis, Inc. (South San Francisco, Calif.).

A known EGFR-positive lung squamous cell carcinoma was chosen for the peptide inhibition study. The 5B7 antibody was pre-incubated with each peptide for 1 hour at room temperature before application to the tissue. A 1000-fold molar excess of peptide compared to antibody was used.

As shown in FIG. 7B, Peptide 1 resulted in partial inhibition of 5B7 binding, which indicated that part of the epitope was contained within Peptide 1. Peptide 2 resulted in complete inhibition of 5B7 binding, which indicated that the primary epitope was contained in Peptide 2. Logically, the three amino acids shared by Peptides 1 and 2 (i.e., QQD) must contain at least part of the full epitope. Peptide 3 also completely inhibited 5B7 binding; thus, the tyrosine did not significantly contribute to the 5B7 epitope. An average epitope is on the order of 7-12 contiguous amino acids; thus, the boxed residues in FIG. 7A represent a likely full-length 5B7 epitope with some possibility for an additional 1 to 5 residues at the C-terminal end.

Example 5

SOCS3 Knockout Unmasks Clone 5B7 Epitope

The L2G Peptide of the EGFR sequence is within the binding region for SOCS3 (Xia et al., *J. Biol. Chem.*, 277(34): 30716-23, 2002). Thus, it was postulated that SOCS3 may be masking the 5B7 epitope in some tissues. To test this hypothesis, livers from a hepatic-specific, SOCS3-knockout mouse were obtained from the laboratory that developed the model (Ogata et al., *Gastroenterology*, 131(1):179-93, 2006). Sections of formalin-fixed, paraffin-embedded livers from wild-type and SOCS3 mice were stained with clone 5B7 as described in Example 2.

Figure 8:
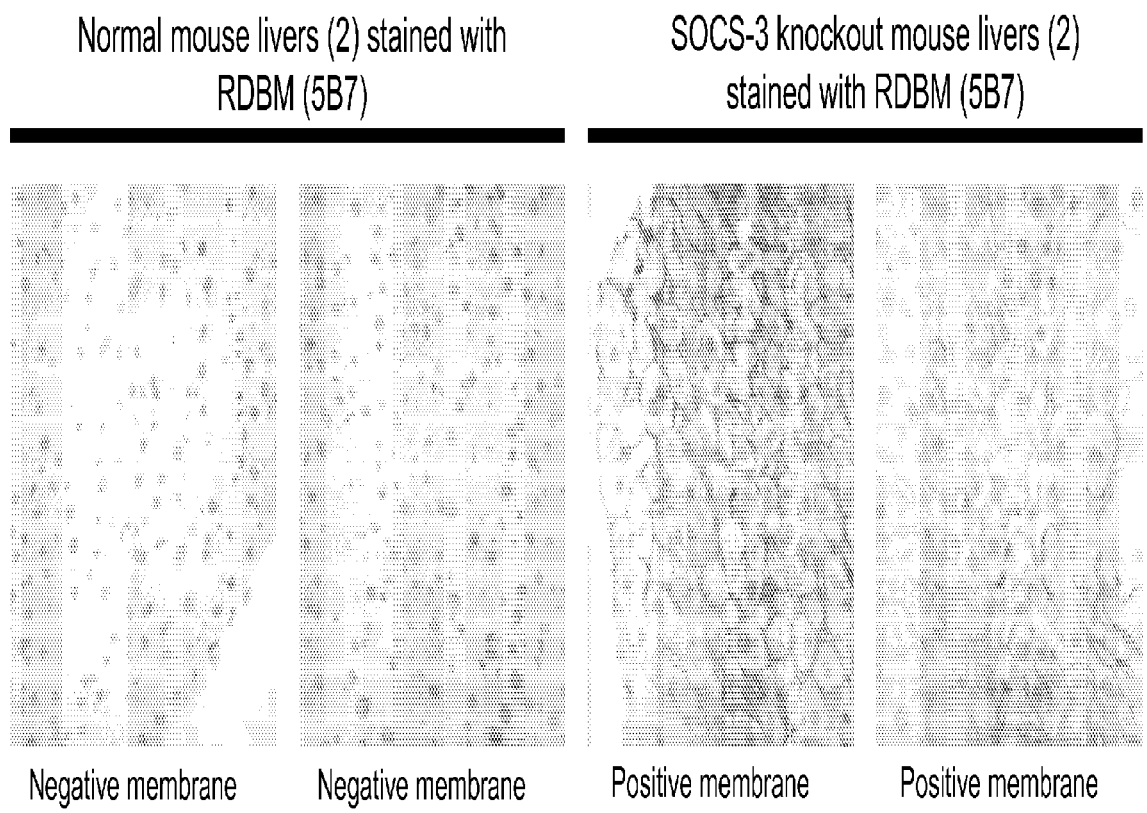
FIG. 8 shows images demonstrating the differences in the binding of EGFR regulatory-domain-specific (RDBM) clone 5B7 and EGFR external-domain-specific (EDBM) clone 3C6 in two normal mouse livers (left-most two panels) and the livers of SOCS3-knock-out mice (right-most two panels).

As shown in the left two panels of FIG. 8, 5B7 failed to stain normal liver, which expresses SOCS3. In comparison, as shown in the right two panels of FIG. 8, 5B7 positively stained the membranes of cells in livers lacking SOCS3. These results indicate that the loss or absence of SOCS3 allows for the binding of clone 5B7 to the regulatory domain of EGFR.

SOCS3 is only one example of a regulatory molecule that directly interacts with EGFR. The results demonstrated herein are widely applicable to other interface-specific binding molecules that have epitopes in the interface between two components of a molecular complex, such as between EGFR and its many regulatory proteins.

Example 6

EGFR RD-Binding Molecules, Such as Clone 5B7, Predict the Response of NSCLC Cancer Patients to EGFR-Inhibitor Therapy

This Example demonstrates that a disclosed RD-binding molecule (e.g., clone 5B7) predicts the response of NSCLC cancer patients to EGFR-inhibitor therapy (IRESSA™).

Tissue arrays containing biopsy samples from at least 100 NSCLC cancer patients are obtained. Each patient is treated with IRESSA™ (EGFR-inhibitor) therapy with a dosage of 250 mg/day given orally. Each patient has post-therapy follow-up for up to 5 years. Each biopsy sample is fixed in 10% NBF and paraffin embedded. Five (5) micron sections of each biopsy sample are cut and arrayed on positively charged glass slides. The slides are stained with an RD-binding molecule (e.g., clone 5B7) and an ED-binding molecule (e.g., clone 3C6) according to the protocols in Example 2. The resulting stained array slides are scored by light microscopy by a pathologist according to the following criteria:

category 3 and 15% in category 4. Patient outcome is directly related to the scoring category as indicated in Table 2 for an ID-based therapy. Patients in categories 1 and 3 will have an objective response to IRESSA™ therapy and patients in categories 2 and 4 will not significantly respond to IRESSA™ therapy.

Example 7

EGFR RD-Binding Molecules, Such as Clone 5B7, Predict the Response of NSCLC Cancer Patients to EGFR-Inhibitor Therapy

This Example demonstrates that a disclosed RD-binding molecule (e.g., clone 5B7) predicts the response of NSCLC cancer patients to EGFR-inhibitor therapy (TARCEVA™).

Tissue arrays containing biopsy samples from at least 100 NSCLC cancer patients are obtained. Each patient is treated with TARCEVA™ (EGFR inhibitor) therapy with a dosage of 150 mg/day given orally. Each patient has post-therapy follow-up for up to 5 years. Each biopsy sample is fixed in 10% NBF and paraffin embedded. Five (5) micron sections of each biopsy sample are cut and arrayed on positively charged glass

| Report Result | Staining Intensity Score | Microscope Observation |
|---|---|---|
| Positive: Any IHC staining of tumor cell membranes above background level whether it is complete or incomplete circumferential staining in more than 0% tumor cells | 3+ | Strong reactivity: Dark brown to black staining is usually, but not always, in a complete membrane pattern, producing a thick outline of the cell. Cytoplasmic reactivity may be absent or may be moderately intense when membrane staining is very intense. Submembranous cytoplasmic accentuation may be present. |
| | 2.5 | Intense reactivity: Shades of brown staining of medium darkness (intensity). Membranous reactivity is usually but not always complete, producing a circular outline of the neoplastic cell. Incomplete membrane reactivity of moderate intensity is also considered 2+. The cytoplasmic reactivity is of weaker intensity than the membrane reactivity. |
| | 2+ | Moderate reactivity: Shades of brown staining of intermediate darkness (intensity). Membranous reactivity is usually but not always complete, producing a circular outline of the neoplastic cell. Incomplete membrane reactivity of moderate intensity is also considered 2+. The cytoplasmic reactivity is of weaker intensity than the membrane reactivity. |
| | 1.5 | Slight reactivity: Staining of intermediate intensity that is membraneous. Cytoplasmic reactivity that is uniform and involves all the cytoplasm may be present, but should not be evaluated for positivity. |
| | 1+ | Weak reactivity: Faint or light brown reactivity that is membranous. Cytoplasmic reactivity that is uniform and involves all the cytoplasm may be present, but should not be evaluated for positivity. |
| Negative: Absence of membrane staining above background in all tumor cells. Presence of cytoplasmic in the absence of membrane staining. | 0.5 | Trace reactivity: Trace brown reactivity where membranous and cytoplasmic localization is indeterminate. |
| | 0 | No reactivity |

The score for each case is recorded in a database comparing the score for each binding molecule (e.g., 5B7 or 3C6). The result of each case is assigned to 1 of the 4 categories described in Table 2. Approximately 65% of cases are expected to fall into category 1, 19% in category 2, <1% in slides. The slides are stained with an RD-binding molecule (e.g., clone 5B7) and an ED-binding molecule (e.g., clone 3C6) according to the protocols in Example 2. The resulting stained array slides are scored by light microscopy by a pathologist according to the following criteria:

| Report Result | Staining Intensity Score | Microscope Observation |
|---|---|---|
| Positive: Any IHC staining of tumor cell membranes above background level whether it is complete or incomplete circumferential staining in more than 0% tumor cells | 3+ | Strong reactivity: Dark brown to black staining is usually, but not always, in a complete membrane pattern, producing a thick outline of the cell. Cytoplasmic reactivity may be absent or may be moderately intense when membrane staining is very intense. Submembranous cytoplasmic accentuation may be present. |
| | 2.5 | Intense reactivity: Shades of brown staining of medium darkness (intensity). Membranous reactivity is usually but not always complete, producing a circular outline of the neoplastic cell. Incomplete membrane reactivity of moderate intensity is also considered 2+. The cytoplasmic reactivity is of weaker intensity than the membrane reactivity. |
| | 2+ | Moderate reactivity: Shades of brown staining of intermediate darkness (intensity). Membranous reactivity is usually but not always complete, producing a circular outline of the neoplastic cell. Incomplete membrane reactivity of moderate intensity is also considered 2+. The cytoplasmic reactivity is of weaker intensity than the membrane reactivity. |
| | 1.5 | Slight reactivity: Staining of intermediate intensity that is membraneous. Cytoplasmic reactivity that is uniform and involves all the cytoplasm may be present, but should not be evaluated for positivity. |
| | 1+ | Weak reactivity: Faint or light brown reactivity that is membranous. Cytoplasmic reactivity that is uniform and involves all the cytoplasm may be present, but should not be evaluated for positivity. |
| Negative: Absence of membrane staining above background in all tumor cells. Presence of cytoplasmic in the absence of membrane staining. | 0.5 | Trace reactivity: Trace brown reactivity where membranous and cytoplasmic localization is indeterminate. |
| | 0 | No reactivity |

The score for each case is recorded in a database comparing the score for each binding molecule (e.g., 5B7 or 3C6). The result of each case is assigned to 1 of the 4 categories described in Table 2. Approximately 65% of cases are expected to fall into category 1, 19% in category 2, <1% in category 3 and 15% in category 4. Patient outcome is directly related to the scoring category as indicated in Table 2 for an ID-based therapy. Patients in categories 1 and 3 will have an objective response to TARCEVA™ therapy and Patients in categories 2 and 4 will not significantly respond to TARCEVA™ therapy.

Example 8

EGFR RD-Binding Molecules, Such as Clone 5B7, Predict the Response of Colorectal Cancer Patients to EGFR-Inhibitor Therapy This Example demonstrates that a disclosed RD-binding molecule (e.g., clone 5B7) predicts the response of colorectal cancer patients to EGFR-inhibitor therapy (ERBITUX™).

Tissue arrays containing biopsy samples from at least 100 colorectal cancer patients are obtained. Each patient is treated with ERBITUX™ (EGFR inhibitor) therapy with a dosage of 400 mg/m$^2$ given i.v. Each patient has post-therapy follow-up for up to 5 years. Each biopsy sample is fixed in 10% NBF and paraffin embedded. Five (5) micron sections of each biopsy sample are cut and arrayed on positively charged glass slides. The slides are stained with an RD-binding molecule (e.g., clone 5B7) and an ED-binding molecule (e.g., clone 3C6) according to the protocols in Example 2. The resulting stained array slides are scored by light microscopy by a pathologist according to the following criteria:

| Report Result | Staining Intensity Score | Microscope Observation |
|---|---|---|
| Positive: Any IHC staining of tumor cell membranes above background level whether it is complete or incomplete circumferential staining in more than 0% tumor cells | 3+ | Strong reactivity: Dark brown to black staining is usually, but not always, in a complete membrane pattern, producing a thick outline of the cell. Cytoplasmic reactivity may be absent or may be moderately intense when membrane staining is very intense. Submembranous cytoplasmic accentuation may be present. |
| | 2.5 | Intense reactivity: Shades of brown staining of medium darkness (intensity). Membranous reactivity is usually but not always complete, producing a circular outline of the neoplastic cell. Incomplete membrane reactivity of moderate intensity is also considered 2+. The cytoplasmic reactivity is of weaker intensity than the membrane reactivity. |

| Report Result | Staining Intensity Score | Microscope Observation |
|---|---|---|
| | 2+ | Moderate reactivity: Shades of brown staining of intermediate darkness (intensity). Membranous reactivity is usually but not always complete, producing a circular outline of the neoplastic cell. Incomplete membrane reactivity of moderate intensity is also considered 2+. The cytoplasmic reactivity is of weaker intensity than the membrane reactivity. |
| | 1.5 | Slight reactivity: Staining of intermediate intensity that is membraneous. Cytoplasmic reactivity that is uniform and involves all the cytoplasm may be present, but should not be evaluated for positivity. |
| | 1+ | Weak reactivity: Faint or light brown reactivity that is membranous. Cytoplasmic reactivity that is uniform and involves all the cytoplasm may be present, but should not be evaluated for positivity. |
| Negative: Absence of membrane staining above background in all tumor cells. Presence of cytoplasmic in the absence of membrane staining. | 0.5 | Trace reactivity: Trace brown reactivity where membranous and cytoplasmic localization is indeterminate. |
| | 0 | No reactivity |

The score for each case is recorded in a database comparing the score for each binding molecule (e.g., 5B7 or 3C6). The result of each case is assigned to 1 of the 4 categories described in Table 2. Approximately 65% of cases are expected to fall into category 1, 19% in category 2, <1% in category 3 and 15% in category 4. Patient outcome is directly related to the scoring category as indicated in Table 2 for an ED-based therapy. Patients in category 1 will have an objective response to ERBITUX™ therapy, and patients in categories 2, 3 and 4 will not significantly respond to ERBITUX™ therapy.

Example 9

EGFR RD-Binding Molecules, Such as Clone 5B7, Predict the Response of Colorectal Cancer Patients to EGFR-Inhibitor Therapy This Example demonstrates that a disclosed RD-binding molecule (e.g., clone 5B7) predicts the response of colorectal cancer patients to EGFR-inhibitor therapy (VECTIBIX™).

Tissue arrays containing biopsy samples from at least 100 colorectal cancer patients are obtained. Each patient is treated with VECTIBIX™ (EGFR inhibitor) therapy with a dosage of 6 mg/kg given i.v. Each patient has post-therapy follow-up for up to 5 years. Each biopsy sample is fixed in 10% NBF and paraffin embedded. Five (5) micron sections of each biopsy sample are cut and arrayed on positively charged glass slides. The slides are stained with an RD-binding molecule (e.g., clone 5B7) and an ED-binding molecule (e.g., clone 3C6) according to the protocols in Example 2. The resulting stained array slides are scored by light microscopy by a pathologist according to the following criteria:

| Report Result | Staining Intensity Score | Microscope Observation |
|---|---|---|
| Positive: Any IHC staining of tumor cell membranes above background level whether it is complete or incomplete circumferential staining in more than 0% tumor cells | 3+ | Strong reactivity: Dark brown to black staining is usually, but not always, in a complete membrane pattern, producing a thick outline of the cell. Cytoplasmic reactivity may be absent or may be moderately intense when membrane staining is very intense. Submembranous cytoplasmic accentuation may be present. |
| | 2.5 | Intense reactivity: Shades of brown staining of medium darkness (intensity). Membranous reactivity is usually but not always complete, producing a circular outline of the neoplastic cell. Incomplete membrane reactivity of moderate intensity is also considered 2+. The cytoplasmic reactivity is of weaker intensity than the membrane reactivity. |
| | 2+ | Moderate reactivity: Shades of brown staining of intermediate darkness (intensity). Membranous reactivity is usually but not always complete, producing a circular outline of the neoplastic cell. Incomplete membrane reactivity of moderate intensity is also considered 2+. The cytoplasmic reactivity is of weaker intensity than the membrane reactivity. |
| | 1.5 | Slight reactivity: Staining of intermediate intensity that is membraneous. Cytoplasmic reactivity that is uniform and involves all the cytoplasm may be present, but should not be evaluated for positivity. |

| Report Result | Staining Intensity Score | Microscope Observation |
|---|---|---|
| | 1+ | Weak reactivity: Faint or light brown reactivity that is membranous. Cytoplasmic reactivity that is uniform and involves all the cytoplasm may be present, but should not be evaluated for positivity. |
| Negative: Absence of membrane staining above background in all tumor cells. Presence of cytoplasmic in the absence of membrane staining. | 0.5 | Trace reactivity: Trace brown reactivity where membranous and cytoplasmic localization is indeterminate. |
| | 0 | No reactivity |

The score for each case is recorded in a database comparing the score for each binding molecule (e.g., 5B7 or 3C6). The result of each case is assigned to 1 of the 4 categories described in Table 2. Approximately 65% of cases are expected to fall into category 1, 19% in category 2, <1% in category 3 and 15% in category 4. Patient outcome is directly related to the scoring category as indicated in Table 2 for an ED-based therapy. Patients in category 1 will have an objective response to VECTIBIX™ therapy and, patients in categories 2, 3 and 4 will not significantly respond to VECTIBIX™ therapy.

Example 10

EGFR RD-Binding Molecules, Such as Clone 5B7, Predict the Response of Breast Cancer Patients to EGFR-Inhibitor Therapy This Example demonstrates that a disclosed RD-binding molecule (e.g., clone 5B7) predicts the response of breast cancer patients to EGFR-inhibitor therapy or, more particularly, HER1 (EGFR)/HER2-inhibitor therapy (such as, lapatinib (TYKERB™)).

Tissue arrays containing biopsy samples from at least 100 breast cancer patients are obtained. Each patient is treated with lapatinib (TYKERB™) (HER1 (EGFR)/HER2-inhibitor) with a dosage of 1250-1500 mg/day given orally. Each patient has post-therapy follow-up for at least 20 months. Each biopsy sample is fixed in a standard fixative and paraffin embedded. Sections of each biopsy sample (e.g., 5 μm thick) are cut and arrayed on positively charged glass slides. The slides are stained with an RD-binding molecule (e.g., clone 5B7) and an ED-binding molecule (e.g., clone 3C6) according to the protocols in Example 2. The resulting stained array slides are scored by light microscopy by a pathologist according to the following criteria:

| Report Result | Staining Intensity Score | Microscope Observation |
|---|---|---|
| Positive: Any IHC staining of tumor cell membranes above background level whether it is complete or incomplete circumferential staining in more than 0% tumor cells | 3+ | Strong reactivity: Dark brown to black staining is usually, but not always, in a complete membrane pattern, producing a thick outline of the cell. Cytoplasmic reactivity may be absent or may be moderately intense when membrane staining is very intense. Submembranous cytoplasmic accentuation may be present. |
| | 2.5 | Intense reactivity: Shades of brown staining of medium darkness (intensity). Membranous reactivity is usually but not always complete, producing a circular outline of the neoplastic cell. Incomplete membrane reactivity of moderate intensity is also considered 2+. The cytoplasmic reactivity is of weaker intensity than the membrane reactivity. |
| | 2+ | Moderate reactivity: Shades of brown staining of intermediate darkness (intensity). Membranous reactivity is usually but not always complete, producing a circular outline of the neoplastic cell. Incomplete membrane reactivity of moderate intensity is also considered 2+. The cytoplasmic reactivity is of weaker intensity than the membrane reactivity. |
| | 1.5 | Slight reactivity: Staining of intermediate intensity that is membraneous. Cytoplasmic reactivity that is uniform and involves all the cytoplasm may be present, but should not be evaluated for positivity. |
| | 1+ | Weak reactivity: Faint or light brown reactivity that is membranous. Cytoplasmic reactivity that is uniform and involves all the cytoplasm may be present, but should not be evaluated for positivity. |
| Negative: Absence of membrane staining above background in all tumor cells. Presence of cytoplasmic in the absence of membrane staining. | 0.5 | Trace reactivity: Trace brown reactivity where membranous and cytoplasmic localization is indeterminate. |
| | 0 | No reactivity |

The score for each case is recorded in a database comparing the score for each binding molecule (e.g., 5B7 or 3C6). The result of each case is assigned to 1 of the 4 categories described in Table 2. Approximately 20% of cases are expected to fall into category 1, 16% in category 2, 3% in category 3 and 61% in category 4. Patient outcome is directly related to the scoring category as indicated in Table 2 for an ID-based therapy. Patients in categories 1 and 3 will have an objective response to lapatinib (TYKERB™) therapy and Patients in categories 2 and 4 will not significantly respond to lapatinib (TYKERB™) therapy.

Example 11

EGFR RD-Binding Molecules, Such as Clone 5B7, Predict the Response of Hepatocellular Carcinoma Cancer Patients to EGFR-Inhibitor Therapy This Example demonstrates that a disclosed RD-binding molecule (e.g., clone 5B7) predicts the response of hepatocellular carcinoma ("HCC") (such as, resectable HCC) cancer patients to EGFR-inhibitor therapy (IRESSA™).

Tissue arrays containing biopsy samples from at least 100 HCC cancer patients are obtained (see, for example, samples collected in JS 0414, "A Pilot Study of Adjuvant Therapy of Gefitinib (Iressa, ZD1839) in Patients with Resectable Hepatocellular Carcinoma", ClinicalTrials.gov Identifier No. NCT00228501). Each patient is treated with IRESSA™ (EGFR-inhibitor) therapy with a dosage of 200-500 mg/day given orally. Each patient has post-therapy follow-up for at least 12 months. Each biopsy sample is fixed in a standard fixative (e.g., 10% NBF) and paraffin embedded. Sections of each biopsy sample (e.g., 5 μm thick) are cut and arrayed on positively charged glass slides. The slides are stained with an RD-binding molecule (e.g., clone 5B7) and an ED-binding molecule (e.g., clone 3C6) according to the protocols in Example 2. The resulting stained array slides are scored by light microscopy by a pathologist according to the following criteria:

| Report Result | Staining Intensity Score | Microscope Observation |
|---|---|---|
| Positive: Any IHC staining of tumor cell membranes above background level whether it is complete or incomplete circumferential staining in more than 0% tumor cells | 3+ | Strong reactivity: Dark brown to black staining is usually, but not always, in a complete membrane pattern, producing a thick outline of the cell. Cytoplasmic reactivity may be absent or may be moderately intense when membrane staining is very intense. Submembranous cytoplasmic accentuation may be present. |
| | 2.5 | Intense reactivity: Shades of brown staining of medium darkness (intensity). Membranous reactivity is usually but not always complete, producing a circular outline of the neoplastic cell. Incomplete membrane reactivity of moderate intensity is also considered 2+. The cytoplasmic reactivity is of weaker intensity than the membrane reactivity. |
| | 2+ | Moderate reactivity: Shades of brown staining of intermediate darkness (intensity). Membranous reactivity is usually but not always complete, producing a circular outline of the neoplastic cell. Incomplete membrane reactivity of moderate intensity is also considered 2+. The cytoplasmic reactivity is of weaker intensity than the membrane reactivity. |
| | 1.5 | Slight reactivity: Staining of intermediate intensity that is membraneous. Cytoplasmic reactivity that is uniform and involves all the cytoplasm may be present, but should not be evaluated for positivity. |
| | 1+ | Weak reactivity: Faint or light brown reactivity that is membranous. Cytoplasmic reactivity that is uniform and involves all the cytoplasm may be present, but should not be evaluated for positivity. |
| Negative: Absence of membrane staining above background in all tumor cells. Presence of cytoplasmic in the absence of membrane staining. | 0.5 | Trace reactivity: Trace brown reactivity where membranous and cytoplasmic localization is indeterminate. |
| | 0 | No reactivity |

The score for each case is recorded in a database comparing the score for each binding molecule (e.g., 5B7 or 3C6). The result of each case is assigned to 1 of the 4 categories described in Table 2. Approximately 60% of cases are expected to fall into category 1, 13% in category 2, 5% in category 3 and 22% in category 4. Patient outcome is directly related to the scoring category as indicated in Table 2 for an ID-based therapy. Patients in categories 1 and 3 will have an objective response to IRESSA™ therapy and patients in categories 2 and 4 will not significantly respond to IRESSA™ therapy.

Example 12

Clone 5B7 Status is a Clear Indicator of Lung Cancer Prognosis

This Example demonstrates that clone 5B7 predicts the prognosis of lung cancer patients.

A tissue array containing lung biopsy samples from 109 Stage I or II NSCLC patients was obtained (a subset of the larger cohort described in Olaussen et al., New Engl. J. Med., 355(10):983-991, 2006). None of the patients from whom the biopsies were obtained had been treated with an EGFR-based therapy (e.g., ERBITUX™, VECTIBIX™, IRESSA™, or TARCEVA™). Patient survival post-diagnosis was monitored on a continuing basis. Each biopsy sample was paraffin embedded, cancerous areas in the biopsy were identified, a core of the cancerous area removed, and placed in a donor array paraffin block. Three to five micron sections of the donor array block were cut and mounted on glass slides. Slides containing serial sections of the donor array block were stained with clone 5B7 or clone 3C6 according to the protocols in Example 2. The resulting stained slides are scored by light microscopy by a pathologist according to the following criteria:

| Report Result | Staining Intensity Score | Microscope Observation |
|---|---|---|
| Positive: Any IHC staining of tumor cell membranes above background level whether it is complete or incomplete circumferential staining in more than 0% tumor cells | 3+ | Strong reactivity: Dark brown to black staining is usually, but not always, in a complete membrane pattern, producing a thick outline of the cell. Cytoplasmic reactivity may be absent or may be moderately intense when membrane staining is very intense. Submembranous cytoplasmic accentuation may be present. |
| | 2.5 | Intense reactivity: Shades of brown staining of medium darkness (intensity). Membranous reactivity is usually but not always complete, producing a circular outline of the neoplastic cell. Incomplete membrane reactivity of moderate intensity is also considered 2+. The cytoplasmic reactivity is of weaker intensity than the membrane reactivity. |
| | 2+ | Moderate reactivity: Shades of brown staining of intermediate darkness (intensity). Membranous reactivity is usually but not always complete, producing a circular outline of the neoplastic cell. Incomplete membrane reactivity of moderate intensity is also considered 2+. The cytoplasmic reactivity is of weaker intensity than the membrane reactivity. |
| | 1.5 | Slight reactivity: Staining of intermediate intensity that is membraneous. Cytoplasmic reactivity that is uniform and involves all the cytoplasm may be present, but should not be evaluated for positivity. |
| | 1+ | Weak reactivity: Faint or light brown reactivity that is membranous. Cytoplasmic reactivity that is uniform and involves all the cytoplasm may be present, but should not be evaluated for positivity. |
| Negative: Absence of membrane staining above background in all tumor cells. Presence of cytoplasmic in the absence of membrane staining. | 0.5 | Trace reactivity: Trace brown reactivity where membranous and cytoplasmic localization is indeterminate. |
| | 0 | No reactivity |

The score for each biopsy sample and the associated follow-up is shown in the following table:

| Sample Number | 3C6 Score | 5B7 Score | Months at Recurrence | Months at Death |
|---|---|---|---|---|
| P003 | 2 | 2 | None | None |
| P005 | 2.5 | 0.5 | 35 | 36 |
| P006 | 0 | 2 | 6 | 36 |
| P007 | 0 | 2 | None | None |
| P008 | 0 | 1 | 5 | 25 |
| P010 | 3 | 0.5 | None | None |
| P011 | 2.5 | 0.5 | 42 | 57 |
| P012 | 2.5 | 2 | None | None |
| P014 | 2 | 2.5 | 70 | None |
| P015 | 0 | 1 | None | None |
| P016 | 1 | 1 | None | None |
| P017 | 2.5 | 2 | 17 | 33 |
| P018 | 2.5 | 2 | None | None |
| P019 | 3 | 2 | None | None |
| P020 | 0.5 | 1 | None | None |
| P022 | 2 | 1.5 | None | None |
| P023 | 0 | 2 | 17 | None |
| P024 | 0 | 0.5 | None | None |
| P025 | 0 | 2.5 | None | None |
| P026 | 0 | 2.5 | 16 | 94 |
| P029 | 0.5 | 1 | 47 | 24 |
| P030 | 0 | 2 | None | None |
| P031 | 2 | 1.5 | 36 | 70 |
| P033 | 3 | 2 | None | None |
| P037 | 0.5 | 4.5 | None | 96 |
| P039 | 0 | 1 | None | None |
| P041 | 0.5 | 1.5 | None | None |
| P042 | 1 | 0 | None | None |
| P044 | 1 | 1 | None | None |
| P047 | 0 | 2 | 8 | 25 |
| P050 | 1.5 | 0 | None | None |
| P051 | 2.5 | 0.5 | None | None |
| P057 | 1 | 0 | 90 | None |
| P058 | 0 | 0.5 | None | None |
| P061 | 2 | 1 | None | None |
| P063 | 1.5 | 3 | None | None |
| P064 | 1.5 | 2.5 | 65 | None |
| P065 | 0 | 1.5 | None | None |
| P066 | 0.5 | 0.5 | None | None |
| P068 | 3 | 1 | None | None |
| P070 | 1 | 1 | 5 | 7 |
| P071 | 0.5 | 3 | 15 | 18 |
| P072 | 3 | 2 | 22 | 25 |
| P073 | 1 | 0.5 | 68 | None |
| P074 | 2.5 | 0 | None | None |
| P076 | 2 | 0.5 | None | None |
| P078 | 3 | 1.5 | None | None |
| P080 | 0.5 | 3 | None | None |
| P161 | 0 | 0 | None | None |
| P162 | 2 | 2 | None | None |
| P163 | 2 | 1 | None | None |
| P165 | 1 | 1 | None | None |
| P167 | 0.5 | 1.5 | None | None |
| P168 | 3 | 3 | None | None |
| P169 | 2.5 | 2.5 | None | None |
| P170 | 2 | 2.5 | None | None |
| P171 | 1 | 1 | None | None |
| P172 | 0 | 0.5 | 19 | 28 |
| P173 | 0 | 1 | None | None |
| P174 | 2 | 2 | None | None |
| P175 | 0.5 | 2 | None | None |
| P176 | 0.5 | 0.5 | None | None |
| P177 | 0.5 | 2 | None | None |
| P178 | 2 | 2 | None | None |
| P179 | 3 | 2.5 | None | None |
| P180 | 1.5 | 1 | None | None |
| P181 | 2.5 | 2.5 | None | None |
| P182 | 3 | 3 | None | None |
| P184 | 3 | 3 | 16 | 44 |

-continued

| Sample Number | 3C6 Score | 5B7 Score | Months at Recurrence | Months at Death |
|---|---|---|---|---|
| P187 | 2 | 2.5 | None | None |
| P188 | 1 | 1 | None | None |
| P189 | 0 | 1 | 17 | None |
| P190 | 3 | 3 | 17 | 44 |
| P194 | 1.5 | 3 | None | None |
| P197 | 0 | 1 | None | None |
| P200 | 1 | 0.5 | None | None |
| P202 | 3 | 3 | 8 | 20 |
| P203 | 1.5 | 2 | 9 | 15 |
| P207 | 1 | 2.5 | None | None |
| P209 | 2.5 | 2.5 | None | None |
| P210 | 2 | 1 | None | None |
| P211 | 2 | 3 | 4 | 5 |
| P212 | 1 | 1.5 | None | None |
| P213 | 3 | 3 | 29 | None |
| P214 | 2 | 2.5 | None | None |
| P216 | 3 | 3 | 15 | 21 |
| P217 | 3 | 3 | 19 | None |
| P219 | 2 | 2 | None | None |
| P220 | 2 | 2 | None | None |
| P221 | 0 | 0.5 | None | None |
| P222 | 0 | 1 | 6 | 12 |
| P223 | 0 | 0.5 | None | None |
| P224 | 3 | 2.5 | 24 | 53 |
| P225 | 0 | 1 | None | None |
| P226 | 1.5 | 2 | 5 | 9 |
| P227 | 0.5 | 1.5 | None | None |
| P228 | 1 | 2.5 | None | None |
| P230 | 1.5 | 1.5 | None | None |
| P231 | 1 | 2 | None | None |
| P232 | 0 | 0.5 | None | None |

As shown in FIG. 9A, clone 3C6 staining (whether negative or positive) has no correlation to NSCLC patient overall survivability while clone 5B7 clearly delineates two populations. In particular, positive 5B7 staining (score=1 or greater) identified NSCLC patients (n=80) having poor survivability, and negative 5B7 staining (score<1) identified NSCLC patients (n=20) with greater survivability (FIG. 9B). For example, as shown in FIG. 9B, approximately 82% of patients whose biopsy sample stained negative for clone 5B7 were still surviving at 8.3 years post-diagnosis. In comparison, approximately 65% of patients whose biopsy sample stained positive for clone 5B7 were surviving at the same time point.

Figure 10A:
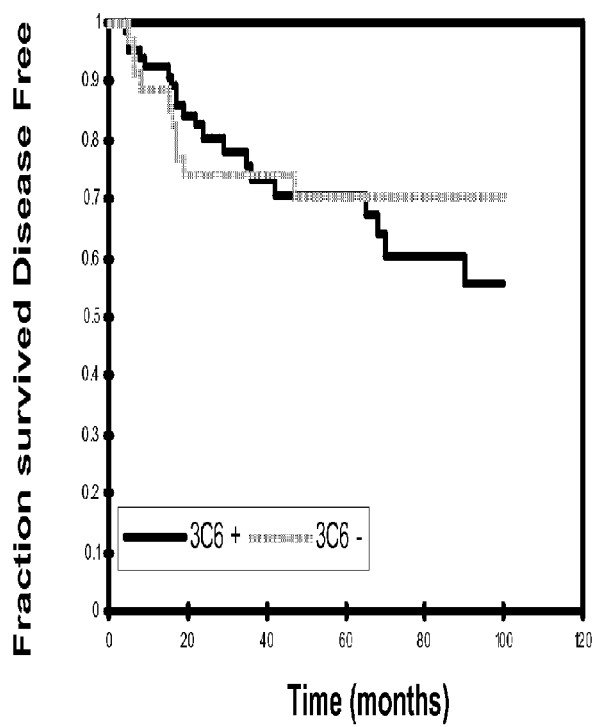
Figure 10B:
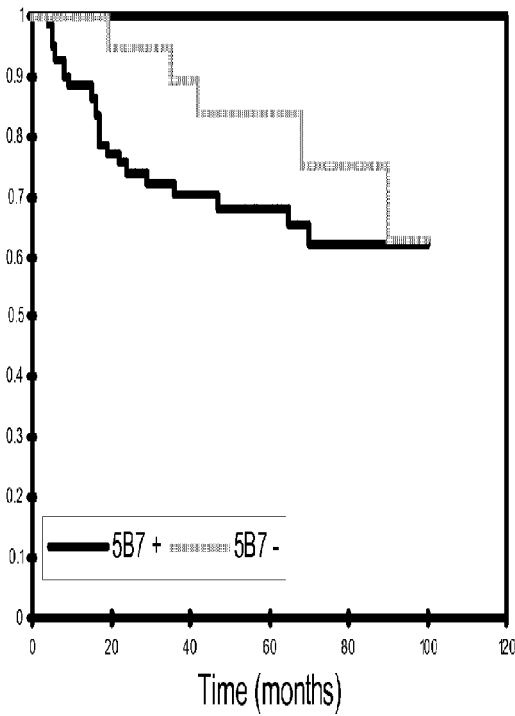

As shown in FIG. 10A, clone 3C6 staining (whether negative or positive) has no correlation to NSCLC patient disease-free survival (DFS) while clone 5B7 clearly delineates two populations. In particular, positive 5B7 staining (score=1 or greater) identified NSCLC patients (n=80) having poor DFS, and negative 5B7 staining (score<1) identified NSCLC patients (n=20) with greater DFS. For example, as shown in FIG. 10B, approximately 75% of patients whose biopsy sample stained negative for clone 5B7 were still surviving at 6 years post-diagnosis. In comparison, approximately 62% of patients whose biopsy sample stained positive for clone 5B7 were surviving at the same time point. The 5B7-positive and 5B7-negative curves converge around 90 months post-diagnosis most likely due to a statistical artifact cause by a decrease in the number of 5B7-negative samples at that (and later) time points. It is expected that 5B7-negative NSCLC patients will continue to have a better prognosis at 90 months and beyond when an even larger patient cohort is examined.

This Example demonstrates that EGFR RD-binding molecules, such as clone 5B7, predict the prognosis (e.g., overall survival and/or disease-free survival) of NSCLC patients (e.g., early stage NSCLC patients) independent of treatment.

Example 13

EGFR RD-Binding Molecules, Such as Clone 5B7, are Indicators of Colorectal Cancer Prognosis This Example demonstrates that a disclosed RD-binding molecule (e.g., clone 5B7) predicts the prognosis of colorectal cancer patients.

Tissue arrays containing biopsy samples from at least 100 colorectal cancer patients are obtained. Each patient preferably will not have been treated with an EGFR-based therapy (e.g., ERBITUX™, VECTIBIX™, IRESSA™, or TARCEVA™). Each patient is followed for up to 5 years post-diagnosis. Each biopsy sample is fixed in 10% NBF and paraffin embedded. Five (5) micron sections of each biopsy sample are cut and arrayed on positively charged glass slides. The slides are stained with an RD-binding molecule (e.g., clone 5B7) and an ED-binding molecule (e.g., clone 3C6) according to the protocols in Example 2. The resulting stained array slides are scored by light microscopy by a pathologist according to the following criteria:

| Report Result | Staining Intensity Score | Microscope Observation |
|---|---|---|
| Positive: Any IHC staining of tumor cell membranes above background level whether it is complete or incomplete circumferential staining in more than 0% tumor cells | 3+ | Strong reactivity: Dark brown to black staining is usually, but not always, in a complete membrane pattern, producing a thick outline of the cell. Cytoplasmic reactivity may be absent or may be moderately intense when membrane staining is very intense. Submembranous cytoplasmic accentuation may be present. |
| | 2.5 | Intense reactivity: Shades of brown staining of medium darkness (intensity). Membranous reactivity is usually but not always complete, producing a circular outline of the neoplastic cell. Incomplete membrane reactivity of moderate intensity is also considered 2+. The cytoplasmic reactivity is of weaker intensity than the membrane reactivity. |
| | 2+ | Moderate reactivity: Shades of brown staining of intermediate darkness (intensity). Membranous reactivity is usually but not always complete, producing a circular outline of the neoplastic cell. Incomplete membrane reactivity of moderate intensity is also considered 2+. The cytoplasmic reactivity is of weaker intensity than the membrane reactivity. |
| | 1.5 | Slight reactivity: Staining of intermediate intensity that is membraneous. Cytoplasmic reactivity that is uniform and involves all the cytoplasm may be present, but should not be evaluated for positivity. |

-continued

| Report Result | Staining Intensity Score | Microscope Observation |
|---|---|---|
| | 1+ | Weak reactivity: Faint or light brown reactivity that is membranous. Cytoplasmic reactivity that is uniform and involves all the cytoplasm may be present, but should not be evaluated for positivity. |
| Negative: Absence of membrane staining above background in all tumor cells. Presence of cytoplasmic in the absence of membrane staining. | 0.5 | Trace reactivity: Trace brown reactivity where membranous and cytoplasmic localization is indeterminate. |
| | 0 | No reactivity |

The score for each case is recorded in a database comparing the score for each binding molecule (e.g., 5B7 and 3C6). The results of each case will fall into one of the 4 categories described in Table 2. Approximately 65% of cases are expected to fall into category 1, 19% in category 2, <1% in category 3 and 15% in category 4. Patient outcome will be directly related to the scoring category as indicated in FIG. 3 and Table 2. Patients in category 1 and 3 will have a poor prognosis, and patients in categories 2 and 4 will have a better prognosis.

Example 14

EGFR RD-Binding Molecules, Such as Clone 5B7, are Indicators of Head and Neck Cancer Prognosis This Example demonstrates that a disclosed RD-binding molecule (e.g., clone 5B7) predicts the prognosis of head and neck cancer patients.

Tissue arrays containing biopsy samples from at least 100 head and neck cancer patients are obtained. Each patient preferably will not have been treated with an EGFR-based therapy (e.g., ERBITUX™, VECTIBIX™, IRESSA™, or TARCEVA™). Each patient is followed for up to 5 years post-diagnosis. Each biopsy sample is fixed in 10% NBF and paraffin embedded. Five (5) micron sections of each biopsy sample are cut and arrayed on positively charged glass slides. The slides are stained with an RD-binding molecule (e.g., clone 5B7) and an ED-binding molecule (e.g., clone 3C6) according to the protocols in Example 2. The resulting stained array slides are scored by light microscopy by a pathologist according to the following criteria:

| Report Result | Staining Intensity Score | Microscope Observation |
|---|---|---|
| Positive: Any IHC staining of tumor cell membranes above background level whether it is complete or incomplete circumferential staining in more than 0% tumor cells | 3+ | Strong reactivity: Dark brown to black staining is usually, but not always, in a complete membrane pattern, producing a thick outline of the cell. Cytoplasmic reactivity may be absent or may be moderately intense when membrane staining is very intense. Submembranous cytoplasmic accentuation may be present. |
| | 2.5 | Intense reactivity: Shades of brown staining of medium darkness (intensity). Membranous reactivity is usually but not always complete, producing a circular outline of the neoplastic cell. Incomplete membrane reactivity of moderate intensity is also considered 2+. The cytoplasmic reactivity is of weaker intensity than the membrane reactivity. |
| | 2+ | Moderate reactivity: Shades of brown staining of intermediate darkness (intensity). Membranous reactivity is usually but not always complete, producing a circular outline of the neoplastic cell. Incomplete membrane reactivity of moderate intensity is also considered 2+. The cytoplasmic reactivity is of weaker intensity than the membrane reactivity. |
| | 1.5 | Slight reactivity: Staining of intermediate intensity that is membraneous. Cytoplasmic reactivity that is uniform and involves all the cytoplasm may be present, but should not be evaluated for positivity. |
| | 1+ | Weak reactivity: Faint or light brown reactivity that is membranous. Cytoplasmic reactivity that is uniform and involves all the cytoplasm may be present, but should not be evaluated for positivity. |
| Negative: Absence of membrane staining above background in all tumor cells. Presence of cytoplasmic in the absence of membrane staining. | 0.5 | Trace reactivity: Trace brown reactivity where membranous and cytoplasmic localization is indeterminate. |
| | 0 | No reactivity |

The score for each case is recorded in a database comparing the score for each binding molecule (e.g., 5B7 and 3C6). The results of each case will fall into one of the 4 categories described in Table 2. Approximately 65% of cases are expected to fall into category 1, 19% in category 2, <1% in category 3 and 15% in category 4. Patient outcome will be directly related to the scoring category as indicated in FIG. 3 and Table 2. Patients in category 1 and 3 will have a poor prognosis, and patients in categories 2 and 4 will have a better prognosis.

Example 15

EGFR RD-Binding Molecules, Such as Clone 5B7, are Indicators of Gastric Cancer Prognosis This Example demonstrates that a disclosed RD-binding molecule (e.g., clone 5B7) predicts the prognosis of gastric cancer patients.

Tissue arrays containing biopsy samples from at least 100 gastric cancer patients are obtained. Each patient preferably will not have been treated with an EGFR-based therapy (e.g., ERBITUX™, VECTIBIX™, IRESSA™, or TARCEVA™). Each patient is followed for up to 5 years post-diagnosis. Each biopsy sample is fixed in 10% NBF and paraffin embedded. Five (5) micron sections of each biopsy sample are cut and arrayed on positively charged glass slides. The slides are stained with an RD-binding molecule (e.g., clone 5B7) and an ED-binding molecule (e.g., clone 3C6) according to the protocols in Example 2. The resulting stained array slides are scored by light microscopy by a pathologist according to the following criteria:

Example 16

EGFR RD-Binding Molecules, Such as Clone 5B7, are Indicators of Glioblastoma Cancer Prognosis This Example demonstrates that a disclosed RD-binding molecule (e.g., clone 5B7) predicts the prognosis of glioblastoma cancer patients.

Tissue arrays containing biopsy samples from at least 100 glioblastoma cancer patients are obtained. Each patient preferably will not have been treated with an EGFR-based therapy (e.g., ERBITUX™, VECTIBIX™, IRESSA™, or TARCEVA™). Each patient is followed for up to 5 years post-diagnosis. Each biopsy sample is fixed in 10% NBF and paraffin embedded. Five (5) micron sections of each biopsy sample are cut and arrayed on positively charged glass slides. The slides are stained with an RD-binding molecule (e.g., clone 5B7) and an ED-binding molecule (e.g., clone 3C6) according to the protocols in Example 2. The resulting stained array slides are scored by light microscopy by a pathologist according to the following criteria:

| Report Result | Staining Intensity Score | Microscope Observation |
|---|---|---|
| Positive: Any IHC staining of tumor cell membranes above background level whether it is complete or incomplete circumferential staining in more than 0% tumor cells | 3+ | Strong reactivity: Dark brown to black staining is usually, but not always, in a complete membrane pattern, producing a thick outline of the cell. Cytoplasmic reactivity may be absent or may be moderately intense when membrane staining is very intense. Submembranous cytoplasmic accentuation may be present. |
|  | 2.5 | Intense reactivity: Shades of brown staining of medium darkness (intensity). Membranous reactivity is usually but not always complete, producing a circular outline of the neoplastic cell. Incomplete membrane reactivity of moderate intensity is also considered 2+. The cytoplasmic reactivity is of weaker intensity than the membrane reactivity. |
|  | 2+ | Moderate reactivity: Shades of brown staining of intermediate darkness (intensity). Membranous reactivity is usually but not always complete, producing a circular outline of the neoplastic cell. Incomplete membrane reactivity of moderate intensity is also considered 2+. The cytoplasmic reactivity is of weaker intensity than the membrane reactivity. |
|  | 1.5 | Slight reactivity: Staining of intermediate intensity that is membraneous. Cytoplasmic reactivity that is uniform and involves all the cytoplasm may be present, but should not be evaluated for positivity. |
|  | 1+ | Weak reactivity: Faint or light brown reactivity that is membranous. Cytoplasmic reactivity that is uniform and involves all the cytoplasm may be present, but should not be evaluated for positivity. |
| Negative: Absence of membrane staining above background in all tumor cells. Presence of cytoplasmic in the absence of membrane staining. | 0.5 | Trace reactivity: Trace brown reactivity where membranous and cytoplasmic localization is indeterminate. |
|  | 0 | No reactivity |

| Report Result | Staining Intensity Score | Microscope Observation |
| --- | --- | --- |
| Positive: Any IHC staining of tumor cell membranes above background level whether it is complete or incomplete circumferential staining in more than 0% tumor cells | 3+ | Strong reactivity: Dark brown to black staining is usually, but not always, in a complete membrane pattern, producing a thick outline of the cell. Cytoplasmic reactivity may be absent or may be moderately intense when membrane staining is very intense. Submembranous cytoplasmic accentuation may be present. |
| | 2.5 | Intense reactivity: Shades of brown staining of medium darkness (intensity). Membranous reactivity is usually but not always complete, producing a circular outline of the neoplastic cell. Incomplete membrane reactivity of moderate intensity is also considered 2+. The cytoplasmic reactivity is of weaker intensity than the membrane reactivity. |
| | 2+ | Moderate reactivity: Shades of brown staining of intermediate darkness (intensity). Membranous reactivity is usually but not always complete, producing a circular outline of the neoplastic cell. Incomplete membrane reactivity of moderate intensity is also considered 2+. The cytoplasmic reactivity is of weaker intensity than the membrane reactivity. |
| | 1.5 | Slight reactivity: Staining of intermediate intensity that is membraneous. Cytoplasmic reactivity that is uniform and involves all the cytoplasm may be present, but should not be evaluated for positivity. |
| | 1+ | Weak reactivity: Faint or light brown reactivity that is membranous. Cytoplasmic reactivity that is uniform and involves all the cytoplasm may be present, but should not be evaluated for positivity. |
| Negative: Absence of membrane staining above background in all tumor cells. Presence of cytoplasmic in the absence of membrane staining. | 0.5 | Trace reactivity: Trace brown reactivity where membranous and cytoplasmic localization is indeterminate. |
| | 0 | No reactivity |

The score for each case is recorded in a database comparing the score for each binding molecule (e.g., 5B7 and 3C6). The results of each case will fall into one of the 4 categories described in Table 2. Approximately 65% of cases are expected to fall into category 1, 19% in category 2, <1% in category 3 and 15% in category 4. Patient outcome will be directly related to the scoring category as indicated in FIG. 3 and Table 2. Patients in category 1 and 3 will have a poor prognosis, and patients in categories 2 and 4 will have a better prognosis.

Example 17

EGFR RD-Binding Molecules, Such as Clone 5B7, are Indicators of Hepatocellular Carcinoma Prognosis This Example demonstrates that a disclosed RD-binding molecule (e.g., clone 5B7) predicts the prognosis of HCC (such as, resectable HCC) cancer patients Tissue arrays containing biopsy samples from at least 100 HCC cancer patients are obtained (see, for example, control arm of samples collected in JS 0414, "A Pilot Study of Adjuvant Therapy of Gefitinib (Iressa, ZD1839) in Patients with Resectable Hepatocellular Carcinoma", ClinicalTrials.gov Identifier No. NCT00228501). Each patient preferably will not have been treated with an EGFR-based therapy (e.g., ERBITUX™, VECTIBIX™, IRESSA™, or TARCEVA™). Each patient is followed for up to 5 years post-diagnosis. Each biopsy sample is fixed in a standard fixative (e.g., 10% NBF) and paraffin embedded. Sections of each biopsy sample (e.g., 5 μm thick) are cut and arrayed on positively charged glass slides. The slides are stained with an RD-binding molecule (e.g., clone 5B7) and an ED-binding molecule (e.g., clone 3C6) according to the protocols in Example 2. The resulting stained array slides are scored by light microscopy by a pathologist according to the following criteria:

| Report Result | Staining Intensity Score | Microscope Observation |
| --- | --- | --- |
| Positive: Any IHC staining of tumor cell membranes above background level whether it is complete or incomplete circumferential staining in more than 0% tumor cells | 3+ | Strong reactivity: Dark brown to black staining is usually, but not always, in a complete membrane pattern, producing a thick outline of the cell. Cytoplasmic reactivity may be absent or may be moderately intense when membrane staining is very intense. Submembranous cytoplasmic accentuation may be present. |
| | 2.5 | Intense reactivity: Shades of brown staining of medium darkness (intensity). Membranous reactivity is usually but not always complete, producing a circular outline of the neoplastic cell. Incomplete membrane reactivity of moderate intensity is also considered 2+. The cytoplasmic reactivity is of weaker intensity than the membrane reactivity. |

| Report Result | Staining Intensity Score | Microscope Observation |
|---|---|---|
| | 2+ | Moderate reactivity: Shades of brown staining of intermediate darkness (intensity). Membranous reactivity is usually but not always complete, producing a circular outline of the neoplastic cell. Incomplete membrane reactivity of moderate intensity is also considered 2+. The cytoplasmic reactivity is of weaker intensity than the membrane reactivity. |
| | 1.5 | Slight reactivity: Staining of intermediate intensity that is membraneous. Cytoplasmic reactivity that is uniform and involves all the cytoplasm may be present, but should not be evaluated for positivity. |
| | 1+ | Weak reactivity: Faint or light brown reactivity that is membranous. Cytoplasmic reactivity that is uniform and involves all the cytoplasm may be present, but should not be evaluated for positivity. |
| Negative: Absence of membrane staining above background in all tumor cells. Presence of cytoplasmic in the absence of membrane staining. | 0.5 | Trace reactivity: Trace brown reactivity where membranous and cytoplasmic localization is indeterminate. |
| | 0 | No reactivity |

The score for each case is recorded in a database comparing the score for each binding molecule (e.g., 5B7 and 3C6). The results of each case will fall into one of the 4 categories described in Table 2. Approximately 60% of cases are expected to fall into category 1, 13% in category 2, 5% in category 3 and 22% in category 4. Patient outcome will be directly related to the scoring category as indicated in FIG. 3 and Table 2. Patients in category 1 and 3 will have a poor prognosis, and patients in categories 2 and 4 will have a better prognosis.

While this disclosure has been described with an emphasis upon particular embodiments, it will be obvious to those of ordinary skill in the art that variations of the particular embodiments may be used and it is intended that the disclosure may be practiced otherwise than as specifically described herein. Accordingly, this disclosure includes all modifications encompassed within the spirit and scope of the disclosure as defined by the following claims:

The invention claimed is:

1. A method of predicting the response of a neoplasm to an EGFR inhibitor, comprising:
    contacting a biological sample comprising one or more neoplastic cells with an epidermal growth factor receptor (EGFR) regulatory domain (RD)-antibody or antigen binding fragment thereof that specifically binds to a peptide consisting of amino acid residues 1167-1185 of SEQ ID NO: 1;
    detecting specific binding of the EGFR RD-antibody or antigen binding fragment thereof to one or more of the neoplastic cells; and
    determining that the neoplasm will respond to an EGFR inhibitor if specific binding of the EGFR RD-antibody or antigen binding fragment thereof to the one or more neoplastic cells is detected or determining that the neoplastic cells will not substantially respond to an EGFR inhibitor if substantially no specific binding of the EGFR RD-antibody or antigen binding fragment thereof to the EGFR-positive neoplastic cells is detected.

2. The method of claim 1, wherein the neoplastic cell response is slowed growth or apoptosis.

3. The method of claim 2, wherein the slowed growth is net zero growth, net negative growth, or at least 10% less than the neoplastic cell growth prior to treatment with the EGFR inhibitor.

4. The method of claim 1, wherein the biological sample is a tissue section.

5. The method of claim 4, wherein the tissue section is formalin fixed and paraffin embedded.

6. The method of claim 4, wherein the tissue section is a neoplastic tissue.

7. The method of claim 6, wherein the neoplastic tissue is a lung cancer, colorectal cancer, head and neck cancer, gastric cancer, or glioblastoma.

8. The method of claim 1, further comprising detecting in a control biological material specific binding of the EGFR RD-antibody or antigen binding fragment thereof to EGFR.

9. The method of claim 8, wherein the control biological material is normal skin, normal testis, or normal tonsil.

10. The method of claim 1, further comprising detecting in the biological sample specific binding of an antibody specific for the EGFR external domain.

11. The method of claim 1, wherein the antibody is a monoclonal antibody.

12. The method of claim 11, wherein the monoclonal antibody is a rabbit monoclonal antibody.

13. The method of claim 1, wherein detecting specific binding of the EGFR RD-antibody or antigen binding fragment thereof to one or more of the neoplastic cells comprises detecting a label present directly or indirectly bound to the EGFR RD-antibody or antigen binding fragment thereof.

14. A method for predicting whether a candidate for treatment with an EGFR inhibitor is likely to respond to such treatment, comprising:
    contacting a biological sample comprising one or more neoplastic cells with an EGFR RD-antibody or antigen binding fragment thereof that specifically binds to a peptide consisting of amino acid residues 1167-1185 of SEQ ID NO: 1, wherein the biological sample is obtained from a candidate for treatment with an EGFR inhibitor;
    detecting specific binding of the EGFR RD-antibody or antigen binding fragment thereof to one or more of the neoplastic cells; and
    determining that the candidate is likely to respond to treatment with an EGFR inhibitor when specific binding of the EGFR RD-antibody or antigen binding fragment thereof to the one or more neoplastic cells is detected.

15. The method of claim 14, wherein the biological sample is a tissue section.

16. The method of claim 15, wherein the tissue section is a neoplastic tissue.

17. The method of claim 16, wherein the neoplastic tissue is a lung cancer, colorectal cancer, head and neck cancer, gastric cancer, or glioblastoma.

18. The method of claim 14, wherein specific binding of the EGFR RD-antibody or antigen binding fragment thereof to at least 10% of the neoplastic cells in the biological sample indicates that the candidate is likely to respond to treatment with an EGFR inhibitor.

19. The method of claim 14, wherein detecting specific binding of the EGFR RD-antibody or antigen binding fragment thereof to one or more of the neoplastic cells comprises detecting a label present directly or indirectly bound to the EGFR RD-antibody or antigen binding fragment thereof.

20. A method of predicting the response of a neoplasm to EGFR inhibitor administration, comprising:
    detecting EGFR expression in a first sample of a biological material comprising one or more neoplastic cells;
    contacting a second sample of the biological material comprising one or more neoplastic cells with an EGFR RD-antibody or antigen binding fragment thereof that specifically binds to a peptide consisting of amino acid residues 1167-1185 of SEQ ID NO: 1;
    detecting in the second sample of the biological material substantially no specific binding of the EGFR RD-antibody or antigen binding fragment thereof to EGFR; and
    determining that the neoplasm is likely to respond to EGFR inhibitor administration when EGFR expression is detected but substantially no specific binding of the EGFR RD-antibody or antigen binding fragment thereof to EGFR is detected.

21. The method of claim 20, wherein the first sample and the second sample are serial sections of the biological material.

22. The method of claim 20, wherein detecting specific binding of the EGFR RD-antibody or antigen binding fragment thereof to EGFR comprises detecting a label present directly or indirectly bound to the EGFR RD-antibody or antigen binding fragment thereof.

23. The method of claim 20, wherein the neoplastic cells are from a lung cancer, colorectal cancer, head and neck cancer, gastric cancer, or glioblastoma.

24. The method of claim 20, wherein the first and second samples are tissue sections.

25. The method of claim 24, wherein the tissue sections are formalin fixed and paraffin embedded.

26. A method of detecting a direct interaction between EGFR and an EGFR regulatory protein, comprising:
   contacting a biological sample comprising one or more EGFR-positive cells, with an EGFR RD-antibody or antigen binding fragment thereof that specifically binds to a peptide consisting of amino acid residues 1167-1185 of SEQ ID NO: 1;
   detecting specific binding of the EGFR RD-antibody or antigen binding fragment thereof to the one or more EGFR-positive cells; and
   determining that EGFR is not significantly interacting with an EGFR regulatory protein when specific binding of the EGFR RD-antibody or antigen binding fragment thereof to the one or more EGFR-positive cells is detected or determining that EGFR is interacting with an EGFR regulatory protein when substantially no specific binding of the EGFR RD-antibody or antigen binding fragment thereof to the one or more EGFR-positive cells is detected as an interaction between EGFR and the EGFR regulatory protein masks the epitope of the EGFR RD-antibody or antigen binding fragment thereof.

27. The method of claim 26, wherein the EGFR regulatory protein is a SOCS protein.

28. The method of claim 26, wherein detecting specific binding of the EGFR RD-antibody or antigen binding fragment thereof to one or more of the EGFR-positive neoplastic cells comprises detecting a label present directly or indirectly bound to the EGFR RD-antibody or antigen binding fragment thereof.

29. The method of claim 26, wherein the biological sample is a tissue section.

30. The method of claim 29, wherein the tissue section is formalin fixed and paraffin embedded.

* * * * *